US010857226B2

(12) United States Patent
Martin et al.

(10) Patent No.: US 10,857,226 B2
(45) Date of Patent: *Dec. 8, 2020

(54) COMPOSITION FOR TREATING HBV INFECTION

(71) Applicant: Transgene S.A., Illkirch Graffenstaden (FR)

(72) Inventors: Perrine Martin, L'Isle d'Abeau (FR); Geneviève Inchauspe, Lyons (FR); Nathalie Silvestre, Ergersheim (FR); Doris Schmitt, Plobsheim (FR); Alexei Evlachev, Lyons (FR)

(73) Assignee: Transgene S.A., Illkirch Graffenstaden (FR)

( * ) Notice: Subject to any disclaimer, the term of this patent is extended or adjusted under 35 U.S.C. 154(b) by 57 days.

This patent is subject to a terminal disclaimer.

(21) Appl. No.: 16/132,610

(22) Filed: Sep. 17, 2018

(65) Prior Publication Data

US 2019/0070285 A1    Mar. 7, 2019

Related U.S. Application Data

(63) Continuation of application No. 13/423,193, filed on Mar. 17, 2012, now Pat. No. 10,076,570, which is a (Continued)

(30) Foreign Application Priority Data

Aug. 7, 2009  (EP) ..................................... 09305742

(51) Int. Cl.
    *A61K 39/21*    (2006.01)
    *C07K 14/005*   (2006.01)
    (Continued)

(52) U.S. Cl.
    CPC ............ *A61K 39/292* (2013.01); *A61K 39/12* (2013.01); *C07K 14/005* (2013.01);
    (Continued)

(58) Field of Classification Search
    None
    See application file for complete search history.

(56) References Cited

U.S. PATENT DOCUMENTS

| 5,981,274 A | 11/1999 | Tyrrell |
| 6,946,126 B2 | 9/2005 | Amalfitano |

(Continued)

FOREIGN PATENT DOCUMENTS

| WO | WO 92/11368 | 7/1992 |
| WO | WO 93/03764 | 3/1993 |

(Continued)

OTHER PUBLICATIONS

Zoulim et al. Safety and Immunogenicity of the Therapeutic Vaccine TG1050 in Chronic Hepatitis B Patients: A Phase 1b Placebo-Controlled Trial. Hum Vaccin Immunother. 2020: 16(2): 388-399. (Year: 2020).*

(Continued)

*Primary Examiner* — Michelle S Horning
(74) *Attorney, Agent, or Firm* — Panitch Schwarze Belisario & Nadel LLP

(57) ABSTRACT

The present invention provides a composition comprising hepatitis B virus (HBV) component(s), and which may be either nucleic acid- or polypeptide-based as well as nucleic acid molecules and vectors encoding such HBV component(s). It also relates to infectious viral particles and host cells comprising such nucleic acid molecules or vectors. It also provides composition and kits of parts comprising such (Continued)

Figure 2:
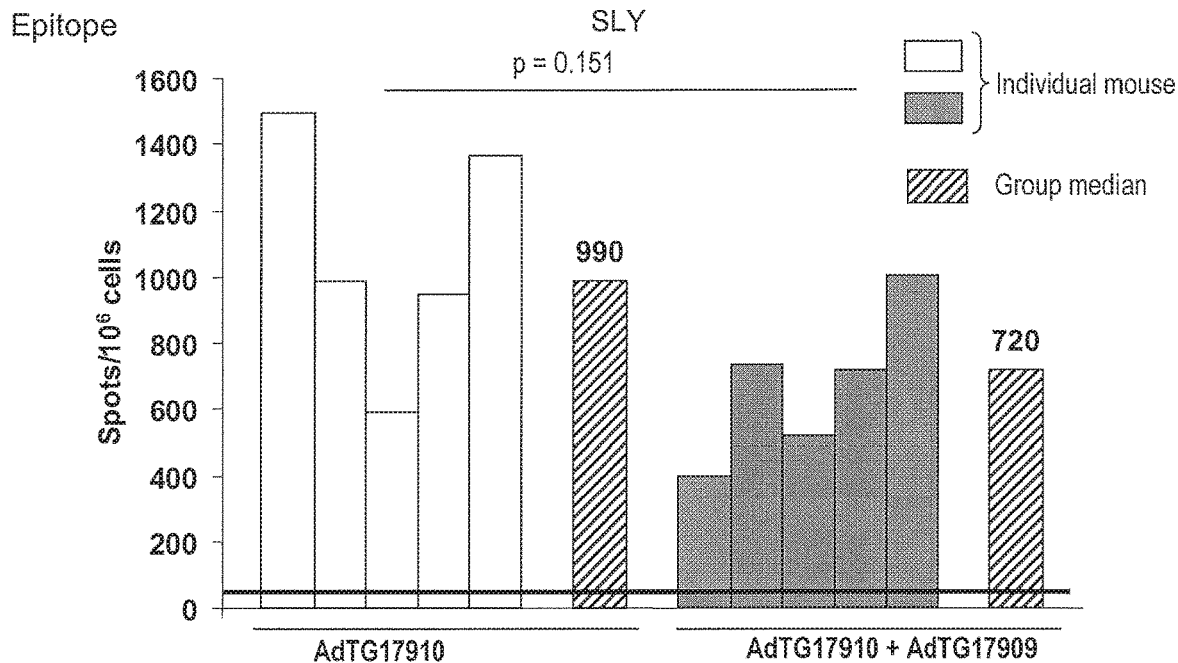
Figure 2:
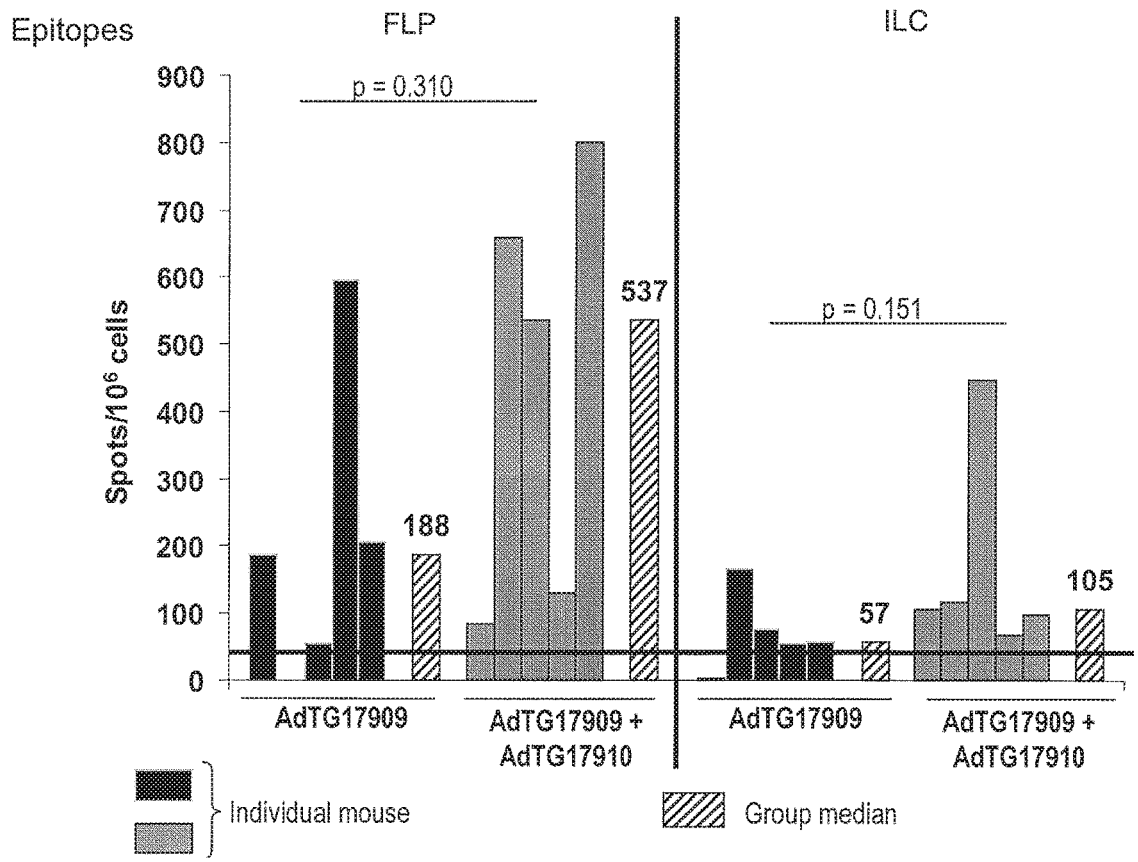
Figure 2:
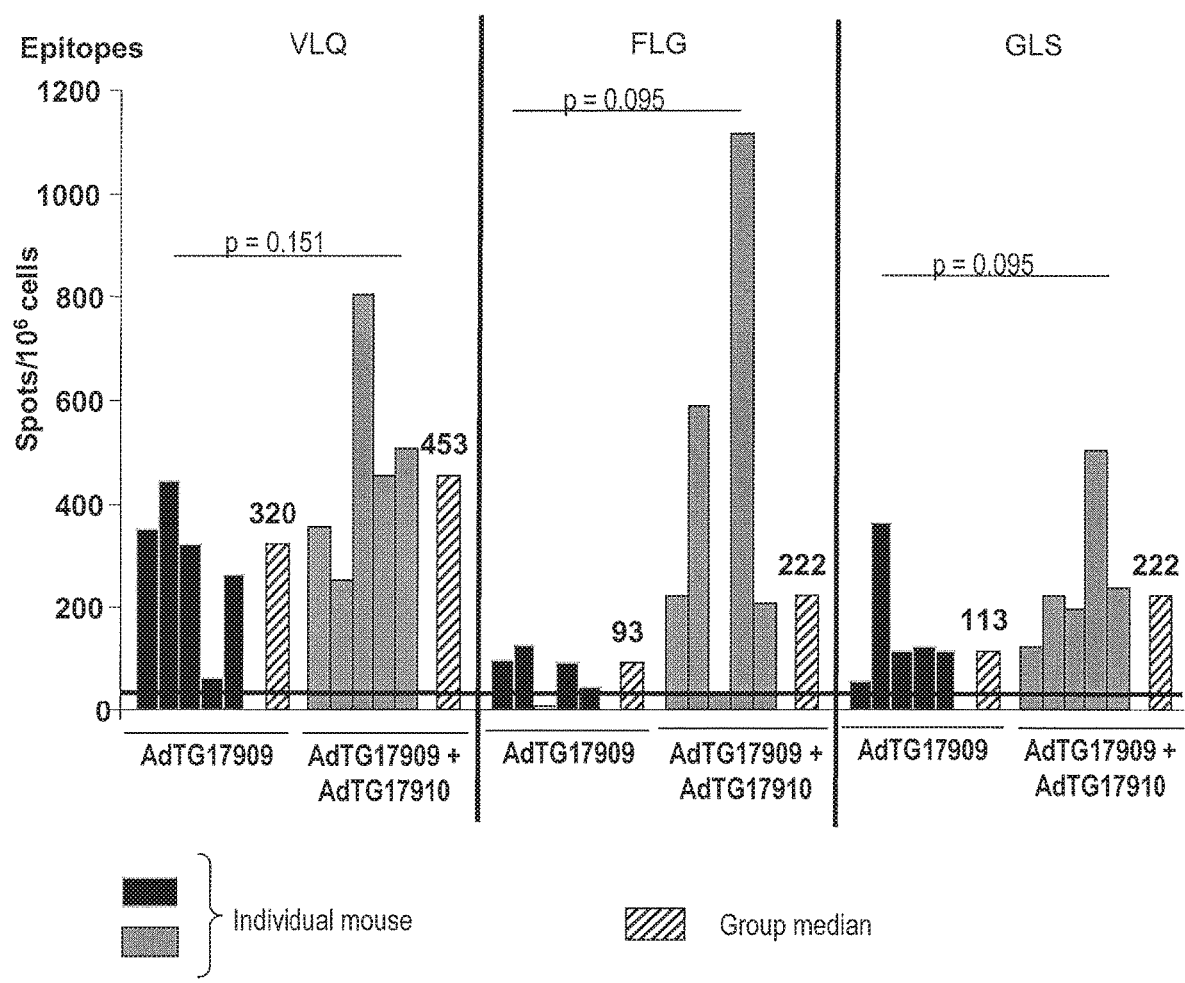

nucleic acid molecules, vectors, infectious viral particles or host cells and the therapeutic use thereof for preventing or treating HBV infections.

22 Claims, 11 Drawing Sheets

Specification includes a Sequence Listing.

Related U.S. Application Data continuation-in-part of application No. 13/388,826, filed as application No. PCT/EP2010/061492 on Aug. 6, 2010, now Pat. No. 9,393,299.

(51) Int. Cl.
| | |
|---|---|
| A61P 31/20 | (2006.01) |
| A61K 39/29 | (2006.01) |
| A61K 39/12 | (2006.01) |
| A61K 39/00 | (2006.01) |

(52) U.S. Cl.
CPC .... A61K 2039/53 (2013.01); A61K 2039/545 (2013.01); C12N 2710/10343 (2013.01); C12N 2710/24143 (2013.01); C12N 2730/10134 (2013.01); C12N 2770/24222 (2013.01)

(56) References Cited

U.S. PATENT DOCUMENTS

| | | |
|---|---|---|
| 2003/0109472 A1 | 6/2003 | Amalfitano |
| 2006/0233832 A1 | 10/2006 | Melber |

FOREIGN PATENT DOCUMENTS

| | | |
|---|---|---|
| WO | WO 94/19011 | 9/1994 |
| WO | WO 97/00698 | 1/1997 |
| WO | WO 00/32625 | 6/2000 |
| WO | WO 2005/056051 | 6/2005 |
| WO | WO 2008/020656 | 2/2008 |

OTHER PUBLICATIONS

Ward et al. Treatment of hepatitis B virus: an update. Future Microbiol. (2016) 11(12), 1581-1597 (Year: 2016).*
Julie Adkins et al., *Recombinant Hepatitis B Vaccine—A Review of its Immunogenicity and Protective Efficacy Against Hepatitis B*, 10(2) Biodrugs 137-158 (Aug. 1998).
Patrick Argos et al., *A model for the hepatitis B virus core protein: prediction of antigenic sites and relationship to RNA virus capsid proteins*, 7(3) The EMBO Journal 819-824 (1988).
Ralf Bartenschlager et al., *The P Gene Product of Hepatitis B Virus is Required as a Structural Component for Genomic RNA Encapsidation*, 64(11) Journal of Virology 5324-5332 (Nov. 1990).
Galina Borisova et al., *Hybrid Hepatitis B Virus Nucleocapsid Bearing an Immunodominant Region from Hepatitis B Virus Surface Antigen*, 67(6) Journal of Virology 3696-3701 (Jun. 1993).
Erik Depla et al., *Rational Design of a Multiepitope Vaccine Encoding T-Lymphocyte Epitopes for Treatment of Chronic Hepatitis B Virus Infections*, 82(1) Journal of Virology 435-450 (Jan. 2008).
I. Desombere et al., *Characterization of the T cell recognition of hepatitis B surface antigen (HBsAg) by good and poor responders to hepatitis B vaccines*, 122 Clin Exp Immunol 390-399 (2000).
Carol Ferrari et al., *Cellular Immune Response to Hepatitis B Virus-Encoded Antigens in Acute and Chronic Hepatitis B Virus Infection*, 145(10) The Journal of Immunology 3442-3449 (Nov. 15, 1990).

Ji Hoon Jeong et al., *The Catalytic Properties of Human Hepatitis B Virus Polymerase*, 223 Biochemical and Biophysical Research Communications 264-271 (1996).
Andris Kazaks et al., *Mosaic hepatitis B virus core particles presenting the complete preS sequence of the viral envelope on their surface*, 85 Journal of General Virology 2665-2670 (2004).
Chae Young Kim et al., *Increased in vivo immunological potency of HB-110, a novel therapeutic HBV DNA vaccine, by electroporation*, 40(6) Experimental and Molecular Medicine 669-676 (Dec. 2008).
Diana Koletzki et al., *Mosaic hepatitis B virus core particles allow insertion of extended foreign protein segments*, 78 Journal of General Virology 2049-2053 (1997).
Young Il Lee et al., *RNase H Activity of Human Hepatitis B Virus Polymerase Expressed in Escherichia coli*, 233 Biochemical and Biophysical Research Communications 401-407 (1997).
Xiangming Li et al., *A novel HBV DNA vaccine based on T cell epitopes and its potential therapeutic effect in HBV transgenic mice*, 17(10) International Immunology 1293-1302 (2005).
Heng-Gui Liu et al., *The high prevalence of the 127 mutant HBcAg18-27 epitope in Chinese HBV-infected patients and its cross-reactivity with the V27 prototype epitope*, 125 Clinical Immunology 337-345 (2007).
Delphine Loirat et al., *Multiepitopic HLA-A*0201-Restricted Immune Response Against Hepatitis B Surface Antigen After DNA-Based Immunization*, 165 Journal of Immunology 4748-4755 (2000).
Michael Lubeck et al., *Immunogenicity and efficacy testing I chimpanzees of an oral hepatitis B vaccine based on live recombinant adenovirus*, 86 Proc. Natl. Acad. Sci. USA 6763-6767 (Sep. 1989).
Maryline Mancini-Bourgine et al., *Immunogenicity of a hepatitis B DNA vaccine administered to chronic HBV carriers*, 24 Vaccine 4482-4489 (2006).
Amalia Penna et al., *Long-lasting Memory T Cell Responses following Self-limited Acute Hepatitis B*, 98(5) J. Clin. Invest. 1185-1194 (Sep. 1996).
Amalia Penna et al., *Predominant T-Helper 1 Cytokine Profile of Hepatitis Virus Nucleocapsid-Specific T Cells in Acute Self-Limited Hepatitis B*, 25(4) Hepatology 1022-1027(1997).
Gerald Radziwill et al., *Mutational Analysis of the Hepatitis B Virus P Gene Product: Domain Structure and RNase H Activity*, 64(2) Journal of Virology 613-620 (Feb. 1990).
Fenyu Ren et al., *Cytokine-Dependent Anti-Viral Role of CD4-Positive T Cells in Therapeutic Vaccination Against Chronic Hepatitis B Viral Infection*, 71 Journal of Medical Virology 376-384 (2003).
Petra Riedl et al., *Distinct, Cross-Reactive Epitope Specificities of CD8 T Cell Responses Are Induced by Natural Hepatitis B Surface Antigen Variants of Different Hepatitis B Virus Genotypes*, 176 The Journal of Immunology 4003-4011 (2006).
Reinhold Schirmbeck et al., The Immunodominant, $L^a$-Restricted T Cell Response to Hepatitis B Surface Antigen (HBsAg) Efficiently Suppresses T Cell Priming to Multiple $D^d$-, $K^d$-, and $K^b$-Restricted HBsAg Epitopes, 168 The Journal of Immunology 6253-6262 (2002).
Florian Schödel et al., *The Position of Heterologous Epitopes Inserted in Hepatitis B Virus Core Particles Determines Their Immunogenicity*, 66(1) Journal of Virology 106-114 (Jan. 1992).
Geoffrey Smith et al., *Infectious vaccinia virus recombinants that express hepatitis B virus surface antigen*, 302 Nature 490-495 (Apr. 7, 1983).
Simone Stoll-Becker et al., *Transcription of Hepatitis B Virus in Peripheral Blood Mononuclear Cells from Persistently Infected Patients*, 71(7) Journal of Virology 5399-5407 (Jul. 1997).
Pierre Vandepapeliére et al., *Therapeutic vaccination of chronic hepatitis B patients with virus suppression by antiviral therapy: A randomized, controlled study of co-administration of HBsAg/AS02 candidate vaccine and lamivudine*, 25 Vaccine 8585-8597 (2007).
George J. M. Webster et al., *Longitudinal Analysis of CD8+ T Cells Specific for Structural and Nonstructural Hepatitis B Virus Proteins in Patients with Chronic Hepatitis B: Implications for Immunotherapy*, 78(11) Journal of Virology 5707-5719 (Jun. 2004).
Yi-Ping Xing et al., *Novel DNA vaccine based on hepatitis B virus core gene induces specific immune responses in Balb/c mice*, 11(29) Would Journal of Gastroenterology 4583-4586 (2005).

(56) References Cited

OTHER PUBLICATIONS

S-H Yang et al., *Correlation of antiviral T-cell responses with suppression of viral rebound in chronic hepatitis B carriers: a proof-of-concept study*, 13 Gene Therapy 1110-1117 (2006).

Dion et al., Adeno-Associated Virus-Mediated Gene Transfer Leads to Persistent Hepatitis B Virus Replication in Mice Expressing HLA-A2 and HLA-DR1 Molecules, 87(10) Journal of Virology 5554-5563 (May 2013).

Hepatitis B, Wikipedia, 1-16 (Jan. 31, 2018).

Mancini et al. *Induction or Expansion of T-Cell Responses by a Hepatitis B DNA Vaccine Administered to Chronic HBV Carriers*, 40 Hepatology 874-882 (2004).

Baker et al., *Protein Structure Predication and Structural Genomics*, 294 (5540) Science 93-96 (2001).

Attwood, *The Babel of Bioinformatics* 290( 5491) Science 471-473 (2000).

UniPortKB—Q8UYA0 (Q8UYA0_HBV) (2002).

Blast alignment of Q8UYAO_HBV (2002) and instant SEQ ID No. 20.

Ren et al., *Hepatitis B Virus (HBV) Virion and Covalently Closed Circular DNA Formation in Primary Tupaia Hepatocytes and Human Hepatoma Cell Lines upon HBV Genome Transduction with Replication-Defective Adenovirus Vectors*, 75(3) Journal of Virology 1104-1116 (Feb. 2001).

Rehermann et al., *They Cytotoxic T Lymphocyte Response to Multiple Hepatitis B Virus Polymerase Epitopes during and After Acute Viral Hepatitis*, 181 The Journal of Experimental Medicine 1047-1058 (Mar. 1995).

Davis et al., *Expression of hepatitis B surface antigen with a recombinant adenovirus*, 82 Proc. Natl. Acad. Sci. 7560-7564 (Nov. 1985).

\* cited by examiner

Figure 1
Fig. 1A
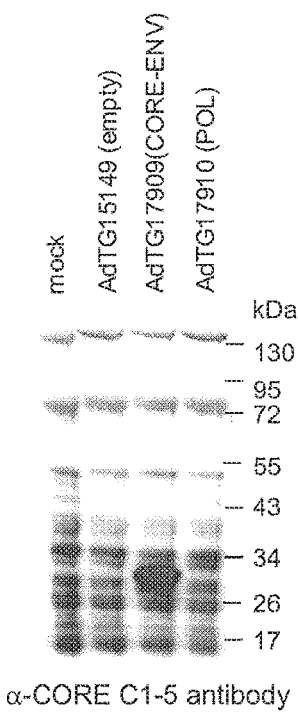
α-CORE C1-5 antibody
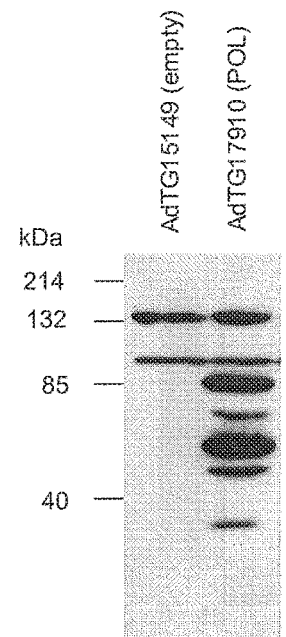
α-POL 8D5 antibody
Fig. 1B
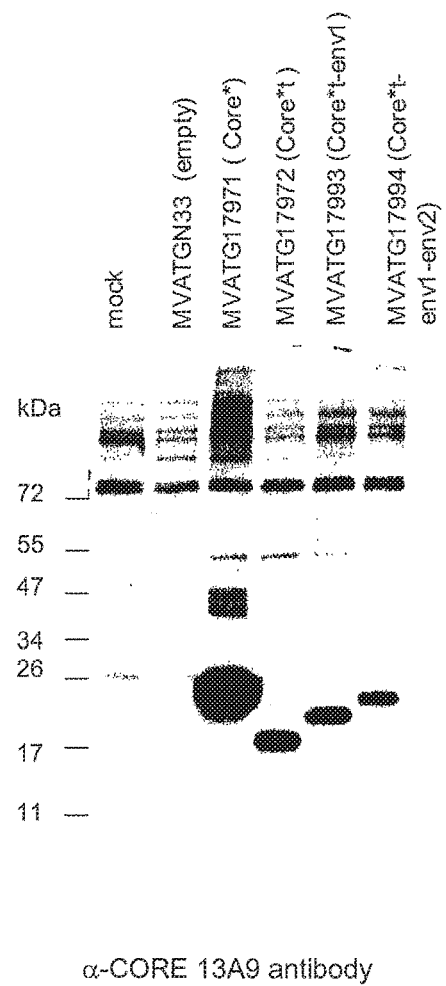
α-CORE 13A9 antibody
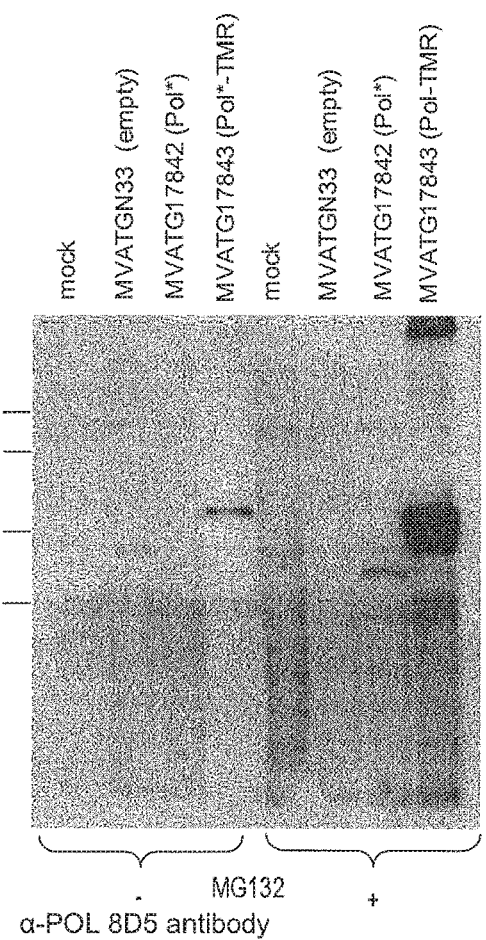
α-POL 8D5 antibody

Fig. 2A - Specific T cell responses targeting Pol protein

Fig. 2B - Specific T cell responses targeting Core protein

Figure 4:
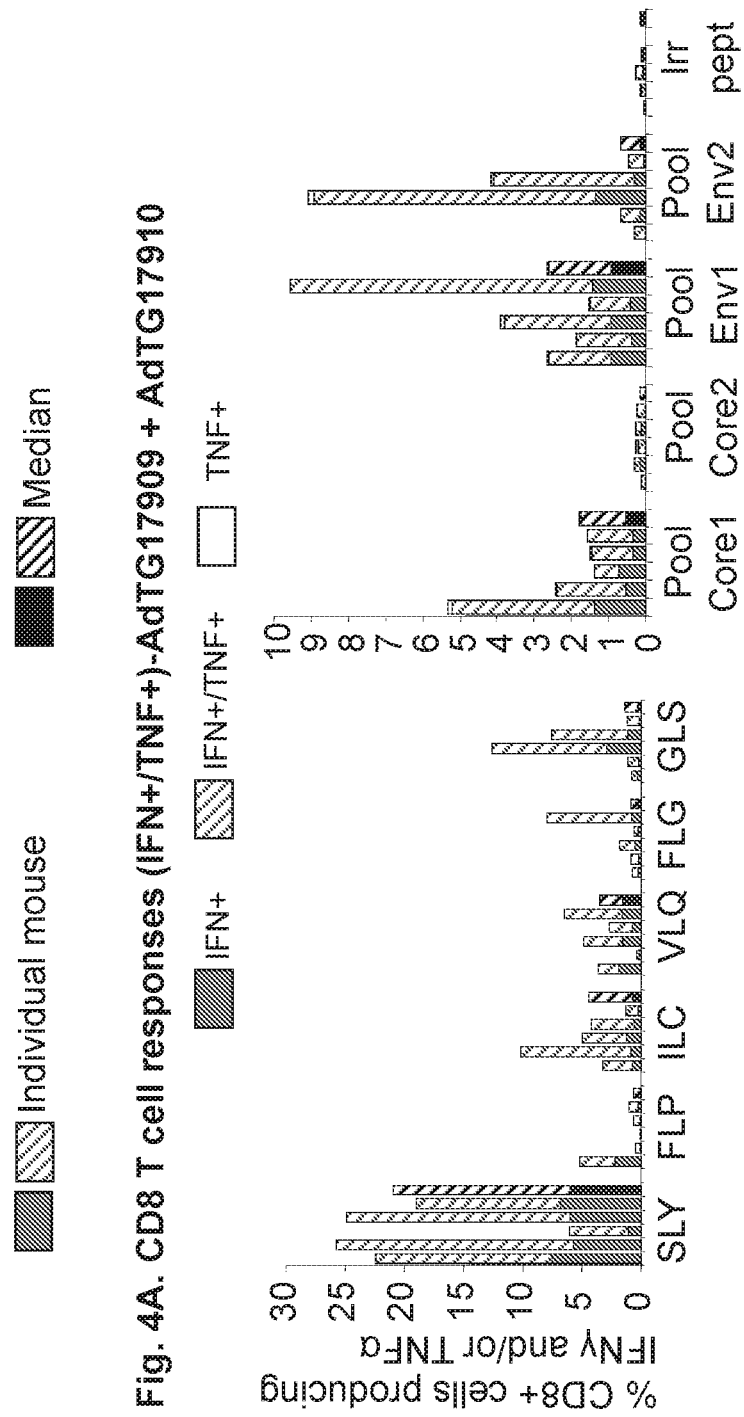
Figure 4:
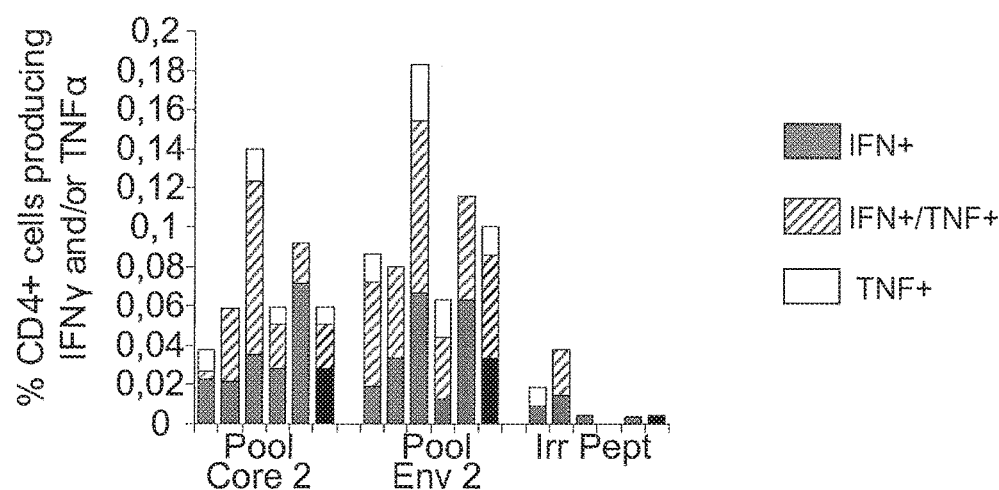
Figure 4:
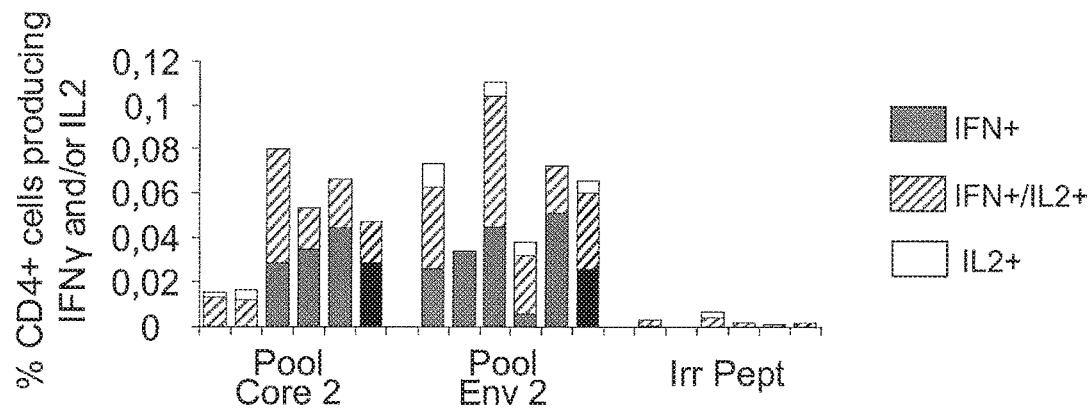

■ IFN γ CD8+ producing cells  ▨ IFNγ + TNFα CD8+ producing cells  ☐ TNF α CD8+ producing cells Fig. 4A. CD8 T cell responses (IFN+/TNF+)-AdTG17909 + AdTG17910

▨ Individual mouse    ■▨ Median

Fig. 4B. CD4 T cell responses (IFN+/TNF+)-AdTG17909+ AdTG17910

Fig. 4C. CD4 T cell responses (IFN+/IL2+)-AdTG17909+ AdTG17910

Figure 5:
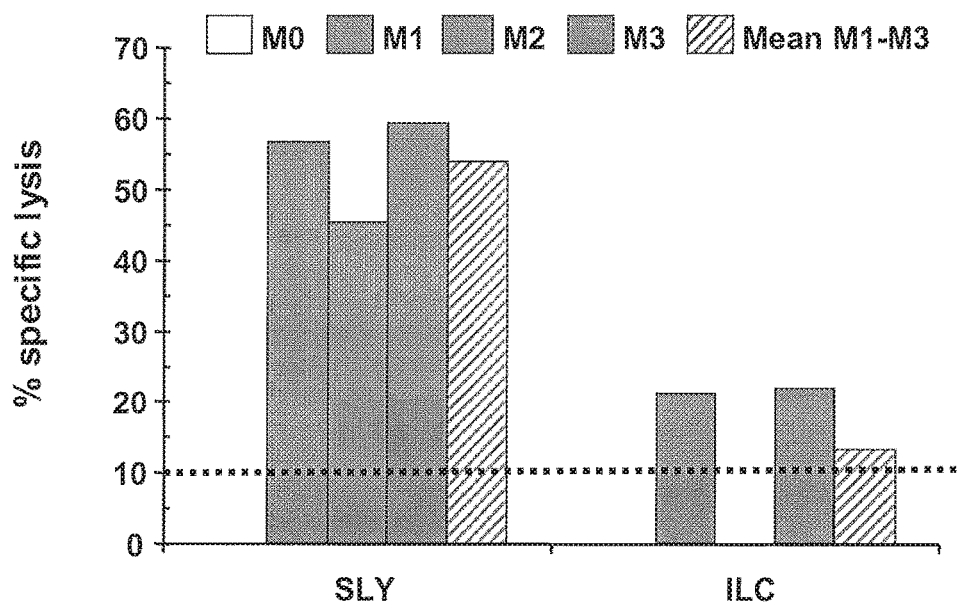
Figure 5:
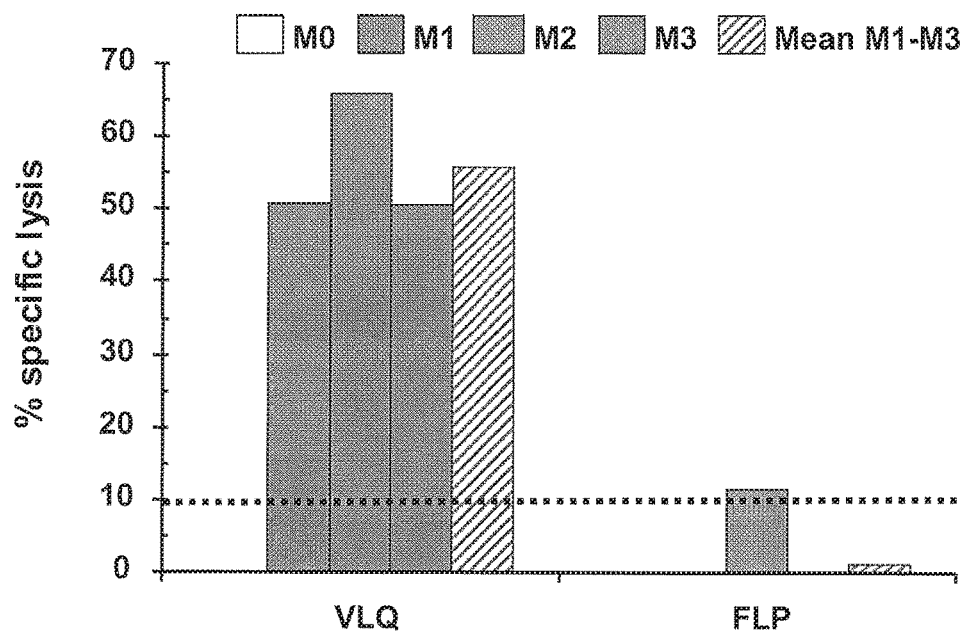

Fig5A. AdTG17909 + AdTG17910. *In vivo* lysis against SLY and ILC peptides

Fig.5B. AdTG17909 + AdTG17910. *In vivo* lysis against FLP and VLQ peptides

Figure 6:
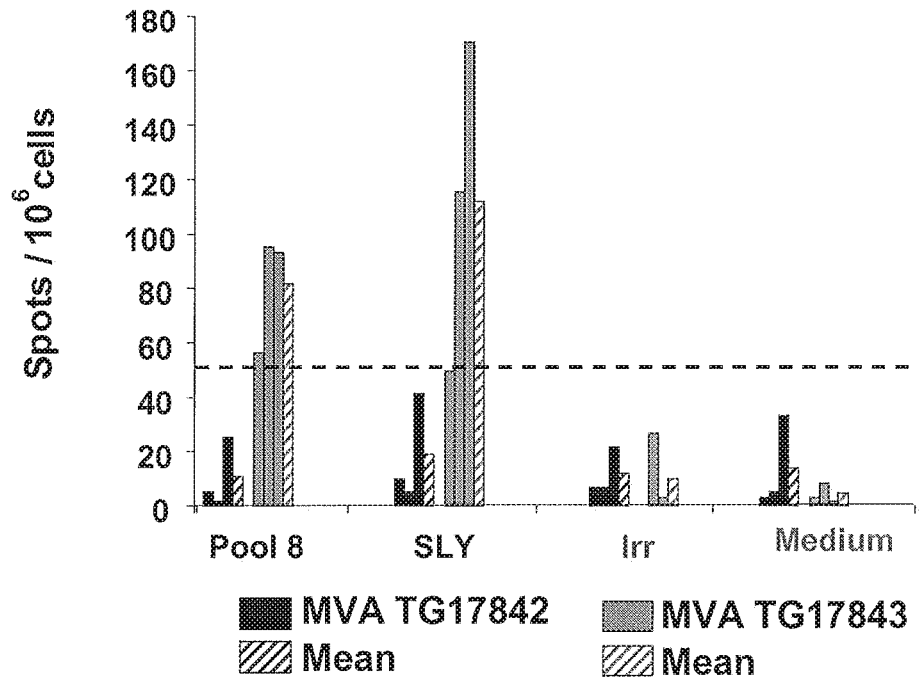
Figure 6:
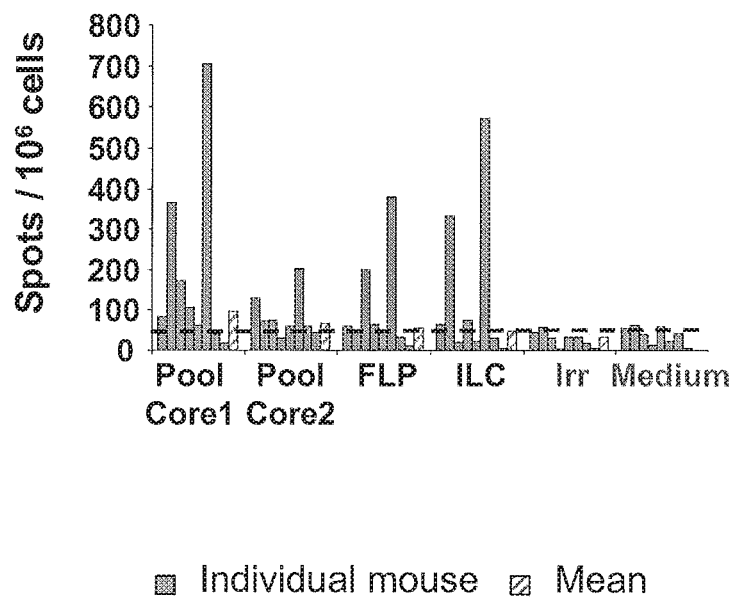

Figure 6A. MVA TG17842 or MVA TG17843

Figure 6B. MVA TG17971

Figure 7:
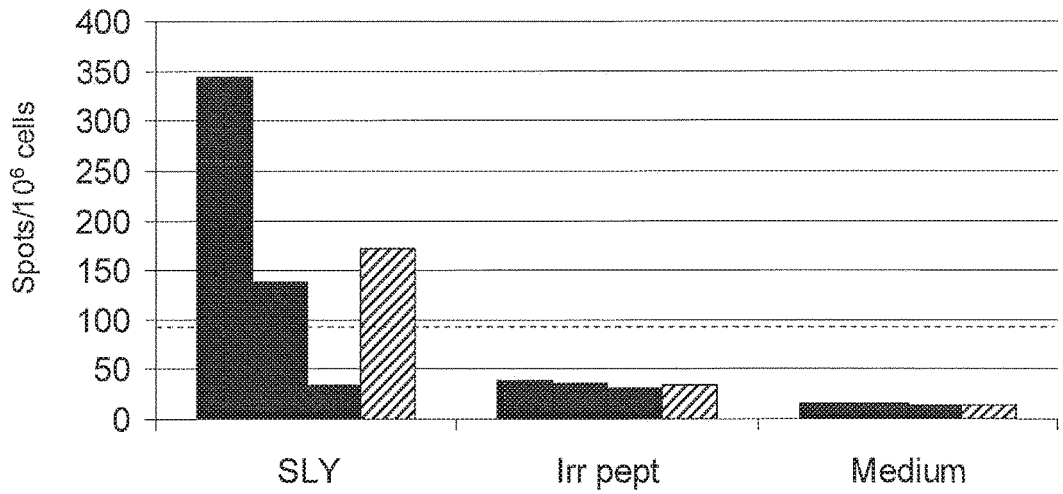
Figure 7:
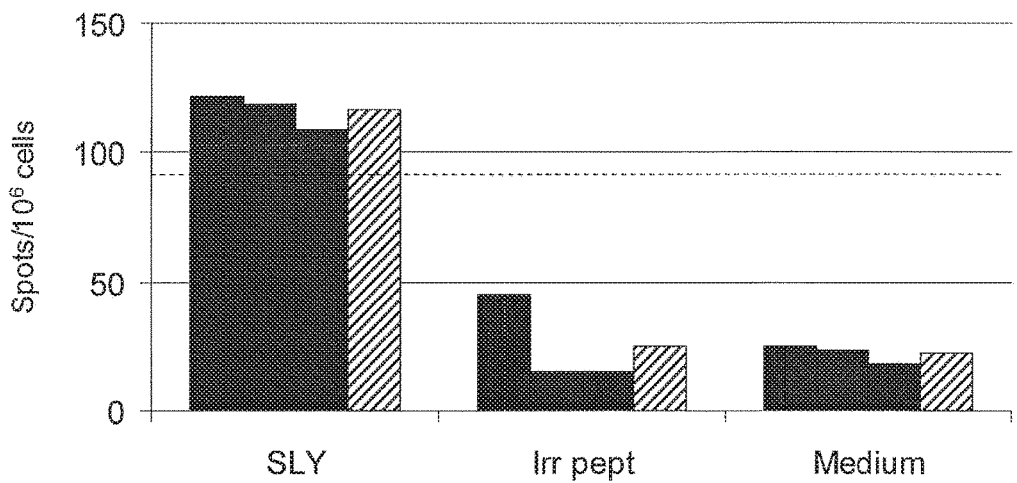
Figure 7:
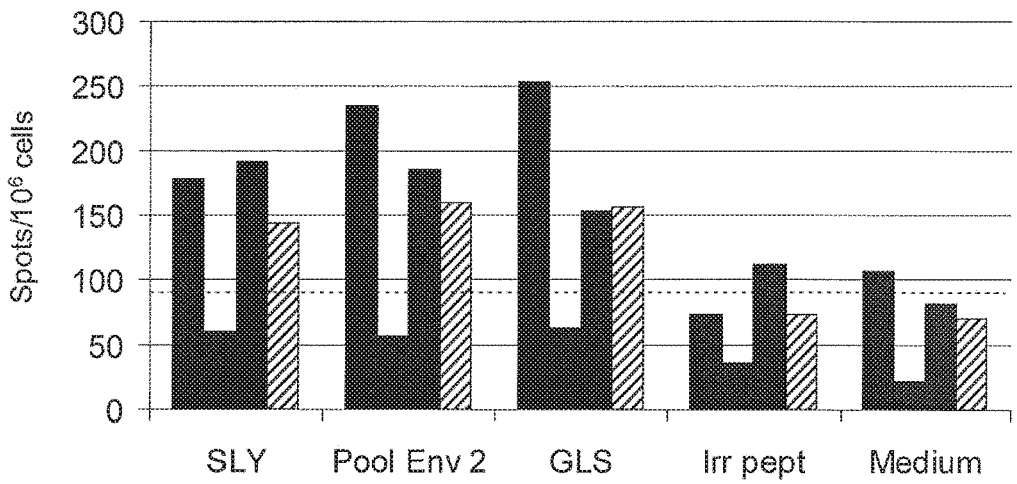

Figure 7A. MVA TG17972 + MVA TG17843

Figure 7B. MVA TG17993 + MVA TG17843

Figure 7C. MVA TG17994 + MVA TG17843

Figure 8:
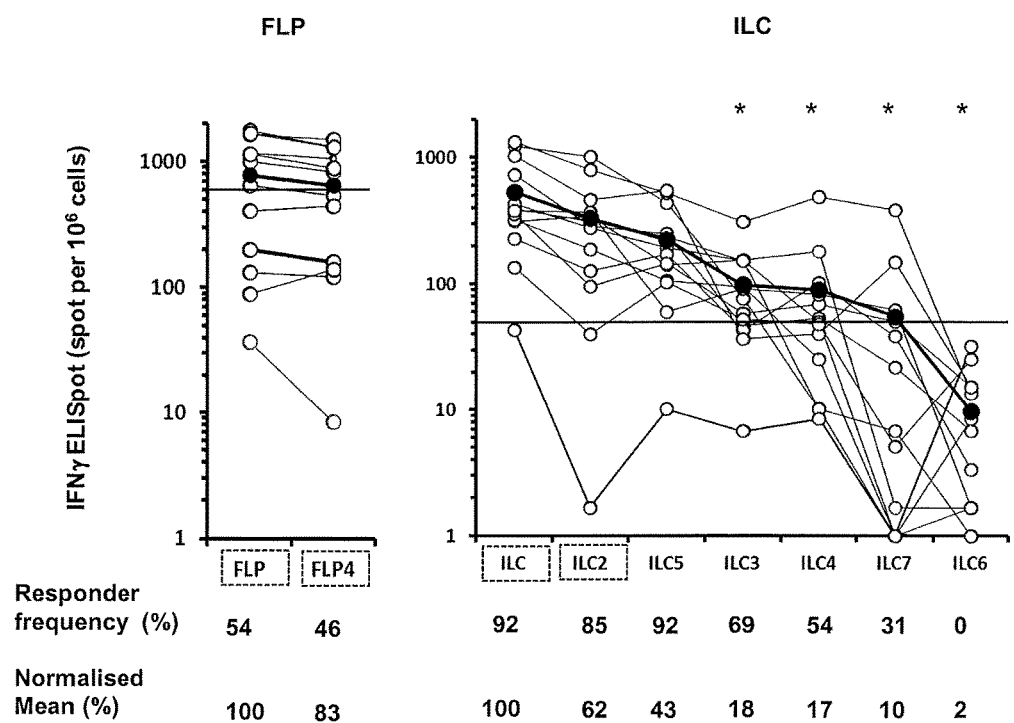
Figure 8:
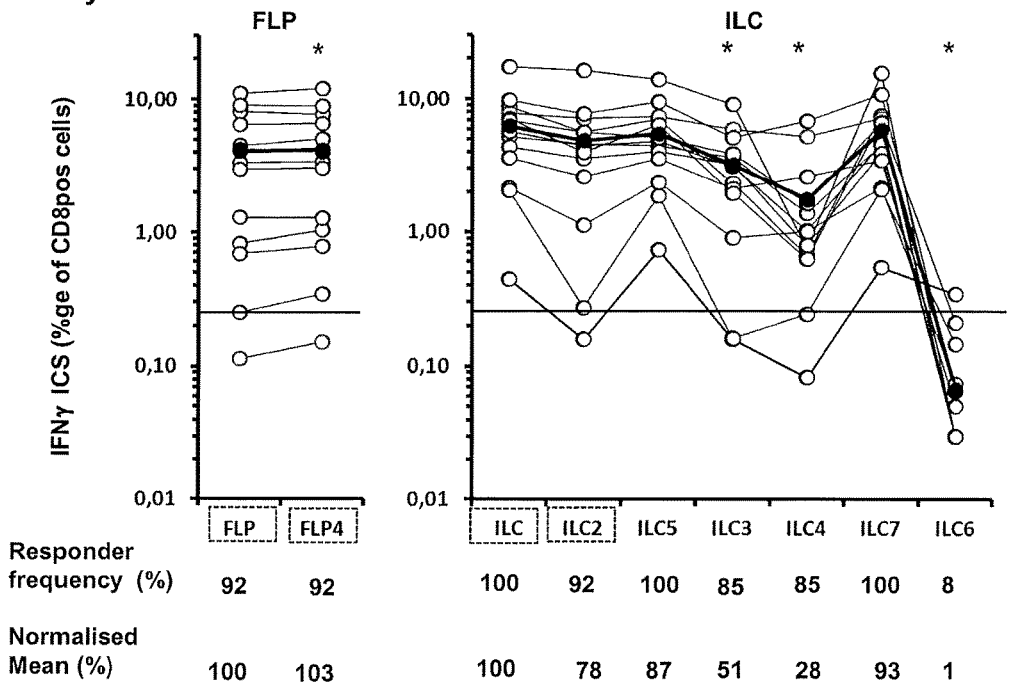

Fig. 8A A-Elispot IFNγ assay

Fig. 8B B-ICS assay

Figure 9:
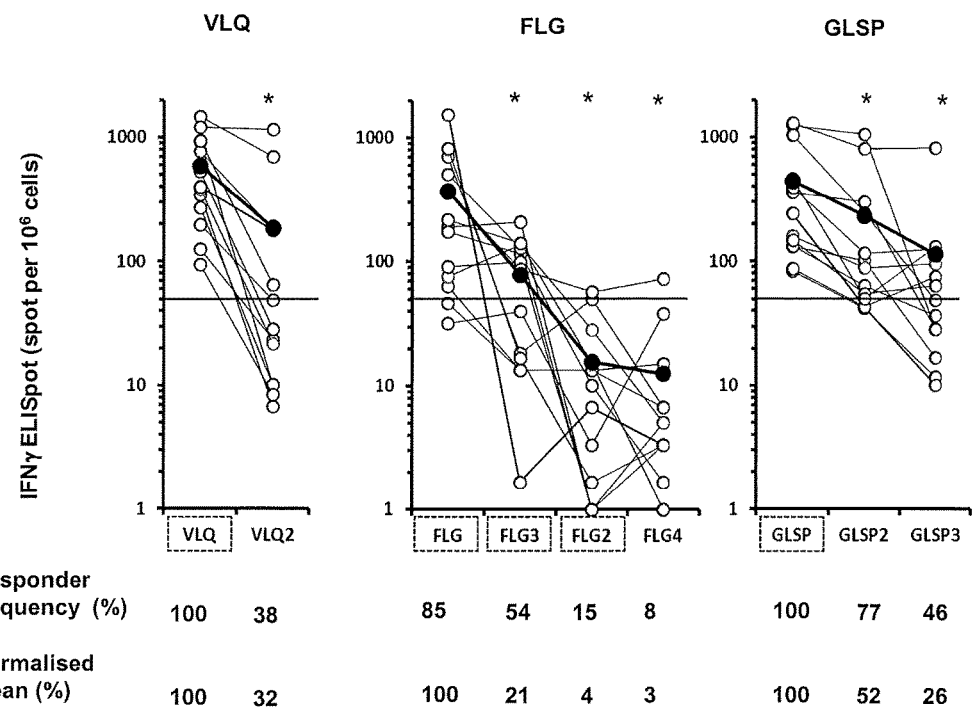
Figure 9:
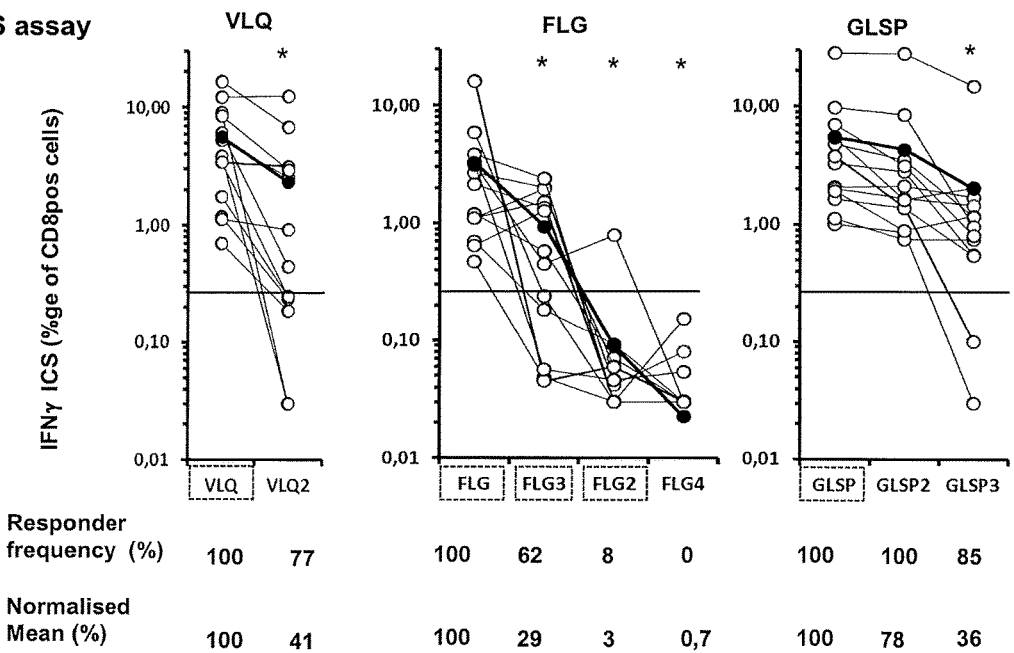

Fig. 9A  A-Elispot IFNγ assay

Fig. 9B  B-ICS assay

SEQUENCE LISTING

<160> NUMBER OF SEQ ID NOS: 75

<210> SEQ ID NO 1
<211> LENGTH: 832
<212> TYPE: PRT
<213> ORGANISM: Hepatitis B virus

<400> SEQUENCE: 1

```
Met Pro Leu Ser Tyr Gln His Phe Arg Arg Leu Leu Leu Leu Asp Asp
1               5                   10                  15

Glu Ala Gly Pro Leu Glu Glu Glu Leu Pro Arg Leu Ala Asp Glu Gly
                20                  25                  30

Leu Asn Arg Arg Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
        50                  55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
                100                 105                 110

Ala Arg Phe Tyr Pro Asn Val Thr Lys Tyr Leu Pro Leu Asp Lys Gly
```

```
            115                 120                 125
Ile Lys Pro Tyr Tyr Pro Glu His Leu Val Asn His Tyr Phe Gln Thr
    130                 135                 140
Arg His Tyr Leu His Thr Leu Trp Lys Ala Gly Ile Leu Tyr Lys Arg
145                 150                 155                 160
Glu Thr Thr His Ser Ala Ser Phe Cys Gly Ser Pro Tyr Ser Trp Glu
                165                 170                 175
Gln Lys Leu Gln His Gly Ala Glu Ser Phe His Gln Gln Ser Ser Gly
            180                 185                 190
Ile Leu Ser Arg Pro Pro Val Gly Ser Ser Leu Gln Ser Lys His Arg
        195                 200                 205
Lys Ser Arg Leu Gly Leu Gln Ser Gln Gln Gly His Leu Ala Arg Arg
    210                 215                 220
Gln Gln Gly Arg Ser Trp Ser Ile Arg Ala Gly Ile His Pro Thr Ala
225                 230                 235                 240
Arg Arg Ser Phe Gly Val Glu Pro Ser Gly Ser Gly His Ser Thr Asn
                245                 250                 255
Leu Ala Ser Lys Ser Ala Ser Cys Leu Tyr Gln Ser Pro Val Arg Lys
            260                 265                 270
Ala Ala Tyr Pro Ala Val Ser Thr Phe Glu Lys His Ser Ser Ser Gly
        275                 280                 285
His Ala Val Glu Leu His Asn Leu Pro Pro Asn Ser Ala Arg Ser Gln
    290                 295                 300
Ser Glu Arg Pro Val Phe Pro Cys Trp Trp Leu Gln Phe Arg Asn Ser
305                 310                 315                 320
Lys Pro Cys Ser Asp Tyr Cys Leu Ser His Ile Val Asn Leu Leu Glu
                325                 330                 335
Asp Trp Gly Pro Cys Ala Glu His Gly Glu His His Ile Arg Ile Pro
            340                 345                 350
Arg Thr Pro Ala Arg Val Thr Gly Gly Val Phe Leu Val Asp Lys Asn
        355                 360                 365
Pro His Asn Thr Ala Glu Ser Arg Leu Val Val Asp Phe Ser Gln Phe
    370                 375                 380
Ser Arg Gly Asn Tyr Arg Val Ser Trp Pro Lys Phe Ala Val Pro Asn
385                 390                 395                 400
Leu Gln Ser Leu Thr Asn Leu Leu Ser Ser Asn Leu Ser Trp Leu Ser
                405                 410                 415
Leu Asp Val Ser Ala Ala Phe Tyr His Leu Pro Leu His Pro Ala Ala
            420                 425                 430
Met Pro His Leu Leu Val Gly Ser Ser Gly Leu Ser Arg Tyr Val Ala
        435                 440                 445
Arg Leu Ser Ser Asn Ser Arg Ile Phe Asn Tyr Gln His Gly Thr Met
    450                 455                 460
Gln Asn Leu His Asp Ser Cys Ser Arg Asn Leu Tyr Val Ser Leu Leu
465                 470                 475                 480
Leu Leu Tyr Gln Thr Phe Gly Arg Lys Leu His Leu Tyr Ser His Pro
                485                 490                 495
Ile Ile Leu Gly Phe Arg Lys Ile Pro Met Gly Val Gly Leu Ser Pro
            500                 505                 510
Phe Leu Leu Ala Gln Phe Thr Ser Ala Ile Cys Ser Val Val Arg Arg
        515                 520                 525
Ala Phe Pro His Cys Leu Ala Phe Ser Tyr Met Asp Asp Val Val Leu
    530                 535                 540
```

Gly Ala Lys Ser Val Gln His Leu Glu Ser Leu Phe Thr Ala Val Thr
545                 550                 555                 560

Asn Phe Leu Leu Ser Leu Gly Ile His Leu Asn Pro Asn Lys Thr Lys
            565                 570                 575

Arg Trp Gly Tyr Ser Leu His Phe Met Gly Tyr Val Ile Gly Cys Tyr
        580                 585                 590

Gly Ser Leu Pro Gln Asp His Ile Ile Gln Lys Ile Lys Glu Cys Phe
    595                 600                 605

Arg Lys Leu Pro Val Asn Arg Pro Ile Asp Trp Lys Val Cys Gln Arg
610                 615                 620

Ile Val Gly Leu Leu Gly Phe Ala Ala Pro Phe Thr Gln Cys Gly Tyr
625                 630                 635                 640

Pro Ala Leu Met Pro Leu Tyr Ala Cys Ile Gln Ser Lys Gln Ala Phe
            645                 650                 655

Thr Phe Ser Pro Thr Tyr Lys Ala Phe Leu Cys Lys Gln Tyr Leu Asn
        660                 665                 670

Leu Tyr Pro Val Ala Arg Gln Arg Pro Gly Leu Cys Gln Val Phe Ala
    675                 680                 685

Asp Ala Thr Pro Thr Gly Trp Gly Leu Val Met Gly His Gln Arg Met
690                 695                 700

Arg Gly Thr Phe Leu Ala Pro Leu Pro Ile His Thr Ala Glu Leu Leu
705                 710                 715                 720

Ala Ala Cys Phe Ala Arg Ser Arg Ser Gly Ala Asn Ile Leu Gly Thr
            725                 730                 735

Asp Asn Ser Val Val Leu Ser Arg Lys Tyr Thr Ser Phe Pro Trp Leu
        740                 745                 750

Leu Gly Cys Ala Ala Asn Trp Ile Leu Arg Gly Thr Ser Phe Val Tyr
    755                 760                 765

Val Pro Ser Ala Leu Asn Pro Thr Asp Asp Pro Ser Arg Gly Arg Leu
770                 775                 780

Gly Leu Ser Arg Pro Leu Leu Arg Leu Pro Phe Arg Pro Thr Thr Gly
785                 790                 795                 800

Arg Thr Ser Leu Tyr Ala Asp Ser Pro Ser Val Pro Ser His Leu Pro
            805                 810                 815

Asp Arg Val His Phe Ala Ser Pro Leu His Val Ala Trp Arg Pro Pro
        820                 825                 830

<210> SEQ ID NO 2
<211> LENGTH: 183
<212> TYPE: PRT
<213> ORGANISM: Hepatitis B virus

<400> SEQUENCE: 2

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ile
65                  70                  75                  80

Ser Arg Asp Leu Val Val Ser Tyr Val Asn Thr Asn Met Gly Leu Lys

```
                    85                  90                  95
Phe Arg Gln Leu Leu Trp Phe His Ile Ser Cys Leu Thr Phe Gly Arg
                100                 105                 110
Glu Thr Val Ile Glu Tyr Leu Val Ser Phe Gly Val Trp Ile Arg Thr
                115                 120                 125
Pro Pro Ala Tyr Arg Pro Pro Asn Ala Pro Ile Leu Ser Thr Leu Pro
            130                 135                 140
Glu Thr Thr Val Val Arg Arg Arg Gly Arg Ser Pro Arg Arg Arg Thr
145                 150                 155                 160
Pro Ser Pro Arg Arg Arg Arg Ser Gln Ser Pro Arg Arg Arg Arg Ser
                165                 170                 175
Gln Ser Arg Glu Ser Gln Cys
                180

<210> SEQ ID NO 3
<211> LENGTH: 226
<212> TYPE: PRT
<213> ORGANISM: Hepatitis B virus

<400> SEQUENCE: 3

Met Glu Asn Ile Thr Ser Gly Phe Leu Gly Pro Leu Leu Val Leu Gln
1               5                   10                  15
Ala Gly Phe Phe Leu Leu Thr Arg Ile Leu Thr Ile Pro Gln Ser Leu
                20                  25                  30
Asp Ser Trp Trp Thr Ser Leu Asn Phe Leu Gly Gly Thr Thr Val Cys
            35                  40                  45
Leu Gly Gln Asn Ser Gln Ser Pro Thr Ser Asn His Ser Pro Thr Ser
    50                  55                  60
Cys Pro Pro Thr Cys Pro Gly Tyr Arg Trp Met Cys Leu Arg Arg Phe
65                  70                  75                  80
Ile Ile Phe Leu Phe Ile Leu Leu Cys Leu Ile Phe Leu Leu Val
                85                  90                  95
Leu Leu Asp Tyr Gln Gly Met Leu Pro Val Cys Pro Leu Ile Pro Gly
                100                 105                 110
Ser Ser Thr Thr Ser Thr Gly Pro Cys Arg Thr Cys Thr Thr Pro Ala
            115                 120                 125
Gln Gly Thr Ser Met Tyr Pro Ser Cys Cys Cys Thr Lys Pro Ser Asp
        130                 135                 140
Gly Asn Cys Thr Cys Ile Pro Ile Pro Ser Ser Trp Ala Phe Gly Lys
145                 150                 155                 160
Phe Leu Trp Glu Trp Ala Ser Ala Arg Phe Ser Trp Leu Ser Leu Leu
                165                 170                 175
Val Pro Phe Val Gln Trp Phe Val Gly Leu Ser Pro Thr Val Trp Leu
            180                 185                 190
Ser Val Ile Trp Met Met Trp Tyr Trp Gly Pro Ser Leu Tyr Ser Ile
        195                 200                 205
Leu Ser Pro Phe Leu Pro Leu Leu Pro Ile Phe Phe Cys Leu Trp Val
    210                 215                 220
Tyr Ile
225

<210> SEQ ID NO 4
<211> LENGTH: 2499
<212> TYPE: DNA
<213> ORGANISM: Hepatitis B virus
```

```
<400> SEQUENCE: 4
atgcccctat cttatcaaca cttccggaga ctactgttgt tagacgacga ggcaggtccc      60
ctagaagaag aactccctcg cctcgcagac gaaggtctca atcgccgcgt cgcagaagat     120
ctcaatctcg ggaatctcaa tgttagtatt ccttggactc ataaggtggg aaactttacg     180
gggctttatt cttctactgt acctgtcttt aaccctcatt ggaaaacacc ctcttttcct     240
aatatacatt tacaccaaga cattatcaaa aaatgtgaac aatttgtagg cccactcaca     300
gtcaatgaga aagaagact gcaattgatt atgcctgcta ggttttatcc aaatgttacc      360
aaatatttgc cattggataa gggtattaaa ccttattatc cagaacatct agttaatcat     420
tacttccaaa ccagacatta tttacacact ctatggaagg cgggtatatt atataagaga     480
gaaacaacac atagtgcctc attttgtggg tcaccatatt cttgggaaca aaagctacag     540 catgggcag aatcttttcca ccagcaatcc tctgggattc tttcccgacc accagttgga     600
tccagccttc agagcaaaca ccgcaaatcc agattgggac ttcaatccca acaaggacac     660
ctggccagac gccaacaagg taggagctgg agcattcggg ctgggattca ccccaccgca     720
cggaggtctt ttggggtgga gccctcaggc tcagggcatt ctacaaacct tgccagcaaa     780
tccgcctcct gcctctacca atcgccagtc aggaaggcag cctaccccgc tgtctccacc     840
tttgagaaac actcatcctc aggccatgca gtggaactcc acaaccttcc accaaactct     900
gcaagatccc agagtgagag gcctgtattt ccctgctggt ggctccagtt caggaacagt     960
aaaccctgtt ccgactactg tctctcccat atcgtcaatc ttctcgagga ttggggaccc    1020
tgcgctgaac atggagaaca tcacatcagg attcctagga cccctgctcg tgttacaggc    1080 ggggttttc ttgttgacaa gaatcctcac aataccgcag agtctagact cgtggtggac     1140
ttctctcaat tttctagggg gaactaccgt gtgtcttggc caaaattcgc agtccccaac    1200
ctccaatcac tcaccaacct cctgtcctcc aacctgtcct ggttatcgct ggatgtgtct    1260
gcggcgtttt atcatcttcc tcttcatcct gctgctatgc ctcatcttct tgttggttct    1320
tctggactat caaggtatgt tgcccgtttg tcctctaatt ccaggatctt caactaccag    1380
cacgggacca tgcagaacct gcacgactcc tgctcaagga acctctatgt atccctcctg    1440
ttgctgtacc aaaccttcgg acggaaattg cacctgtatt cccatcccat catcctgggc    1500
tttcggaaaa ttcctatggg agtgggcctc agcccgtttc tcctggctca gtttactagt    1560
gccatttgtt cagtggttcg tagggctttc ccccactgtt tggctttcag ttatatggat    1620
gatgtggtat tggggccaa gtctgtacag catcttgagt cccttttttac cgctgttacc    1680 aatttttcttt tgtctttggg tatacattta aaccctaaca aaacaaaaag atggggttac    1740
tctttacatt tcatgggcta tgtcattgga tgttatgggt cattgccaca agatcacatc    1800
atacaaaaaa tcaagaatg ttttcgaaaa cttcctgtta acagacctat tgattggaaa     1860
gtctgtcaac gtattgtggg tcttttgggt tttgctgccc ttttacaca atgtggttat     1920 cctgctttaa tgcctttgta tgcatgtatt cagtcgaagc aggcttttac tttctcgcca    1980
acttacaagg cctttctgtg taaacaatac ctgaaccttt accccgttgc ccggcaacgg    2040
ccaggtctgt gccaagtgtt tgctgacgca acccccactg ctggggctt ggtcatgggc     2100 catcagcgca tgcgtggaac cttcctggct cctctgccga tccatactgc ggaactccta    2160
gccgcttgtt ttgctcgcag caggtctgga gcaaacattc tcgggacgga taactctgtt    2220
gttctctccc gcaaatatac atcgtttcca tggctgctag gctgtgctgc caactggatc    2280
ctgcgcggga cgtcctttgt ttacgtcccg tcggcgctga atcccacgga cgacccttct    2340
```

```
cggggtcgct tggggctctc tcgtcccctt ctccgtctac cgtttcgacc gaccacgggg    2400
cgcacctctc tttacgcgga ctccccgtct gtgccttctc atctgccgga ccgtgtgcac    2460
ttcgcttcac ctctgcacgt cgcatggaga ccaccgtga                           2499

<210> SEQ ID NO 5
<211> LENGTH: 552
<212> TYPE: DNA
<213> ORGANISM: Hepatitis B virus

<400> SEQUENCE: 5
atggacattg atccttataa agaatttgga gctactgtgg agttactctc ttttttgcct      60
tctgacttct ttccttcagt acgtgatctt ctagataccg cctcagctct gtatcgggaa    120
gccttagagt ctcctgagca ttgttcacct caccatactg ctctcaggca agcaattctg    180
tgctgggggg aactaatgac tctagctacc tgggtgggtg gtaatttgga agatccaata    240
tccagggacc tagtagtcag ttatgtcaac actaatatgg gcctaaagtt ccggcaacta    300
ttgtggtttc acatttcttg tctcactttt ggaagagaaa cagttataga atatttggtg    360
tctttcggag tgtggattcg cactcctcca gcttatagac caccaaatgc ccctatctta    420
tcaacacttc cggagactac tgttgttaga cgacgaggca ggtcccctag aagaagaact    480
ccctcgcctc gcagacgaag gtctcaatcg ccgcgtcgca agatctcaa atctcgggaa    540 tctcaatgtt aa                                                        552

<210> SEQ ID NO 6
<211> LENGTH: 681
<212> TYPE: DNA
<213> ORGANISM: Hepatitis B virus

<400> SEQUENCE: 6
atggagaaca tcacatcagg attcctagga cccctgctcg tgttacaggc ggggtttttc      60
ttgttgacaa gaatcctcac aataccgcag agtctagact cgtggtggac ttctctcaat    120
tttctagggg gaactaccgt gtgtcttggc caaaattcgc agtccccaac ctccaatcac    180
tcaccaacct cctgtcctcc aacctgtcct ggttatcgct ggatgtgtct gcggcgtttt    240
atcatcttcc tcttcatcct gctgctatgc ctcatcttct tgttggttct tctggactat    300
caaggtatgt tgcccgtttg tcctctaatt ccaggatctt caactaccag cacgggacca    360
tgcagaacct gcacgactcc tgctcaagga acctctatgt atccctcctg ttgctgtacc    420
aaaccttcgg acgaaaattg cacctgtatt cccatcccat catcctgggc tttcggaaaa    480
ttcctatggg agtgggcctc agcccgtttc tcctggctca gtttactagt gccatttgtt    540
cagtggttcg tagggctttc ccccactgtt tggctttcag ttatatggat gatgtggtat    600
tgggggccaa gtctgtacag catcttgagt cccttttac cgctgttacc aattttcttt    660
tgtctttggg tatacattta a                                              681

<210> SEQ ID NO 7
<211> LENGTH: 786
<212> TYPE: PRT
<213> ORGANISM: artificial sequence
<220> FEATURE:
<223> OTHER INFORMATION: N-terminally truncated HBV polymerase (48-832)

<400> SEQUENCE: 7

Met Val Ser Ile Pro Trp Thr His Lys Val Gly Asn Phe Thr Gly Leu
1               5                   10                  15
```

```
Tyr Ser Ser Thr Val Pro Val Phe Asn Pro His Trp Lys Thr Pro Ser
            20              25                  30

Phe Pro Asn Ile His Leu His Gln Asp Ile Ile Lys Lys Cys Glu Gln
            35              40                  45

Phe Val Gly Pro Leu Thr Val Asn Glu Lys Arg Leu Gln Leu Ile
 50              55                  60

Met Pro Ala Arg Phe Tyr Pro Asn Val Thr Lys Tyr Leu Pro Leu Asp
 65              70                  75                  80

Lys Gly Ile Lys Pro Tyr Tyr Pro Glu His Leu Val Asn His Tyr Phe
                85              90                  95

Gln Thr Arg His Tyr Leu His Thr Leu Trp Lys Ala Gly Ile Leu Tyr
            100             105                 110

Lys Arg Glu Thr Thr His Ser Ala Ser Phe Cys Gly Ser Pro Tyr Ser
            115             120                 125

Trp Glu Gln Lys Leu Gln His Gly Ala Glu Ser Phe His Gln Gln Ser
            130             135                 140

Ser Gly Ile Leu Ser Arg Pro Val Gly Ser Ser Leu Gln Ser Lys
145             150                 155                 160

His Arg Lys Ser Arg Leu Gly Leu Gln Ser Gln Gln Gly His Leu Ala
                165             170                 175

Arg Arg Gln Gln Gly Arg Ser Trp Ser Ile Arg Ala Gly Ile His Pro
            180             185                 190

Thr Ala Arg Arg Ser Phe Gly Val Glu Pro Ser Gly Ser Gly His Ser
            195             200                 205

Thr Asn Leu Ala Ser Lys Ser Ala Ser Cys Leu Tyr Gln Ser Pro Val
            210             215                 220

Arg Lys Ala Ala Tyr Pro Ala Val Ser Thr Phe Glu Lys His Ser Ser
225             230             235                 240

Ser Gly His Ala Val Glu Leu His Asn Leu Pro Pro Asn Ser Ala Arg
            245             250                 255

Ser Gln Ser Glu Arg Pro Val Phe Pro Cys Trp Trp Leu Gln Phe Arg
            260             265                 270

Asn Ser Lys Pro Cys Ser Asp Tyr Cys Leu Ser His Ile Val Asn Leu
            275             280                 285

Leu Glu Asp Trp Gly Pro Cys Ala Glu His Gly Glu His His Ile Arg
            290             295                 300

Ile Pro Arg Thr Pro Ala Arg Val Thr Gly Gly Val Phe Leu Val Asp
305             310                 315                 320

Lys Asn Pro His Asn Thr Ala Glu Ser Arg Leu Val Val Asp Phe Ser
                325             330                 335

Gln Phe Ser Arg Gly Asn Tyr Arg Val Ser Trp Pro Lys Phe Ala Val
            340             345                 350

Pro Asn Leu Gln Ser Leu Thr Asn Leu Leu Ser Ser Asn Leu Ser Trp
            355             360                 365

Leu Ser Leu Asp Val Ser Ala Ala Phe Tyr His Leu Pro Leu His Pro
            370             375                 380

Ala Ala Met Pro His Leu Leu Val Gly Ser Ser Gly Leu Ser Arg Tyr
385             390                 395                 400

Val Ala Arg Leu Ser Ser Asn Ser Arg Ile Phe Asn Tyr Gln His Gly
            405             410                 415

Thr Met Gln Asn Leu His Asp Ser Cys Ser Arg Asn Leu Tyr Val Ser
            420             425                 430
```

Leu Leu Leu Leu Tyr Gln Thr Phe Gly Arg Lys Leu His Leu Tyr Ser
            435                 440                 445

His Pro Ile Ile Leu Gly Phe Arg Lys Ile Pro Met Gly Val Gly Leu
450                 455                 460

Ser Pro Phe Leu Leu Ala Gln Phe Thr Ser Ala Ile Cys Ser Val Val
465                 470                 475                 480

Arg Arg Ala Phe Pro His Cys Leu Ala Phe Ser Tyr Met Asp Asp Val
                485                 490                 495

Val Leu Gly Ala Lys Ser Val Gln His Leu Glu Ser Leu Phe Thr Ala
            500                 505                 510

Val Thr Asn Phe Leu Leu Ser Leu Gly Ile His Leu Asn Pro Asn Lys
        515                 520                 525

Thr Lys Arg Trp Gly Tyr Ser Leu His Phe Met Gly Tyr Val Ile Gly
    530                 535                 540

Cys Tyr Gly Ser Leu Pro Gln Asp His Ile Ile Gln Lys Ile Lys Glu
545                 550                 555                 560

Cys Phe Arg Lys Leu Pro Val Asn Arg Pro Ile Asp Trp Lys Val Cys
                565                 570                 575

Gln Arg Ile Val Gly Leu Leu Gly Phe Ala Ala Pro Phe Thr Gln Cys
            580                 585                 590

Gly Tyr Pro Ala Leu Met Pro Leu Tyr Ala Cys Ile Gln Ser Lys Gln
        595                 600                 605

Ala Phe Thr Phe Ser Pro Thr Tyr Lys Ala Phe Leu Cys Lys Gln Tyr
    610                 615                 620

Leu Asn Leu Tyr Pro Val Ala Arg Gln Arg Pro Gly Leu Cys Gln Val
625                 630                 635                 640

Phe Ala Asp Ala Thr Pro Thr Gly Trp Gly Leu Val Met Gly His Gln
                645                 650                 655

Arg Met Arg Gly Thr Phe Leu Ala Pro Leu Pro Ile His Thr Ala Glu
            660                 665                 670

Leu Leu Ala Ala Cys Phe Ala Arg Ser Arg Ser Gly Ala Asn Ile Leu
        675                 680                 685

Gly Thr Asp Asn Ser Val Val Leu Ser Arg Lys Tyr Thr Ser Phe Pro
    690                 695                 700

Trp Leu Leu Gly Cys Ala Ala Asn Trp Ile Leu Arg Gly Thr Ser Phe
705                 710                 715                 720

Val Tyr Val Pro Ser Ala Leu Asn Pro Thr Asp Asp Pro Ser Arg Gly
                725                 730                 735

Arg Leu Gly Leu Ser Arg Pro Leu Leu Arg Leu Pro Phe Arg Pro Thr
            740                 745                 750

Thr Gly Arg Thr Ser Leu Tyr Ala Asp Ser Pro Ser Val Pro Ser His
        755                 760                 765

Leu Pro Asp Arg Val His Phe Ala Ser Pro Leu His Val Ala Trp Arg
    770                 775                 780

Pro Pro
785

<210> SEQ ID NO 8
<211> LENGTH: 832
<212> TYPE: PRT
<213> ORGANISM: artificial sequence
<220> FEATURE:
<223> OTHER INFORMATION: mutated polymerase deficient in RTase and RNase
      H activities

<400> SEQUENCE: 8

```
Met Pro Leu Ser Tyr Gln His Phe Arg Arg Leu Leu Leu Asp Asp
1               5                   10                  15

Glu Ala Gly Pro Leu Glu Glu Leu Pro Arg Leu Ala Asp Glu Gly
                20                  25                  30

Leu Asn Arg Arg Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
50                  55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
                100                 105                 110

Ala Arg Phe Tyr Pro Asn Val Thr Lys Tyr Leu Pro Leu Asp Lys Gly
            115                 120                 125

Ile Lys Pro Tyr Tyr Pro Glu His Leu Val Asn His Tyr Phe Gln Thr
            130                 135                 140

Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Lys Leu Gln His Gly Ala Glu Ser Phe His Gln Ser Ser Gly
            180                 185                 190

Ile Leu Ser Arg Pro Pro Val Gly Ser Ser Leu Gln Ser Lys His Arg
            195                 200                 205

Lys Ser Arg Leu Gly Leu Gln Ser Gln Gln Gly His Leu Ala Arg Arg
    210                 215                 220

Gln Gln Gly Arg Ser Trp Ser Ile Arg Ala Gly Ile His Pro Thr Ala
225                 230                 235                 240

Arg Arg Ser Phe Gly Val Glu Pro Ser Gly Ser Gly His Ser Thr Asn
                245                 250                 255

Leu Ala Ser Lys Ser Ala Ser Cys Leu Tyr Gln Ser Pro Val Arg Lys
            260                 265                 270

Ala Ala Tyr Pro Ala Val Ser Thr Phe Glu Lys His Ser Ser Ser Gly
            275                 280                 285

His Ala Val Glu Leu His Asn Leu Pro Pro Asn Ser Ala Arg Ser Gln
            290                 295                 300

Ser Glu Arg Pro Val Phe Pro Cys Trp Trp Leu Gln Phe Arg Asn Ser
305                 310                 315                 320

Lys Pro Cys Ser Asp Tyr Cys Leu Ser His Ile Val Asn Leu Leu Glu
                325                 330                 335

Asp Trp Gly Pro Cys Ala Glu His Gly Glu His His Ile Arg Ile Pro
                340                 345                 350

Arg Thr Pro Ala Arg Val Thr Gly Gly Val Phe Leu Val Asp Lys Asn
            355                 360                 365

Pro His Asn Thr Ala Glu Ser Arg Leu Val Val Asp Phe Ser Gln Phe
    370                 375                 380

Ser Arg Gly Asn Tyr Arg Val Ser Trp Pro Lys Phe Ala Val Pro Asn
385                 390                 395                 400

Leu Gln Ser Leu Thr Asn Leu Leu Ser Ser Asn Leu Ser Trp Leu Ser
                405                 410                 415
```

```
Leu Asp Val Ser Ala Ala Phe Tyr His Leu Pro Leu His Pro Ala Ala
                420                 425                 430

Met Pro His Leu Leu Val Gly Ser Ser Gly Leu Ser Arg Tyr Val Ala
            435                 440                 445

Arg Leu Ser Ser Asn Ser Arg Ile Phe Asn Tyr Gln His Gly Thr Met
        450                 455                 460

Gln Asn Leu His Asp Ser Cys Ser Arg Asn Leu Tyr Val Ser Leu Leu
465                 470                 475                 480

Leu Leu Tyr Gln Thr Phe Gly Arg Lys Leu His Leu Tyr Ser His Pro
                485                 490                 495

Ile Ile Leu Gly Phe Arg Lys Ile Pro Met Gly Val Gly Leu Ser Pro
            500                 505                 510

Phe Leu Leu Ala Gln Phe Thr Ser Ala Ile Cys Ser Val Val Arg Arg
        515                 520                 525

Ala Phe Pro His Cys Leu Ala Phe Ser Tyr Met His Asp Val Val Leu
530                 535                 540

Gly Ala Lys Ser Val Gln His Leu Glu Ser Leu Phe Thr Ala Val Thr
545                 550                 555                 560

Asn Phe Leu Leu Ser Leu Gly Ile His Leu Asn Pro Asn Lys Thr Lys
                565                 570                 575

Arg Trp Gly Tyr Ser Leu His Phe Met Gly Tyr Val Ile Gly Cys Tyr
            580                 585                 590

Gly Ser Leu Pro Gln Asp His Ile Ile Gln Lys Ile Lys Glu Cys Phe
        595                 600                 605

Arg Lys Leu Pro Val Asn Arg Pro Ile Asp Trp Lys Val Cys Gln Arg
610                 615                 620

Ile Val Gly Leu Leu Gly Phe Ala Ala Pro Phe Thr Gln Cys Gly Tyr
625                 630                 635                 640

Pro Ala Leu Met Pro Leu Tyr Ala Cys Ile Gln Ser Lys Gln Ala Phe
                645                 650                 655

Thr Phe Ser Pro Thr Tyr Lys Ala Phe Leu Cys Lys Gln Tyr Leu Asn
            660                 665                 670

Leu Tyr Pro Val Ala Arg Gln Arg Pro Gly Leu Cys Gln Val Phe Ala
        675                 680                 685

Asp Ala Thr Pro Thr Gly Trp Gly Leu Val Met Gly His Gln Arg Met
690                 695                 700

Arg Gly Thr Phe Leu Ala Pro Leu Pro Ile His Thr Ala His Leu Leu
705                 710                 715                 720

Ala Ala Cys Phe Ala Arg Ser Arg Ser Gly Ala Asn Ile Leu Gly Thr
                725                 730                 735

Asp Asn Ser Val Val Leu Ser Arg Lys Tyr Thr Ser Phe Pro Trp Leu
            740                 745                 750

Leu Gly Cys Ala Ala Asn Trp Ile Leu Arg Gly Thr Ser Phe Val Tyr
        755                 760                 765

Val Pro Ser Ala Leu Asn Pro Thr Asp Pro Ser Arg Gly Arg Leu
770                 775                 780

Gly Leu Ser Arg Pro Leu Leu Arg Leu Pro Phe Arg Pro Thr Thr Gly
785                 790                 795                 800

Arg Thr Ser Leu Tyr Ala Asp Ser Pro Ser Val Pro Ser His Leu Pro
                805                 810                 815

Asp Arg Val His Phe Ala Ser Pro Leu His Val Ala Trp Arg Pro Pro
            820                 825                 830
```

```
<210> SEQ ID NO 9
<211> LENGTH: 874
<212> TYPE: PRT
<213> ORGANISM: artificial sequence
<220> FEATURE:
<223> OTHER INFORMATION: truncated and mutated HBV polymerase fused to
      the transmembrane domain of rabies glycoprotein (TMR)

<400> SEQUENCE: 9

Met Val Pro Gln Ala Leu Leu Phe Val Pro Leu Leu Val Phe Pro Leu
1               5                   10                  15

Cys Phe Gly Lys Phe Pro Ile Val Ser Ile Pro Trp Thr His Lys Val
                20                  25                  30

Gly Asn Phe Thr Gly Leu Tyr Ser Ser Thr Val Pro Val Phe Asn Pro
            35                  40                  45

His Trp Lys Thr Pro Ser Phe Pro Asn Ile His Leu His Gln Asp Ile
        50                  55                  60

Ile Lys Lys Cys Glu Gln Phe Val Gly Pro Leu Thr Val Asn Glu Lys
65                  70                  75                  80

Arg Arg Leu Gln Leu Ile Met Pro Ala Arg Phe Tyr Pro Asn Val Thr
                85                  90                  95

Lys Tyr Leu Pro Leu Asp Lys Gly Ile Lys Pro Tyr Tyr Pro Glu His
            100                 105                 110

Leu Val Asn His Tyr Phe Gln Thr Arg His Tyr Leu His Thr Leu Trp
        115                 120                 125

Lys Ala Gly Ile Leu Tyr Lys Arg Glu Thr Thr His Ser Ala Ser Phe
130                 135                 140

Cys Gly Ser Pro Tyr Ser Trp Glu Gln Lys Leu Gln His Gly Ala Glu
145                 150                 155                 160

Ser Phe His Gln Gln Ser Ser Gly Ile Leu Ser Arg Pro Pro Val Gly
                165                 170                 175

Ser Ser Leu Gln Ser Lys His Arg Lys Ser Arg Leu Gly Leu Gln Ser
            180                 185                 190

Gln Gln Gly His Leu Ala Arg Arg Gln Gln Gly Arg Ser Trp Ser Ile
        195                 200                 205

Arg Ala Gly Ile His Pro Thr Ala Arg Arg Ser Phe Gly Val Glu Pro
210                 215                 220

Ser Gly Ser Gly His Ser Thr Asn Leu Ala Ser Lys Ser Ala Ser Cys
225                 230                 235                 240

Leu Tyr Gln Ser Pro Val Arg Lys Ala Ala Tyr Pro Ala Val Ser Thr
                245                 250                 255

Phe Glu Lys His Ser Ser Ser Gly His Ala Val Glu Leu His Asn Leu
            260                 265                 270

Pro Pro Asn Ser Ala Arg Ser Gln Ser Glu Arg Pro Val Phe Pro Cys
        275                 280                 285

Trp Trp Leu Gln Phe Arg Asn Ser Lys Pro Cys Ser Asp Tyr Cys Leu
290                 295                 300

Ser His Ile Val Asn Leu Leu Glu Asp Trp Gly Pro Cys Ala Glu His
305                 310                 315                 320

Gly Glu His His Ile Arg Ile Pro Arg Thr Pro Ala Arg Val Thr Gly
                325                 330                 335

Gly Val Phe Leu Val Asp Lys Asn Pro His Asn Thr Ala Glu Ser Arg
            340                 345                 350

Leu Val Val Asp Phe Ser Gln Phe Ser Arg Gly Asn Tyr Arg Val Ser
        355                 360                 365
```

-continued

```
Trp Pro Lys Phe Ala Val Pro Asn Leu Gln Ser Leu Thr Asn Leu Leu
370                 375                 380

Ser Ser Asn Leu Ser Trp Leu Ser Leu Asp Val Ser Ala Ala Phe Tyr
385                 390                 395                 400

His Leu Pro Leu His Pro Ala Ala Met Pro His Leu Leu Val Gly Ser
                405                 410                 415

Ser Gly Leu Ser Arg Tyr Val Ala Arg Leu Ser Ser Asn Ser Arg Ile
            420                 425                 430

Phe Asn Tyr Gln His Gly Thr Met Gln Asn Leu His Asp Ser Cys Ser
        435                 440                 445

Arg Asn Leu Tyr Val Ser Leu Leu Leu Tyr Gln Thr Phe Gly Arg
450                 455                 460

Lys Leu His Leu Tyr Ser His Pro Ile Ile Leu Gly Phe Arg Lys Ile
465                 470                 475                 480

Pro Met Gly Val Gly Leu Ser Pro Phe Leu Leu Ala Gln Phe Thr Ser
                485                 490                 495

Ala Ile Cys Ser Val Val Arg Arg Ala Phe Pro His Cys Leu Ala Phe
            500                 505                 510

Ser Tyr Met His Asp Val Val Leu Gly Ala Lys Ser Val Gln His Leu
        515                 520                 525

Glu Ser Leu Phe Thr Ala Val Thr Asn Phe Leu Leu Ser Leu Gly Ile
530                 535                 540

His Leu Asn Pro Asn Lys Thr Lys Arg Trp Gly Tyr Ser Leu His Phe
545                 550                 555                 560

Met Gly Tyr Val Ile Gly Cys Tyr Gly Ser Leu Pro Gln Asp His Ile
                565                 570                 575

Ile Gln Lys Ile Lys Glu Cys Phe Arg Lys Leu Pro Val Asn Arg Pro
            580                 585                 590

Ile Asp Trp Lys Val Cys Gln Arg Ile Val Gly Leu Leu Gly Phe Ala
        595                 600                 605

Ala Pro Phe Thr Gln Cys Gly Tyr Pro Ala Leu Met Pro Leu Tyr Ala
610                 615                 620

Cys Ile Gln Ser Lys Gln Ala Phe Thr Phe Ser Pro Thr Tyr Lys Ala
625                 630                 635                 640

Phe Leu Cys Lys Gln Tyr Leu Asn Leu Tyr Pro Val Ala Arg Gln Arg
                645                 650                 655

Pro Gly Leu Cys Gln Val Phe Ala Asp Ala Thr Pro Thr Gly Trp Gly
            660                 665                 670

Leu Val Met Gly His Gln Arg Met Arg Gly Thr Phe Leu Ala Pro Leu
        675                 680                 685

Pro Ile His Thr Ala His Leu Leu Ala Ala Cys Phe Ala Arg Ser Arg
690                 695                 700

Ser Gly Ala Asn Ile Leu Gly Thr Asp Asn Ser Val Val Leu Ser Arg
705                 710                 715                 720

Lys Tyr Thr Ser Phe Pro Trp Leu Leu Gly Cys Ala Ala Asn Trp Ile
                725                 730                 735

Leu Arg Gly Thr Ser Phe Val Tyr Val Pro Ser Ala Leu Asn Pro Thr
            740                 745                 750

Asp Asp Pro Ser Arg Gly Arg Leu Gly Leu Ser Arg Pro Leu Leu Arg
        755                 760                 765

Leu Pro Phe Arg Pro Thr Thr Gly Arg Thr Ser Leu Tyr Ala Asp Ser
770                 775                 780

Pro Ser Val Pro Ser His Leu Pro Asp Arg Val His Phe Ala Ser Pro
```

```
                785                 790                 795                 800
Leu His Val Ala Trp Arg Pro Pro Tyr Val Leu Leu Ser Ala Gly Ala
                    805                 810                 815

Leu Thr Ala Leu Met Leu Ile Ile Phe Leu Met Thr Cys Cys Arg Arg
                820                 825                 830

Val Asn Arg Ser Glu Pro Thr Gln His Asn Leu Arg Gly Thr Gly Arg
                835                 840                 845

Glu Val Ser Val Thr Pro Gln Ser Gly Lys Ile Ile Ser Ser Trp Glu
            850                 855                 860

Ser His Lys Ser Gly Gly Glu Thr Arg Leu
865                 870

<210> SEQ ID NO 10
<211> LENGTH: 148
<212> TYPE: PRT
<213> ORGANISM: artificial sequence
<220> FEATURE:
<223> OTHER INFORMATION: truncated core (1-148)

<400> SEQUENCE: 10

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Gly Asn Leu Glu Asp Pro Ile
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
                100                 105                 110

Glu Thr Val Ile Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val
145

<210> SEQ ID NO 11
<211> LENGTH: 140
<212> TYPE: PRT
<213> ORGANISM: artificial sequence
<220> FEATURE:
<223> OTHER INFORMATION: truncated and deleted HBV core
     (1-76 and 85-148)

<400> SEQUENCE: 11

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60
```

```
Leu Met Thr Leu Ala Thr Trp Val Gly Gly Asn Leu Val Val Ser Tyr
 65                  70                  75                  80

Val Asn Thr Asn Met Gly Leu Lys Phe Arg Gln Leu Leu Trp Phe His
                 85                  90                  95

Ile Ser Cys Leu Thr Phe Gly Arg Glu Thr Val Ile Glu Tyr Leu Val
            100                 105                 110

Ser Phe Gly Val Trp Ile Arg Thr Pro Pro Ala Tyr Arg Pro Pro Asn
        115                 120                 125

Ala Pro Ile Leu Ser Thr Leu Pro Glu Thr Thr Val
    130                 135                 140

<210> SEQ ID NO 12
<211> LENGTH: 39
<212> TYPE: PRT
<213> ORGANISM: artificial sequence
<220> FEATURE:
<223> OTHER INFORMATION: HBV immunogenic domain Env1 (14-51)

<400> SEQUENCE: 12

Met Val Leu Gln Ala Gly Phe Phe Leu Leu Thr Arg Ile Leu Thr Ile
  1               5                  10                  15

Pro Gln Ser Leu Asp Ser Trp Trp Thr Ser Leu Asn Phe Leu Gly Gly
             20                  25                  30

Thr Thr Val Cys Leu Gly Gln
         35

<210> SEQ ID NO 13
<211> LENGTH: 30
<212> TYPE: PRT
<213> ORGANISM: artificial sequence
<220> FEATURE:
<223> OTHER INFORMATION: HBV immungenic domain Env2 (165-194)

<400> SEQUENCE: 13

Trp Ala Ser Ala Arg Phe Ser Trp Leu Ser Leu Leu Val Pro Phe Val
  1               5                  10                  15

Gln Trp Phe Val Gly Leu Ser Pro Thr Val Trp Leu Ser Val
             20                  25                  30

<210> SEQ ID NO 14
<211> LENGTH: 26
<212> TYPE: PRT
<213> ORGANISM: artificial sequence
<220> FEATURE:
<223> OTHER INFORMATION: HBV immunogenic domain Env 3 (81-106)

<400> SEQUENCE: 14

Ile Ile Phe Leu Phe Ile Leu Leu Leu Cys Leu Ile Phe Leu Leu Val
  1               5                  10                  15

Leu Leu Asp Tyr Gln Gly Met Leu Pro Val
             20                  25

<210> SEQ ID NO 15
<211> LENGTH: 25
<212> TYPE: PRT
<213> ORGANISM: artificial sequence
<220> FEATURE:
<223> OTHER INFORMATION: HBV immunogenic domain Env 4 (202-226)

<400> SEQUENCE: 15

Gly Pro Ser Leu Tyr Ser Ile Leu Ser Pro Phe Leu Pro Leu Leu Pro
  1               5                  10                  15
```

```
Ile Phe Phe Cys Leu Trp Val Tyr Ile
            20              25
```

<210> SEQ ID NO 16
<211> LENGTH: 69
<212> TYPE: PRT
<213> ORGANISM: artificial sequence
<220> FEATURE:
<223> OTHER INFORMATION: fusion of HBV immunogenic domains Env1-Env2

<400> SEQUENCE: 16

```
Met Val Leu Gln Ala Gly Phe Phe Leu Leu Thr Arg Ile Leu Thr Ile
1               5                   10                  15

Pro Gln Ser Leu Asp Ser Trp Trp Thr Ser Leu Asn Phe Leu Gly Gly
            20                  25                  30

Thr Thr Val Cys Leu Gly Gln Trp Ala Ser Ala Arg Phe Ser Trp Leu
        35                  40                  45

Ser Leu Leu Val Pro Phe Val Gln Trp Phe Val Gly Leu Ser Pro Thr
    50                  55                  60

Val Trp Leu Ser Val
65
```

<210> SEQ ID NO 17
<211> LENGTH: 94
<212> TYPE: PRT
<213> ORGANISM: artificial sequences
<220> FEATURE:
<223> OTHER INFORMATION: fusion of HBV immunogenic
      domains Env1-Env2-Env4

<400> SEQUENCE: 17

```
Met Val Leu Gln Ala Gly Phe Phe Leu Leu Thr Arg Ile Leu Thr Ile
1               5                   10                  15

Pro Gln Ser Leu Asp Ser Trp Trp Thr Ser Leu Asn Phe Leu Gly Gly
            20                  25                  30

Thr Thr Val Cys Leu Gly Gln Trp Ala Ser Ala Arg Phe Ser Trp Leu
        35                  40                  45

Ser Leu Leu Val Pro Phe Val Gln Trp Phe Val Gly Leu Ser Pro Thr
    50                  55                  60

Val Trp Leu Ser Val Gly Pro Ser Leu Tyr Ser Ile Leu Ser Pro Phe
65                  70                  75                  80

Leu Pro Leu Leu Pro Ile Phe Phe Cys Leu Trp Val Tyr Ile
                85                  90
```

<210> SEQ ID NO 18
<211> LENGTH: 179
<212> TYPE: PRT
<213> ORGANISM: artificial sequence
<220> FEATURE:
<223> OTHER INFORMATION: fusion of truncated and deleted core
      (1-76 85-148) with HBV immunogenic domain Env 1

<400> SEQUENCE: 18

```
Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
```

```
                    50                  55                  60
Leu Met Thr Leu Ala Thr Trp Val Gly Gly Asn Leu Val Val Ser Tyr
 65                  70                  75                  80

Val Asn Thr Asn Met Gly Leu Lys Phe Arg Gln Leu Leu Trp Phe His
                 85                  90                  95

Ile Ser Cys Leu Thr Phe Gly Arg Glu Thr Val Ile Glu Tyr Leu Val
            100                 105                 110

Ser Phe Gly Val Trp Ile Arg Thr Pro Pro Ala Tyr Arg Pro Pro Asn
        115                 120                 125

Ala Pro Ile Leu Ser Thr Leu Pro Glu Thr Thr Val Met Val Leu Gln
        130                 135                 140

Ala Gly Phe Phe Leu Leu Thr Arg Ile Leu Thr Ile Pro Gln Ser Leu
145                 150                 155                 160

Asp Ser Trp Trp Thr Ser Leu Asn Phe Leu Gly Gly Thr Thr Val Cys
                165                 170                 175

Leu Gly Gln

<210> SEQ ID NO 19
<211> LENGTH: 208
<212> TYPE: PRT
<213> ORGANISM: artificial sequence
<220> FEATURE:
<223> OTHER INFORMATION: fusion of truncated and deleted core
      (1-76 85-148) with HBV immunogenic domains Env1 and Env2

<400> SEQUENCE: 19

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Gly Asn Leu Val Val Ser Tyr
 65                  70                  75                  80

Val Asn Thr Asn Met Gly Leu Lys Phe Arg Gln Leu Leu Trp Phe His
                 85                  90                  95

Ile Ser Cys Leu Thr Phe Gly Arg Glu Thr Val Ile Glu Tyr Leu Val
            100                 105                 110

Ser Phe Gly Val Trp Ile Arg Thr Pro Pro Ala Tyr Arg Pro Pro Asn
        115                 120                 125

Ala Pro Ile Leu Ser Thr Leu Pro Glu Thr Thr Val Val Leu Gln Ala
        130                 135                 140

Gly Phe Phe Leu Leu Thr Arg Ile Leu Thr Ile Pro Gln Ser Leu Asp
145                 150                 155                 160

Ser Trp Trp Thr Ser Leu Asn Phe Leu Gly Gly Thr Thr Val Cys Leu
                165                 170                 175

Gly Gln Trp Ala Ser Ala Arg Phe Ser Trp Leu Ser Leu Leu Val Pro
            180                 185                 190

Phe Val Gln Trp Phe Val Gly Leu Ser Pro Thr Val Trp Leu Ser Val
        195                 200                 205

<210> SEQ ID NO 20
<211> LENGTH: 276
<212> TYPE: PRT
```

<213> ORGANISM: artificial sequence
<220> FEATURE:
<223> OTHER INFORMATION: fusion of core with HBV immunogenic domains Env1, Env2 and Env4

<400> SEQUENCE: 20

```
Met Asp Ile Asp Pro Tyr Lys Glu Phe Gly Ala Thr Val Glu Leu Leu
1               5                   10                  15
Ser Phe Leu Pro Ser Asp Phe Phe Pro Ser Val Arg Asp Leu Leu Asp
            20                  25                  30
Thr Ala Ser Ala Leu Tyr Arg Glu Ala Leu Glu Ser Pro Glu His Cys
        35                  40                  45
Ser Pro His His Thr Ala Leu Arg Gln Ala Ile Leu Cys Trp Gly Glu
    50                  55                  60
Leu Met Thr Leu Ala Thr Trp Val Gly Gly Asn Leu Glu Asp Pro Ile
65                  70                  75                  80
Ser Arg Asp Leu Val Val Ser Tyr Val Asn Thr Asn Met Gly Leu Lys
                85                  90                  95
Phe Arg Gln Leu Leu Trp Phe His Ile Ser Cys Leu Thr Phe Gly Arg
            100                 105                 110
Glu Thr Val Ile Glu Tyr Leu Val Ser Phe Gly Val Trp Ile Arg Thr
        115                 120                 125
Pro Pro Ala Tyr Arg Pro Pro Asn Ala Pro Ile Leu Ser Thr Leu Pro
    130                 135                 140
Glu Thr Thr Val Val Arg Arg Arg Gly Arg Ser Pro Arg Arg Arg Thr
145                 150                 155                 160
Pro Ser Pro Arg Arg Arg Arg Ser Gln Ser Pro Arg Arg Arg Arg Ser
                165                 170                 175
Gln Ser Arg Glu Ser Gln Cys Val Leu Gln Ala Gly Phe Phe Leu Leu
            180                 185                 190
Thr Arg Ile Leu Thr Ile Pro Gln Ser Leu Asp Ser Trp Trp Thr Ser
        195                 200                 205
Leu Asn Phe Leu Gly Gly Thr Thr Val Cys Leu Gly Gln Trp Ala Ser
    210                 215                 220
Ala Arg Phe Ser Trp Leu Ser Leu Leu Val Pro Phe Val Gln Trp Phe
225                 230                 235                 240
Val Gly Leu Ser Pro Thr Val Trp Leu Ser Val Gly Pro Ser Leu Tyr
                245                 250                 255
Ser Ile Leu Ser Pro Phe Leu Pro Leu Leu Pro Ile Phe Phe Cys Leu
            260                 265                 270
Trp Val Tyr Ile
        275
```

<210> SEQ ID NO 21
<211> LENGTH: 2361
<212> TYPE: DNA
<213> ORGANISM: artificial sequence
<220> FEATURE:
<223> OTHER INFORMATION: nucleotide sequence encoding HBV truncated polymerase (48-832)

<400> SEQUENCE: 21

```
atggttagta ttccttggac tcataaggtg ggaaacttta cggggcttta ttcttctact    60
gtacctgtct ttaaccctca ttggaaaaca ccctcttttc ctaatataca tttacaccaa   120
gacattatca aaaatgtgaa caatttgtag gcccactca cagtcaatga aaaagaaga   180 ctgcaattga ttatgcctgc taggttttat ccaaatgtta ccaaatattt gccattggat   240
```

```
aagggtatta aaccttatta tccagaacat ctagttaatc attacttcca aaccagacat   300
tatttacaca ctctatggaa ggcgggtata ttatataaga gagaaacaac acatagtgcc   360
tcattttgtg ggtcaccata ttcttgggaa caaaagctac agcatggggc agaatctttc   420
caccagcaat cctctgggat tctttcccga ccaccagttg gatccagcct tcagagcaaa   480
caccgcaaat ccagattggg acttcaatcc caacaaggac acctggccag acgccaacaa   540
ggtaggagct ggagcattcg ggctgggatt caccccaccg cacggaggtc ttttggggtg   600
gagccctcag gctcagggca ttctacaaac cttgccagca aatccgcctc ctgcctctac   660
caatcgccaa tcaggaaggc agcctacccc gctgtctcca cctttgagaa acactcatcc   720
tcaggccatg cagtggaact ccacaacctt ccaccaaact ctgcaagatc ccagagtgag   780
aggcctgtat ttccctgctg gtggctccag ttcaggaaca gtaaacctg ttccgactac    840
tgtctctccc atatcgtcaa tcttctcgag gattgggac cctgcgctga acatggagaa    900
catcacatca ggattcctag accctgct cgtgttacag gcggggtttt tcttgttgac     960
aagaatcctc acaataccgc agagtctaga ctcgtggtgg acttctctca attttctagg  1020
gggaactacc gtgtgtcttg gccaaaattc gcagtcccca acctccaatc actcaccaac  1080
ctcctgtcct ccaacctgtc ctggttatcg ctggatgtgt ctgcggcgtt ttatcatctt  1140
cctcttcatc ctgctgctat gcctcatctt cttgttggtt cttctggact atcaaggtat  1200
gttgcccgtt tgtcctctaa ttccaggatc ttcaactacc agcacgggac catgcagaac  1260
ctgcacgact cctgctcaag gaacctctat gtatccctcc tgttgctgta ccaaaccttc  1320
ggacggaaat tgcacctgta ttcccatccc atcatcctgg gctttcggaa aattcctatg  1380
ggagtggggcc tcagcccgtt tctcctggct cagtttacta gtgccatttg ttcagtggtt  1440
cgtagggctt tcccccactg tttggctttc agttatatgg atgatgtggt attggggcc   1500
aagtctgtac agcatcttga gtcccttttt accgctgtta ccaatttct tttgtctttg   1560
ggtatacatt taaaccctaa caaaacaaaa agatgggtt actctttaca tttcatgggc   1620
tatgtcattg gatgttatgg gtcattgcca caagatcaca tcatacaaaa aatcaaagaa   1680
tgttttcgaa aacttcctgt taacagacct attgattgga aagtctgtca acgtattgtg   1740
ggtcttttgg gttttgctgc cccttttaca caatgtggtt atcctgcttt aatgcctttg   1800
tatgcatgta ttcagtcgaa gcaggctttt actttctcgc caacttacaa ggcctttctg   1860
tgtaaacaat acctgaacct ttaccccgtt gcccggcaac ggccaggtct gtgccaagtg   1920
tttgctgacg caaccccac tggctggggc ttggtcatgg ccatcagcg catgcgtgga     1980
acctttctgg ctcctctgcc gatccatact gcggaactcc tagccgcttg ttttgctcgc   2040
agcaggtctg gagcaaacat tctcgggacg gataactctg ttgttctctc ccgcaaatat   2100
acatcgtttc catggctgct aggctgtgct gccaactgga tcctgcgcgg acgtcctt     2160
gtttacgtcc cgtcggcgct gaatcccacg gacgacccct tcggggtcg cttgggctc     2220
tctcgtcccc ttctccgtct accgtttcga ccgaccacgg ggcgcacctc tctttacgcg   2280
gactccccgt ctgtgccttc tcatctgccg gaccgtgtgc acttcgcttc acctctgcac   2340
gtcgcatgga gaccaccgtg a                                              2361
```

<210> SEQ ID NO 22
<211> LENGTH: 2499
<212> TYPE: DNA
<213> ORGANISM: artificial sequence
<220> FEATURE:

<223> OTHER INFORMATION: nucleotide sequence encoding a mutated HBV polymerase deficient for RTase and RNase activities

<400> SEQUENCE: 22

```
atgcccctat cttatcaaca cttccggaga ctactgttgt tagacgacga ggcaggtccc     60
ctagaagaag aactccctcg cctcgcagac gaaggtctca atcgccgcgt cgcagaagat    120
ctcaatctcg ggaatctcaa tgttagtatt ccttggactc ataaggtggg aaactttacg    180
gggctttatt cttctactgt acctgtcttt aaccctcatt ggaaaacacc ctcttttcct    240
aatatacatt tacaccaaga cattatcaaa aaatgtgaac aatttgtagg cccactcaca    300
gtcaatgaga aaagaagact gcaattgatt atgcctgcta ggttttatcc aaatgttacc    360
aaatatttgc cattggataa gggtattaaa ccttattatc cagaacatct agttaatcat    420
tacttccaaa ccagacatta tttacacact ctatggaagg cgggtatatt atataagaga    480
gaaacaacac atagtgcctc attttgtggg tcaccatatt cttgggaaca aaagctacag    540
catggggcag aatctttcca ccagcaatcc tctgggattc tttcccgacc accagttgga    600
tccagccttc agagcaaaca ccgcaaatcc agattgggac ttcaatccca acaaggacac    660
ctggccagac gccaacaagg taggagctgg agcattcggg ctgggattca ccccaccgca    720
cggaggtctt ttggggtgga gccctcaggc tcagggcatt ctacaaacct tgccagcaaa    780
tccgcctcct gcctctacca atcgccagtc aggaaggcag cctaccccgc tgtctccacc    840
tttgagaaac actcatcctc aggccatgca gtggaactcc acaaccttcc accaaactct    900
gcaagatccc agagtgagag gcctgtattt ccctgctggt ggctccagtt caggaacagt    960
aaaccctgtt ccgactactg tctctcccat atcgtcaatc ttctcgagga ttggggaccc   1020
tgcgctgaac atggagaaca tcacatcagg attcctagga cccctgctcg tgttacaggc   1080
ggggtttttc ttgttgacaa gaatcctcac aataccgcag agtctagact cgtggtggac   1140
ttctctcaat ttctaggggg aactaccgt gtgtcttggc caaaattcgc agtccccaac    1200
ctccaatcac tcaccaacct cctgtcctcc aacctgtcct ggttatcgct ggatgtgtct   1260
gcggcgtttt atcatcttcc tcttcatcct gctgctatgc ctcatcttct tgttggttct   1320
tctggactat caaggtatgt tgcccgtttg tcctctaatt ccaggatctt caactaccag   1380
cacgggacca tgcagaacct gcacgactcc tgctcaagga acctctatgt atccctcctg   1440
ttgctgtacc aaaccttcgg acggaaattg cacctgtatt cccatcccat catcctgggc   1500
tttcggaaaa ttcctatggg agtgggcctc agcccgtttc tcctggctca gtttactagt   1560
gccatttgtt cagtggttcg tagggctttc ccccactgtt tggctttcag ttatatgcat   1620
gatgtggtat tgggggccaa gtctgtacag catcttgagt ccctttttac cgctgttacc   1680
aattttcttt tgtctttggg tatacattta aaccctaaca aaacaaaaag atggggttac   1740
tctttacatt tcatgggcta tgtcattgga tgttatgggt cattgccaca agatcacatc   1800
atacaaaaaa tcaaagaatg ttttcgaaaa cttcctgtta acagacctat tgattggaaa   1860
gtctgtcaac gtattgtggg tcttttgggt tttgctgccc cttttacaca atgtggttat   1920
cctgctttaa tgcctttgta tgcatgtatt cagtcgaagc aggcttttac tttctcgcca   1980
acttacaagg cctttctgtg taaacaatac ctgaaccttt accccgttgc ccggcaacgg   2040
ccaggtctgt gccaagtgtt tgctgacgca acccccactg gctggggctt ggtcatgggc   2100
catcagcgca tgcgtggaac ctttctggct cctctgccga tccatactgc gcatctccta   2160
gccgcttgtt ttgctcgcag caggtctgga gcaaacattc tcgggacgga taactctgtt   2220
```

| | |
|---|---|
| gttctctccc gcaaatatac atcgtttcca tggctgctag gctgtgctgc caactggatc | 2280 |
| ctgcgcggga cgtcctttgt ttacgtcccg tcggcgctga atcccacgga cgacccttct | 2340 |
| cggggtcgct tggggctctc tcgtcccctt ctccgtctac cgtttcgacc gaccacgggg | 2400 |
| cgcacctctc tttacgcgga ctccccgtct gtgccttctc atctgccgga ccgtgtgcac | 2460 |
| ttcgcttcac ctctgcacgt cgcatggaga ccaccgtga | 2499 |

<210> SEQ ID NO 23
<211> LENGTH: 2628
<212> TYPE: DNA
<213> ORGANISM: artificial sequence
<220> FEATURE:
<223> OTHER INFORMATION: nucleotide sequence encoding HBV truncated and
      mutated Pol fused to the transmembrane domain of the rabies
      glycoprotein (TMR)

<400> SEQUENCE: 23

| | |
|---|---|
| atggttcctc aggctctcct gtttgtaccc cttctggttt ttccattgtg ttttgggaaa | 60 |
| ttccctattg ttagtattcc ttggactcat aaggtgggaa actttacggg gctttattct | 120 |
| tctactgtac ctgtctttaa ccctcattgg aaaacaccct cttttcctaa tatacattta | 180 |
| caccaagaca ttatcaaaaa atgtgaacaa tttgtaggcc cactcacagt caatgagaaa | 240 |
| agaagactgc aattgattat gcctgctagg ttttatccaa atgttaccaa atatttgcca | 300 |
| ttggataagg gtattaaacc ttattatcca gaacatctag ttaatcatta cttccaaacc | 360 |
| agacattatt tacacactct atggaaggcg ggtatattat ataagagaga acaacacat | 420 |
| agtgcctcat tttgtgggtc accatattct tgggaacaaa agctacagca tggggcagaa | 480 |
| tctttccacc agcaatcctc tgggattctt tcccgaccac cagttggatc cagccttcag | 540 |
| agcaaacacc gcaaatccag attgggactt caatcccaac aaggacacct ggccagacgc | 600 |
| caacaaggta ggagctggag cattcgggct gggattcacc ccaccgcacg gaggtctttt | 660 |
| ggggtggagc cctcaggctc agggcattct acaaaccttg ccagcaaatc cgcctcctgc | 720 |
| ctctaccaat cgccagtcag gaaggcagcc taccccgctg tctccacctt tgagaaacac | 780 |
| tcatcctcag gccatgcagt ggaactccac aaccttccac aaactctgc aagatcccag | 840 |
| agtgagaggc ctgtatttcc ctgctggtgg ctccagttca ggaacagtaa accctgttcc | 900 |
| gactactgtc tctcccatat cgtcaatctt ctcgaggatt ggggaccctg cgctgaacat | 960 |
| ggagaacatc acatcaggat tcctaggacc cctgctcgtg ttacaggcgg gttttctt | 1020 |
| gttgacaaga atcctcacaa taccgcagag tctagactcg tggtggactt ctctcaattt | 1080 |
| tctaggggga actaccgtgt gtcttggcca aaattcgcag tccccaacct ccaatcactc | 1140 |
| accaacctcc tgtcctccaa cctgtcctgg ttatcgctgg atgtgtctgc ggcgttttat | 1200 |
| catcttcctc ttcatcctgc tgctatgcct catcttcttg ttggttcttc tggactatca | 1260 |
| aggtatgttg cccgtttgtc ctctaattcc aggatcttca actaccagca cgggaccatg | 1320 |
| cagaacctgc acgactcctg ctcaaggaac ctctatgtat ccctcctgtt gctgtaccaa | 1380 |
| accttcggac ggaaattgca cctgtattcc catcccatca tcctgggctt tcggaaaatt | 1440 |
| cctatgggag tgggcctcag cccgtttctc ctggctcagt ttactagtgc catttgttca | 1500 |
| gtggttcgta gggctttccc ccactgtttg gctttcagtt atatgcatga tgtggtattg | 1560 |
| ggggccaagt ctgtacagca tcttgagtcc cttttaccg ctgttaccaa ttttctttg | 1620 |
| tctttgggta tacatttaaa ccctaacaaa acaaaaagat ggggttactc tttacatttc | 1680 |
| atgggctatg tcattggatg ttatgggtca ttgccacaag atcacatcat acaaaaaatc | 1740 |

```
aaagaatgtt ttcgaaaact tcctgttaac agacctattg attggaaagt ctgtcaacgt    1800
attgtgggtc ttttgggttt tgctgccect tttacacaat gtggttatcc tgctttaatg    1860
cctttgtatg catgtattca gtcgaagcag gcttttactt tctcgccaac ttacaaggcc    1920
tttctgtgta aacaatacct gaacctttac cccgttgccc ggcaacggcc aggtctgtgc    1980
caagtgtttg ctgacgcaac ccccactggc tggggcttgg tcatgggcca tcagcgcatg    2040
cgtggaacct ttctggctcc tctgccgatc catactgcgc atctcctagc cgcttgtttt    2100
gctcgcagca ggtctggagc aaacattctc gggacggata actctgttgt tctctcccgc    2160
aaatatacat cgtttccatg gctgctaggc tgtgctgcca actggatcct gcgcgggacg    2220
tcctttgttt acgtcccgtc ggcgctgaat cccacggacg acccttctcg gggtcgcttg    2280
gggctctctc gtccccttct ccgtctaccg tttcgaccga ccacggggcg cacctctctt    2340
tacgcggact ccccgtctgt gccttctcat ctgccggacc gtgtgcactt cgcttcacct    2400
ctgcacgtcg catggagacc accgtatgta ttactgagtg caggggccct gactgccttg    2460
atgttgataa ttttcctgat gacatgttgt agaagagtca atcgatcaga acctacgcaa    2520
cacaatctca gagggacagg gagggaggtg tcagtcactc cccaaagcgg gaagatcata    2580
tcttcatggg aatcacacaa gagtgggggt gagaccagac tgtgatga              2628

<210> SEQ ID NO 24
<211> LENGTH: 537
<212> TYPE: DNA
<213> ORGANISM: artificial sequence
<220> FEATURE:
<223> OTHER INFORMATION: nucleotide sequence encoding the HBV truncated
      and deleted core (1-76 85-148) fused to HBV immunogenic domain Env
      1

<400> SEQUENCE: 24
atggacattg atccttataa agaatttgga gctactgtgg agttactctc ttttttgcct     60
tctgacttct ttccttcagt acgtgatctt ctagataccg cctcagctct gtatcgggaa    120
gccttagagt ctcctgagca ttgttcacct caccatactg ctctcaggca agcaattctg    180
tgctgggggg aactaatgac tctagctacc tgggtgggtg gtaatttgga agtcagttat    240
gtcaacacta atatgggcct aaagttccgg caactattgt ggtttcacat ttcttgtctc    300
acttttggaa gagaaacagt tatagaatat ttggtgtctt tcggagtgtg gattcgcact    360
cctccagctt atagaccacc aaatgccccct atcttatcaa cacttccgga gactactgtt    420
gtcctgcaag caggcttctt cctgctgacc cgtattctga ccattccaca aagcctggat    480
agctggtgga ccagcctgaa cttcctgggt ggcaccacgg tttgcctggg tcagtaa      537

<210> SEQ ID NO 25
<211> LENGTH: 627
<212> TYPE: DNA
<213> ORGANISM: artificial sequence
<220> FEATURE:
<223> OTHER INFORMATION: nucleotide sequence encoding the HBV truncated
      and deleted core (1-76 85-148) fused with HBV immunogenic domains
      Env1 and Env2

<400> SEQUENCE: 25
atggacattg atccttataa agaatttgga gctactgtgg agttactctc ttttttgcct     60
tctgacttct ttccttcagt acgtgatctt ctagataccg cctcagctct gtatcgggaa    120
gccttagagt ctcctgagca ttgttcacct caccatactg ctctcaggca agcaattctg    180
```

```
tgctgggggg aactaatgac tctagctacc tgggtgggtg gtaatttgga agtcagttat    240
gtcaacacta atatgggcct aaagttccgg caactattgt ggtttcacat ttcttgtctc    300
acttttggaa gagaaacagt tatagaatat ttggtgtctt tcggagtgtg gattcgcact    360
cctccagctt atagaccacc aaatgcccct atcttatcaa cacttccgga gactactgtt    420
gtcctgcaag caggcttctt cctgctgacc cgtattctga ccattccaca aagcctggat    480
agctggtgga ccagcctgaa cttcctgggt ggcaccacgg tttgcctggg tcagtgggca    540
agcgcacgct ttagctggct gagcctgctg gttccgttcg tgcaatggtt tgtgggtctg    600
agcccaaccg tgtggctgag cgtgtaa                                       627
```

```
<210> SEQ ID NO 26
<211> LENGTH: 828
<212> TYPE: DNA
<213> ORGANISM: artificial sequence
<220> FEATURE:
<223> OTHER INFORMATION: nucleotide sequence encoding HBV core (1-183)
      fused to HBV immunogenic domains Env1-Env2 and Env4

<400> SEQUENCE: 26
```

```
atggacattg atccttataa agaatttgga gctactgtgg agttactctc tttttttgcct   60 tctgacttct ttccttcagt acgtgatctt ctagataccg cctcagctct gtatcgggaa   120
gccttagagt ctcctgagca ttgttcacct caccatactg ctctcaggca agcaattctg   180
tgctgggggg aactaatgac tctagctacc tgggtgggtg gtaatttgga agatccaata   240
tccagggacc tagtagtcag ttatgtcaac actaatatgg gcctaaagtt ccggcaacta   300
ttgtggtttc acatttcttg tctcactttt ggaagagaaa cagttataga atatttggtg   360
tctttcggag tgtggattcg cactcctcca gcttatagac accaaatgc cctatctta   420 tcaacacttc cggagactac tgttgttaga cgacgaggca ggtcccctag aagaagaact   480
ccctcgcctc gcagacgaag gtctcaatcg ccgtcgca aagatctca atctcgggaa     540 tctcagtgcg tcctgcaagc tggattcttt cttctcacca ggattttgac cattccacaa   600
tctcttgata gctggtggac aagtttgaac ttccttggag gcacaactgt ctgcctcgga   660
cagtgggcaa gtgctcgctt tcttggttg agcttgctcg ttcccttcgt gcaatggttt   720
gttggactct ctccaacagt ctggttgtcc gtcggaccta gcctttatag tattctcagc   780
ccattcttgc cactcttgcc tatcttcttc tgcttgtggg tttatatc                828
```

```
<210> SEQ ID NO 27
<211> LENGTH: 2499
<212> TYPE: DNA
<213> ORGANISM: artificial sequence
<220> FEATURE:
<223> OTHER INFORMATION: nucleotide sequence present in the plasmid
      pGA-15pol

<400> SEQUENCE: 27
```

```
atgcccctat cttatcaaca cttccggaga ctactgttgt tagacgacga ggcaggtccc    60
ctagaagaag aactccctcg cctcgcagac gaaggtctca atcgccgcgt cgcagaagat   120
ctcaatctcg ggaatctcaa tgttagtatt ccttggactc ataaggtggg aaactttacg   180
gggctttatt cttctactgt acctgtcttt aaccctcatt ggaaaacacc ctcttttcct   240
aatatacatt tacaccaaga cattatcaaa aatgtgaac aatttgtagg cccactcaca   300
gtcaatgaga aaagaagact gcaattgatt atgcctgcta ggttttatcc aaatgttacc   360
aaatatttgc cattggataa gggtattaaa ccttattatc cagaacatct agttaatcat   420
```

```
tacttccaaa ccagacatta tttacacact ctatggaagg cgggtatatt atataagaga    480
gaaacaacac atagtgcctc attttgtggg tcaccatatt cttgggaaca aaagctacag    540
catggggcag aatcttcca ccagcaatcc tctgggattc tttcccgacc accagttgga    600
tccagccttc agagcaaaca ccgcaaatcc agattgggac ttcaatccca acaaggacac    660
ctggccagac gccaacaagg taggagctgg agcattcggg ctgggattca ccccaccgca    720
cggaggtctt ttggggtgga gccctcaggc tcagggcatt ctacaaacct tgccagcaaa    780
tccgcctcct gcctctacca atcgccagtc aggaaggcag cctaccccgc tgtctccacc    840
tttgagaaac actcatcctc aggccatgca gtggaactcc acaaccttcc accaaactct    900
gcaagatccc agagtgagag gcctgtattt ccctgctggt ggctccagtt caggaacagt    960
aaaccctgtt ccgactactg tctctcccat atcgtcaatc ttctcgagga ttggggaccc   1020
tgcgctgaac atggagaaca tcacatcagg attcctagga cccctgctcg tgttacaggc   1080 ggggttttc ttgttgacaa gaatcctcac aataccgcag agtctagact cgtggtggac   1140
ttctctcaat tttctagggg gaactaccgt gtgtcttggc caaaattcgc agtccccaac   1200
ctccaatcac tcaccaacct cctgtcctcc aacctgtcct ggttatcgct ggatgtgtct   1260
gcggcgtttt atcatcttcc tcttcatcct gctgctatgc ctcatcttct tgttggttct   1320
tctggactat caaggtatgt tgcccgtttg tcctctaatt ccaggatctt caactaccag   1380
cacgggacca tgcagaacct gcacgactcc tgctcaagga acctctatgt atccctcctg   1440
ttgctgtacc aaaccttcgg acggaaattg cacctgtatt cccatcccat catcctgggc   1500
tttcggaaaa ttcctatggg agtgggcctc agcccgtttc tcctggctca gtttactagt   1560
gccatttgtt cagtggttcg tagggctttc ccccactgtt tggctttcag ttatatgcat   1620
gatgtggtat tgggggccaa gtctgtacag catcttgagt ccctttttac cgctgttacc   1680
aattttcttt tgtctttggg tatacattta aaccctaaca aaacaaaaag atggggttac   1740
tctttacatt tcatgggcta tgtcattgga tgttatgggt cattgccaca agatcacatc   1800
atacaaaaaa tcaaagaatg ttttcgaaaa cttcctgtta acagacctat tgattggaaa   1860
gtctgtcaac gtattgtggg tcttttgggt tttgctgccc cttttacaca atgtggttat   1920
cctgctttaa tgcctttgta tgcatgtatt cagtcgaagc aggcttttac tttctcgcca   1980
acttacaagg cctttctgtg taaacaatac ctgaaccttt accccgttgc ccggcaacgg   2040
ccaggtctgt gccaagtgtt tgctgacgca accccactg gctggggctt ggtcatgggc   2100
catcagcgca tgcgtggaac cttctctggct cctctgccga tccatactgc gcatctccta   2160
gccgcttgtt ttgctcgcag caggtctgga gcaaacattc tcgggacgga taactctgtt   2220
gttctctccc gcaaatatac atcgtttcca tggctgctag gctgtgctgc caactggatc   2280
ctgcgcggga cgtcctttgt ttacgtcccg tcggcgctga atcccacgga cgaccttct   2340 cggggtcgct tggggctctc tcgtcccctt tccgtctac cgtttcgacc gaccacgggg   2400
cgcacctctc tttacgcgga ctccccgtct gtgccttctc atctgccgga ccgtgtgcac   2460
ttcgcttcac ctctgcacgt cgcatggaga ccaccgtga                          2499
```

<210> SEQ ID NO 28
<211> LENGTH: 37
<212> TYPE: DNA
<213> ORGANISM: artificial sequence
<220> FEATURE:
<223> OTHER INFORMATION: primer

<400> SEQUENCE: 28
gagcgatatc caccatgaat gttagtattc cttggac   37

<210> SEQ ID NO 29
<211> LENGTH: 31
<212> TYPE: DNA
<213> ORGANISM: artificial sequence
<220> FEATURE:
<223> OTHER INFORMATION: primer

<400> SEQUENCE: 29
gatcgctagc tcacggtggt ctccatgcga c   31

<210> SEQ ID NO 30
<211> LENGTH: 35
<212> TYPE: DNA
<213> ORGANISM: artificial sequence
<220> FEATURE:
<223> OTHER INFORMATION: primer

<400> SEQUENCE: 30
gagtgatatc caccatggtt cctcaggctc tcctg   35

<210> SEQ ID NO 31
<211> LENGTH: 46
<212> TYPE: DNA
<213> ORGANISM: artificial sequence
<220> FEATURE:
<223> OTHER INFORMATION: primer

<400> SEQUENCE: 31
gtccaaggaa tactaacatt aatagggaat tccccaaaac acaatg   46

<210> SEQ ID NO 32
<211> LENGTH: 39
<212> TYPE: DNA
<213> ORGANISM: artificial sequence
<220> FEATURE:
<223> OTHER INFORMATION: primer

<400> SEQUENCE: 32
gtcgcatgga gaccaccgta tgtattactg agtgcaggg   39

<210> SEQ ID NO 33
<211> LENGTH: 29
<212> TYPE: DNA
<213> ORGANISM: artificial sequence
<220> FEATURE:
<223> OTHER INFORMATION: primer

<400> SEQUENCE: 33
gagtgctagc tcacagtctg gtctcaccc   29

<210> SEQ ID NO 34
<211> LENGTH: 42
<212> TYPE: DNA
<213> ORGANISM: artificial sequence
<220> FEATURE:
<223> OTHER INFORMATION: primer

<400> SEQUENCE: 34
gttttgggaa attccctatt aatgttagta ttccttggac tc   42

<210> SEQ ID NO 35
<211> LENGTH: 41

```
<212> TYPE: DNA
<213> ORGANISM: artificial sequence
<220> FEATURE:
<223> OTHER INFORMATION: primer

<400> SEQUENCE: 35
ctgcactcag taatacatac ggtggtctcc atgcgacgtg c                 41

<210> SEQ ID NO 36
<211> LENGTH: 552
<212> TYPE: DNA
<213> ORGANISM: artificial sequence
<220> FEATURE:
<223> OTHER INFORMATION: Core-encoding nucleotide sequence present in
      pGA4-core plasmide

<400> SEQUENCE: 36
atggacattg atccttataa agaatttgga gctactgtgg agttactctc ttttttgcct    60
tctgacttct ttccttcagt acgtgatctt ctagataccg cctcagctct gtatcgggaa   120
gccttagagt ctcctgagca ttgttcacct caccatactg ctctcaggca agcaattctg   180
tgctgggggg aactaatgac tctagctacc tgggtgggtg gtaatttgga agatccaata   240
tccagggacc tagtagtcag ttatgtcaac actaatatgg gctaaagtt ccggcaacta    300 ttgtggtttc acattcttg tctcactttt ggaagagaaa cagttataga atatttggtg    360
tctttcggag tgtggattcg cactcctcca gcttatagac caccaaatgc ccctatctta   420
tcaacacttc cggagactac tgttgttaga cgacgaggca ggtcccctag aagaagaact   480
ccctcgcctc gcagacgaag gtctcaatcg ccgcgtcgca aagatctca atctcgggaa    540 tctcagtgct aa                                                       552

<210> SEQ ID NO 37
<211> LENGTH: 42
<212> TYPE: DNA
<213> ORGANISM: artificial sequence
<220> FEATURE:
<223> OTHER INFORMATION: primer

<400> SEQUENCE: 37
gactgttaac caccatggac attgatcctt ataaagaatt tg                42

<210> SEQ ID NO 38
<211> LENGTH: 41
<212> TYPE: DNA
<213> ORGANISM: artificial sequence
<220> FEATURE:
<223> OTHER INFORMATION: primer

<400> SEQUENCE: 38
gttgacataa ctgactacca aattaccacc cacccaggta g                 41

<210> SEQ ID NO 39
<211> LENGTH: 42
<212> TYPE: DNA
<213> ORGANISM: artificial sequence
<220> FEATURE:
<223> OTHER INFORMATION: primer

<400> SEQUENCE: 39
gtgggtggta atttggtagt cagttatgtc aacactaata tg                42

<210> SEQ ID NO 40
<211> LENGTH: 33
```

```
<212> TYPE: DNA
<213> ORGANISM: artificial sequence
<220> FEATURE:
<223> OTHER INFORMATION: primer

<400> SEQUENCE: 40
gactctcgag ttaaacagta gtctccggaa gtg                                    33

<210> SEQ ID NO 41
<211> LENGTH: 42
<212> TYPE: DNA
<213> ORGANISM: artificial sequence
<220> FEATURE:
<223> OTHER INFORMATION: primer

<400> SEQUENCE: 41
gacgggatcc accatggaca ttgatcctta taaagaattt gg                          42

<210> SEQ ID NO 42
<211> LENGTH: 38
<212> TYPE: DNA
<213> ORGANISM: artificial sequence
<220> FEATURE:
<223> OTHER INFORMATION: primer

<400> SEQUENCE: 42
gcctgcttgc aggacaacag tagtctccgg aagtgttg                               38

<210> SEQ ID NO 43
<211> LENGTH: 702
<212> TYPE: DNA
<213> ORGANISM: artificial sequence
<220> FEATURE:
<223> OTHER INFORMATION: core and env-encoding nucleotide sequence
      present in pMK-C/E plasmid

<400> SEQUENCE: 43
atggacattg atccttataa agaatttgga gctactgtgg agttactctc tttcttgcct       60
tctgacttct ttccttcagt acgtgatctt ctagatacag cctcagctct gtatcgggaa      120
gccttagtcc tgcaagcagg cttcttcctg ctgacccgta ttctgaccat tccacaaagc      180
ctggatagct ggtggaccag cctgaacttc ctgggtggca ccacggtttg cctgggtcag      240
gagtctcctg agcattgttc acctcaccat actgctctca ggcaagcaat tctgtgctgg      300
ggagaactaa tgactctagc tacctgggtg gtggttggg caagcgcacg ctttagctgg      360
ctgagcctgc tggttccgtt cgtgcaatgg tttgtgggtc tgagcccaac cgtgtggctg      420
agcgtgaatt tggtagtcag ttatgtcaac actaatatgg gactaaagtt ccgacaacta      480
ttgtggtttc acatttcttg tctcactttt ggaagagaaa cagttataga atatttggtg      540
tctttcggag tgtggattcg cactcctcca gcttatagac accaaacgc accgatactg       600 agcaccctgc cagaaaccac cgtgggtccg agcttatatt ctatactgag cccattcctg      660
ccattactgc cgatcttctt ctgcctgtgg gtgtatatct ga                         702

<210> SEQ ID NO 44
<211> LENGTH: 36
<212> TYPE: DNA
<213> ORGANISM: artificial sequence
<220> FEATURE:
<223> OTHER INFORMATION: primer

<400> SEQUENCE: 44
ccggagacta ctgttgtcct gcaagcaggc ttcttc                                 36
```

<210> SEQ ID NO 45
<211> LENGTH: 47
<212> TYPE: DNA
<213> ORGANISM: artificial sequence
<220> FEATURE:
<223> OTHER INFORMATION: primer

<400> SEQUENCE: 45
gagtcattct cgacttgcgg ccgcttactg acccaggcaa accgtgg                    47

<210> SEQ ID NO 46
<211> LENGTH: 35
<212> TYPE: DNA
<213> ORGANISM: artificial sequence
<220> FEATURE:
<223> OTHER INFORMATION: primer

<400> SEQUENCE: 46
gcgtgcgctt gcccactgac ccaggcaaac cgtgg                                 35

<210> SEQ ID NO 47
<211> LENGTH: 38
<212> TYPE: DNA
<213> ORGANISM: artificial sequence
<220> FEATURE:
<223> OTHER INFORMATION: primer

<400> SEQUENCE: 47
cggtttgcct gggtcagtgg gcaagcgcac gctttagc                              38

<210> SEQ ID NO 48
<211> LENGTH: 48
<212> TYPE: DNA
<213> ORGANISM: artificial sequence
<220> FEATURE:
<223> OTHER INFORMATION: primer

<400> SEQUENCE: 48
gagtcattct cgacttgcgg ccgcttacac gctcagccac acggttgg                   48

<210> SEQ ID NO 49
<211> LENGTH: 50
<212> TYPE: DNA
<213> ORGANISM: artificial sequence
<220> FEATURE:
<223> OTHER INFORMATION: primer

<400> SEQUENCE: 49 gggggggctag caagcttcca ccatggacat tgatccttat aaagaatttg                50

<210> SEQ ID NO 50
<211> LENGTH: 45
<212> TYPE: DNA
<213> ORGANISM: artificial sequence
<220> FEATURE:
<223> OTHER INFORMATION: primer

<400> SEQUENCE: 50
gaaagaatcc agcttgcagg acgcactgag attcccgaga ttgag                      45

<210> SEQ ID NO 51
<211> LENGTH: 45
<212> TYPE: DNA
<213> ORGANISM: artificial sequence
<220> FEATURE:

<223> OTHER INFORMATION: primer

<400> SEQUENCE: 51
ctcaatctcg ggaatctcag tgcgtcctgc aagctggatt ctttc          45

<210> SEQ ID NO 52
<211> LENGTH: 44
<212> TYPE: DNA
<213> ORGANISM: artificial sequence
<220> FEATURE:
<223> OTHER INFORMATION: primer

<400> SEQUENCE: 52
gagtcattct cgacttgcgg ccgcttagat ataaacccac aagc          44

<210> SEQ ID NO 53
<211> LENGTH: 52
<212> TYPE: DNA
<213> ORGANISM: artificial sequence
<220> FEATURE:
<223> OTHER INFORMATION: primer

<400> SEQUENCE: 53 gggggggctag caagcttcca ccatgaatgt tagtattcct tggactcata ag          52

<210> SEQ ID NO 54
<211> LENGTH: 49
<212> TYPE: DNA
<213> ORGANISM: artificial sequence
<220> FEATURE:
<223> OTHER INFORMATION: primer

<400> SEQUENCE: 54
gagtcattct cgacttgcgg ccgctcacgg tggtctccat gcgacgtgc          49

<210> SEQ ID NO 55
<211> LENGTH: 9
<212> TYPE: PRT
<213> ORGANISM: artificial sequence
<220> FEATURE:
<223> OTHER INFORMATION: peptide

<400> SEQUENCE: 55

Ser Leu Tyr Ala Asp Ser Pro Ser Val
1               5

<210> SEQ ID NO 56
<211> LENGTH: 10
<212> TYPE: PRT
<213> ORGANISM: artificial sequence
<220> FEATURE:
<223> OTHER INFORMATION: peptide

<400> SEQUENCE: 56

Phe Leu Pro Ser Asp Phe Phe Pro Ser Val
1               5                   10

<210> SEQ ID NO 57
<211> LENGTH: 10
<212> TYPE: PRT
<213> ORGANISM: artificial sequence
<220> FEATURE:
<223> OTHER INFORMATION: peptide

<400> SEQUENCE: 57

Ile Leu Cys Trp Gly Glu Leu Met Thr Leu

<210> SEQ ID NO 58
<211> LENGTH: 9
<212> TYPE: PRT
<213> ORGANISM: artificial sequence
<220> FEATURE:
<223> OTHER INFORMATION: peptide

<400> SEQUENCE: 58

Val Leu Gln Ala Gly Phe Phe Leu Leu
1               5

<210> SEQ ID NO 59
<211> LENGTH: 9
<212> TYPE: PRT
<213> ORGANISM: artificial sequence
<220> FEATURE:
<223> OTHER INFORMATION: peptide

<400> SEQUENCE: 59

Phe Leu Gly Gly Thr Thr Val Cys Leu
1               5

<210> SEQ ID NO 60
<211> LENGTH: 10
<212> TYPE: PRT
<213> ORGANISM: artificial sequence
<220> FEATURE:
<223> OTHER INFORMATION: peptide

<400> SEQUENCE: 60

Gly Leu Ser Pro Thr Val Trp Leu Ser Val
1               5                   10

<210> SEQ ID NO 61
<211> LENGTH: 34
<212> TYPE: DNA
<213> ORGANISM: artificial sequence
<220> FEATURE:
<223> OTHER INFORMATION: PCR primer

<400> SEQUENCE: 61
gactctcgag ttagcactga gattcccgag attg                            34

<210> SEQ ID NO 62
<211> LENGTH: 10
<212> TYPE: PRT
<213> ORGANISM: artificial sequence
<220> FEATURE:
<223> OTHER INFORMATION: FLP variant core epitope (FLP4)

<400> SEQUENCE: 62

Phe Leu Pro Ser Asp Phe Phe Pro Ser Ile
1               5                   10

<210> SEQ ID NO 63
<211> LENGTH: 10
<212> TYPE: PRT
<213> ORGANISM: artificial sequence
<220> FEATURE:
<223> OTHER INFORMATION: ILC variant core epitope (ILC2)

<400> SEQUENCE: 63

Ile Leu Cys Trp Gly Glu Leu Met Asn Leu
1               5                   10

<210> SEQ ID NO 64
<211> LENGTH: 10
<212> TYPE: PRT
<213> ORGANISM: artificial sequence
<220> FEATURE:
<223> OTHER INFORMATION: ILC variant core epitope (ILC3)

<400> SEQUENCE: 64

Ile Val Cys Trp Gly Glu Leu Met Asn Leu
1               5                   10

<210> SEQ ID NO 65
<211> LENGTH: 10
<212> TYPE: PRT
<213> ORGANISM: artificial sequence
<220> FEATURE:
<223> OTHER INFORMATION: ILC variant core epitope (ILC4)

<400> SEQUENCE: 65

Ile Leu Cys Trp Gly Asp Leu Met Thr Leu
1               5                   10

<210> SEQ ID NO 66
<211> LENGTH: 10
<212> TYPE: PRT
<213> ORGANISM: artificial sequence
<220> FEATURE:
<223> OTHER INFORMATION: ILC variant core epitope (ILC5)

<400> SEQUENCE: 66

Ile Val Cys Trp Gly Glu Leu Met Thr Leu
1               5                   10

<210> SEQ ID NO 67
<211> LENGTH: 10
<212> TYPE: PRT
<213> ORGANISM: artificial sequence
<220> FEATURE:
<223> OTHER INFORMATION: ILC variant core epitope (ILC6)

<400> SEQUENCE: 67

Ile Leu Cys Trp Val Glu Leu Met Asn Leu
1               5                   10

<210> SEQ ID NO 68
<211> LENGTH: 10
<212> TYPE: PRT
<213> ORGANISM: artificial sequence
<220> FEATURE:
<223> OTHER INFORMATION: ILC variant core epitope (ILC7)

<400> SEQUENCE: 68

Val Leu Cys Trp Gly Glu Leu Met Thr Leu
1               5                   10

<210> SEQ ID NO 69
<211> LENGTH: 9
<212> TYPE: PRT
<213> ORGANISM: artificial sequence
<220> FEATURE:
<223> OTHER INFORMATION: VLQ variant env epitope (VLQ2)

<400> SEQUENCE: 69

Val Leu Gln Ala Gly Phe Phe Ser Leu
1               5

```
<210> SEQ ID NO 70
<211> LENGTH: 9
<212> TYPE: PRT
<213> ORGANISM: artificial sequence
<220> FEATURE:
<223> OTHER INFORMATION: FLG variant Env epitope (FLG2)

<400> SEQUENCE: 70

Phe Leu Gly Gly Thr Pro Val Cys Leu
1               5

<210> SEQ ID NO 71
<211> LENGTH: 9
<212> TYPE: PRT
<213> ORGANISM: artificial sequence
<220> FEATURE:
<223> OTHER INFORMATION: FLG variant Env epitope (FLG3)

<400> SEQUENCE: 71

Phe Leu Gly Gly Ala Pro Thr Cys Pro
1               5

<210> SEQ ID NO 72
<211> LENGTH: 9
<212> TYPE: PRT
<213> ORGANISM: artificial sequence
<220> FEATURE:
<223> OTHER INFORMATION: FLG variant Env epitope (FLG4)

<400> SEQUENCE: 72

Phe Leu Gly Glu Thr Pro Val Cys Leu
1               5

<210> SEQ ID NO 73
<211> LENGTH: 10
<212> TYPE: PRT
<213> ORGANISM: artificial sequence
<220> FEATURE:
<223> OTHER INFORMATION: GLSP variant Env epitope (GLSP2)

<400> SEQUENCE: 73

Gly Leu Ser Pro Thr Val Trp Leu Leu Val
1               5                   10

<210> SEQ ID NO 74
<211> LENGTH: 10
<212> TYPE: PRT
<213> ORGANISM: artificial sequence
<220> FEATURE:
<223> OTHER INFORMATION: GLSP variant Env epitope (GLSP3)

<400> SEQUENCE: 74

Gly Leu Ser Pro Ile Val Trp Leu Ser Val
1               5                   10

<210> SEQ ID NO 75
<211> LENGTH: 9
<212> TYPE: PRT
<213> ORGANISM: artificial sequence
<220> FEATURE:
<223> OTHER INFORMATION: SLY variant pol epitope (SLY2)

<400> SEQUENCE: 75

Ser Leu Tyr Ala Val Ser Pro Ser Val
1               5
```

COMPOSITION FOR TREATING HBV INFECTION

CROSS REFERENCE TO RELATED APPLICATIONS

This application is a continuation of U.S. patent application Ser. No. 13/423,193, filed on Mar. 17, 2012, now U.S. Pat. No. 10,076,570, issued on Sep. 18, 2018, which is a Continuation-In-Part of U.S. patent application Ser. No. 13/388,826, filed on Feb. 3, 2012, now U.S. Pat. No. 9,393,299, issued on Jul. 19, 2016, which is a U.S. National Phase pursuant to 35 U.S.C. § 371 of International Application PCT/EP2010/061492, filed on Aug. 6, 2010, and published as WO 2011/015656 on Feb. 10, 2011, which claims priority to European Patent Application 09305742.0, filed on Aug. 7, 2009, all of which are incorporated herein by reference in their entireties for all purposes.

The present invention relates to immunogenic compositions with hepatitis B virus (HBV) component(s), and which may be either nucleic acid- or polypeptide-based. Said immunogenic compositions can be used for stimulating or enhancing an immune response to HBV with the goal of providing a protective or therapeutic effect against HBV infection and any condition or disease caused by or associated with an HBV infection. The present invention also relates to expression vectors for expressing such HBV component(s) and their therapeutic or prophylactic use. The invention is of very special interest in the field of immunotherapy, and more particular for treating patients infected with HBV, especially those chronically infected.

BACKGROUND

Hepatitis B is a major public health problem with more than 350 million persons chronically infected worldwide, 20 to 40% of them being at risk of developing chronic liver disease, cirrhosis and hepatocellular carcinoma. Despite the existence of effective preventive vaccines, the hepatitis B virus (HBV) infection is still rampant in many countries, even developed ones, with an estimation of 4.5 millions of new cases of infection per year worldwide. Unlike the WHO recommendation which is to implement universal vaccination, the coverage of full course preventive vaccination varies from 25% in Asia to $^{75}$-90% in Europe. Currently hepatitis B is the $10^{th}$ cause of mortality (around 1 million of deaths/year) and HBV related liver carcinoma, the $5^{th}$ most frequent cancer. Geographic repartition of HBV infection is uneven with prevalence lower than 1% in Western countries to more than 10% in South Eastern countries, most part of Africa and Equatorial South America. In high HBV chronic carrier prevalence area, vertical transmission from infected mother to neonate is the most frequent mode of contamination and almost always results in chronic hepatitis (90% of cases). This rate can be lowered to 15% by preventive vaccination of infected babies immediately after birth. In Western countries, infection occurs most likely during adulthood through horizontal transmission, via body fluids such as blood, semen, saliva, resulting in acute and self recovering infection in 85% of patients but nevertheless to chronic infection in 15% of cases.

Hepatitis B virus (HBV) is a member of the hepadnaviridae and primarily infects the liver, replicating in hepatocytes. The infectious particles are the so called 42-45 nm "Dane particles" which consist of an outer lipoprotein envelope which contains three different surface proteins (HBs) and an inner nucleocapsid, the major structural protein of which is the core protein (HBcAg). Within the nucleocapsid is a single copy of the HBV genome linked to the viral polymerase protein (P). In addition to 42-45-nm virions, the blood of HBV-infected patients contains 20-nm spheres made of HBsAg and host-derived lipids which are released from infected cells. These spheres outnumber the virions by a factor of $10^4$-$10^6$.

The HBV genome is a relaxed circular partially double-stranded DNA of approximately 3,200 nucleotides consisting of a full-length negative strand and a shorter positive strand. It contains 4 overlapping open reading frames (ORFs), C, S, P and X. The C ORF encodes the core protein (or HBcAg), a 183 amino acid-long protein which constitutes the HBV nucleocapsid and a second protein found in the serum of patients during virus replication known as HBeAg which contains a precore N-terminal extension and a part of HBcAg. The C-terminus of the core protein is very basic and contains 4 Arg-rich domains which are predicted to bind nucleic acids as well as numerous phosphorylation sites (the phosphorylation state of core is associated with conformational changes in the capsid particle as described in Yu and Sommers, 1994, J. Virol. 68:2965). The S ORF encodes three surface proteins all of which have the same C terminus but differ at their N-termini due to the presence of three in-frame ATG start codons that divide the S ORF into three regions, S (226 amino acids), pre-S2 (55 amino acids) and pre-S1 (108 amino acids), respectively. The large-surface antigen protein (L) is produced following translation initiation at the first ATG start codon and comprises 389 amino acid residues (preS1-preS2-S). The middle surface antigen protein (M) results from translation of the S region and the pre-S2 region starting at the second start ATG whereas the small surface antigen protein of 226 amino acids (S, also designated HBsAg) results from translation of the S region initiated at the third start ATG codon. The HBV surface proteins are glycoproteins with carbohydrate side chains (glycans) attached by N-glycosidic linkages. The P ORF encodes the viral polymerase and the X ORF contains a protein known as the X protein, which is thought to be a transcriptional activator.

After virions enter hepatocytes, by an as-yet-unknown receptor, nucleocapsids transport the genomic HBV DNA to the nucleus, where the relaxed circular DNA is converted to covalently closed circular DNA (cccDNA). The cccDNA functions as the template for the transcription of four viral RNAs, which are exported to the cytoplasm and used as mRNAs for translation of the HBV proteins. The longest (pre-genomic) RNA also functions as the template for HBV replication, which occurs in nucleocapsids in the cytoplasm. Some of the HBV DNA and polymerase-containing capsids are then transported back to the nucleus, where they release the newly generated relaxed circular DNA to form additional cccDNA. With a half-life longer than the one of hepatocytes, the cccDNA is responsible for the persistence of HBV. Other capsids are enveloped by budding into the endoplasmic reticulum and secreted after passing through the Golgi complex.

A number of preclinical and clinical studies have emphasized the importance of CD4+ and CD8+ T cell immune responses for effective anti-viral response (Ferrari et al, 1990, J Immul, 145:3442; Penna et al, 1996, J Clin Invest, 98:1185; Penna et al, 1997, Hepatology, 25:1022). That is to say, patients naturally having recovered from hepatitis B mounted multi-specific and sustained responses mediated by T helper ($T_H$) and cytotoxic T (CTL) lymphocytes which are readily detectable in peripheral blood. Upon recognition of viral peptides, CTL acquire the capacity to either cure HBV-infected cells via a non-cytopathic, cytokine mediated inhibition of HBV replication and/or to kill them via perforin-Fas ligand and TNFα-mediated death pathways. Both effector functions have been observed during resolution of acute hepatitis B and this type 1 T-cell (Th1) response persists after clinical recovery. It often coincides with an elevation of serum alanine-aminotransferase (ALT) levels and with appearance of HBcAg specific IgM and IgG. Anti-HBe and anti-HBs antibodies appear later and indicate a favorable outcome of infection. HBsAg-specific antibodies are neutralizing, mediate protective immunity and persist for life after clinical recovery. Chronic HBV infection is, however, only rarely resolved by the immune system. When this occurs, viral clearance is associated with increased CTL activity and increased ALT levels caused by a destruction of infected hepatocytes by the immune system. However, the vast majority of chronically infected patients show weak and temporary CD4 and CD8 T cell immune responses that are antigenically restricted and ineffective to clear viral infection, although individual HBV-specific T-cell clones have been isolated and expanded from liver biopsies. The reason for this alteration of the effector functions of the cellular immune response in chronic hepatitis B is currently not known. However it was shown that functional T cell responses can be partially restored in some patients when the viral load is below a threshold of $10^6$ IU/mL (Webster et al 2004, J. Virol. 78:5707). These data are clearly encouraging and emphasize the need for immunomodulatory strategies capable of inducing an effective T-cell response.

Ideally, treatment of chronic viral hepatitis B should first permit to suppress HBV replication before irreversible liver damage, so as to eliminate the virus, prevent disease progression to cirrhosis or liver cancer and improve patient survival. Conventional treatment of chronic hepatitis B includes pegylated interferon-alpha (IFNa) and nucleoside/nucleotide analogues (NUCs) such as lamivudine, and more recently entecavir, telbivudine, adefovir and tenofovir (EASL Clinical Practice Guidelines: management of chronic hepatitis B, 2009). IFNa is a potent antiviral molecule, whereby inhibiting viral replication, which however, causes serious side effects in merely 25-30% of patients. NUCs act as competitive inhibitors of HBV polymerase aimed to inhibit the reverse transcription of the pre-genomic RNA into the negative DNA strand and then the double stranded viral DNA. They limit the formation of new virions, but are ineffective to eliminate the supercoiled cccDNA hidden in the nucleus of infected hepatocytes which constitutes a source of new progeny viruses. This can explain why NUC efficacy is temporary and viral rebound occurs immediately after cessation of treatment, requiring patients to stay life long under treatment. In addition, long-term efficacy is also limited due to emergence of resistant HBV mutants (more than 24% after one year and approximately 66% after four years of lamivudine treatment as discussed in Leung et al., 2001, Hepatology 33:1527) although newer NUCs (entecavir, telbivudine and tenofovir) showed much fewer occurrences of drug-resistant HBV mutants, while increasing suppression of HBV DNA. Long-term treatment data with these new drugs are, however, limited and this higher efficacy has not been correlated with a significantly higher rate of HBs-seroconversion.

Besides antiviral therapies, efforts are currently made to develop supplemental therapies aiming at improved host's immune responses, specifically those mediated by cytotoxic T and helper T lymphocytes. A large majority of existing immunotherapy approaches have focused on the use of HBV surface protein(s), S preS1 and/or preS2 (Smith et al., 1983, Nature 302:490; Lubeck et al., 1989, Proc. Natl Acad. Sci. USA 86:6763; Adkins et al., 1998, BioDrugs 10:137; Loirat et al., 2000, J. Immunol. 165:4748; Funuy-Ren et al. 2003, J. Med. Virol. 71:376; Kasaks et al., 2004, J. Gen. Virol. 85:2665; Xiangming Li et al., 2005, Intern. Immunol. 17:1293; Mancini-Bourguine et al., 2006, Vaccine 24:4482; Vandepapeliere et al., 2007, Vaccine 25:8585). Encouraging results were obtained at least with respect to the stimulation of immune responses. For example, Mancini-Bourguine et al. (2006, Vaccine 24:4482) reported induction and/or recall T cell responses in HBV chronically infected patients injected with a preS2-S-encoding DNA vaccine, which is a good indication that the immune system is still operational in these patients.

HBcAg was also used as an immunogen (Yi-Ping Xing et al., 2005, World J. Gastro. 11:4583) as well as chimeric HBcAg capsids bearing foreign epitopes on their surface (WO92/11368; WO00/32625; Koletzki et al., 1997, J. Gen. Virol. 78:2049). The most promising location for inserting epitopes from the point of view of immunogenicity seems to be the site of an outer loop predicted to be on the surface of HBcAg in the vinicity of position 80 (Argos et al. 1988, EMBO J. 7:819). Schodel et al. (1992, J. Virol. 66:106) and Borisova et al. (1993, J. Virol. 67:3696) were able to insert preS1 and HBsAg epitopes in this region and reported successful immunization with the chimeric particles.

Multivalent vaccine candidates aimed to simultaneously target multiple HBV antigens have also been investigated. Notably, a polyepitope DNA vaccine encoding a fusion polypeptide of multiple cytotoxic T-lymphocytes (CTL) and helper T-lymphocyte (HTL) epitopes present in envelope, core and polymerase proteins was shown to elicit multiple CTL and HTL responses in preclinical mouse models (Depla et al., 2008, J. Virol. 82:435). Several vaccine formulations based on a mixture of DNA plasmids encoding HBsAg, HBcAg and HBV polymerase were developed (WO2005/056051; WO2008/020656) and demonstrated specific anti-HBV cellular and humoral responses in transgenic mouse model of chronic hepatitis B (Chae Young Kim et al., 2008, Exp. Mol. Medicine 40:669). Phase I clinical trials were initiated in South Korea in HBV carriers in combination with lamivudine treatment (Yang et al., 2006, Gene Ther. 13:1110).

Accordingly, there still exists a need for alternative immunotherapeutic approaches for inducing immune responses in a more potent and effective manner, especially cell-mediated immune responses, in an individual in need thereof such as an HBV chronically infected patient. Moreover, there is a need to provide vector-based composition capable of expressing the HBV antigen in a stable and sustained manner.

This technical problem is solved by the provision of the embodiments as defined in the claims.

Other and further aspects, features and advantages of the present invention will be apparent from the following description of the presently preferred embodiments of the invention. These embodiments are given for the purpose of disclosure.

SUMMARY OF THE INVENTION

Accordingly, in a first aspect, the present invention provides an immunogenic composition comprising at least one polypeptide or a nucleic acid molecule encoding said at least one polypeptide, wherein said at least one polypeptide is selected from the group consisting of:

(i) A polymerase moiety comprising at least 450 amino acid residues of a polymerase protein originating from a first HBV virus;

(ii) A core moiety comprising at least 100 amino acid residues of a core protein originating from a second HBV virus; and (iii) An env moiety comprising one or more immunogenic domain(s) of 15 to 100 consecutive amino acid residues of a HBsAg protein originating from a third HBV virus; or Any combination of said polymerase moiety, core moiety, env moiety, said nucleic acid molecule encoding said polymerase moiety, said nucleic acid molecule encoding said core moiety and/or said nucleic acid molecule encoding said env moiety.

Definitions

As used herein throughout the entire application, the terms "a" and "an" are used in the sense that they mean "at least one", "at least a first", "one or more" or "a plurality" of the referenced compounds or steps, unless the context dictates otherwise. For example, the term "a cell" includes a plurality of cells including a mixture thereof.

The term "and/or" wherever used herein includes the meaning of "and", "or" and "all or any other combination of the elements connected by said term".

The term "about" or "approximately" as used herein means within 10%, preferably within 8%, and more preferably within 5% of a given value or range.

As used herein, when used to define products, compositions and methods, the term "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are open-ended and do not exclude additional, unrecited elements or method steps. "Consisting essentially of" means excluding other components or steps of any essential significance. Thus, a composition consisting essentially of the recited components would not exclude trace contaminants and pharmaceutically acceptable vehicles. "Consisting of" means excluding more than trace elements of other components or steps. For example, a polypeptide "consists of" an amino acid sequence when the polypeptide does not contain any amino acids but the recited amino acid sequence. A polypeptide "consists essentially of" an amino acid sequence when such an amino acid sequence is present with eventually only a few additional amino acid residues. A polypeptide "comprises" an amino acid sequence when the amino acid sequence is at least part of the final amino acid sequence of the polypeptide. Such a polypeptide can have a few up to several hundred additional amino acids residues.

The terms "amino acids", "residues" and "amino acid residues" are synonyms and encompass natural amino acids as well as amino acid analogs (e.g. non-natural, synthetic and modified amino acids, including D or L optical isomers).

The terms "polypeptide", "peptide" and "protein" are used herein interchangeably to refer to polymers of amino acid residues which comprise nine or more amino acids bonded via peptide bonds. The polymer can be linear, branched or cyclic and may comprise naturally occurring and/or amino acid analogs and it may be interrupted by non-amino acids. As a general indication, if the amino acid polymer is long (e.g. more than 50 amino acid residues), it is preferably referred to as a polypeptide or a protein whereas if it is 50 amino acids long or less, it is referred to as a "peptide".

Within the context of the present invention, the terms "nucleic acid", "nucleic acid molecule", "polynucleotide" and "nucleotide sequence" are used interchangeably and define a polymer of any length of either polydeoxyribonucleotides (DNA) (e.g., cDNA, genomic DNA, plasmids, vectors, viral genomes, isolated DNA, probes, primers and any mixture thereof) or polyribonucleotides (RNA) molecules (e.g., mRNA, antisense RNA) or mixed polyribo-polydeoxyribonucleotides. They encompass single or double-stranded, linear or circular, natural or synthetic polynucleotides. Moreover, a polynucleotide may comprise non-naturally occurring nucleotides, such as methylated nucleotides and nucleotide analogs (see U.S. Pat. Nos. 5,525,711, 4,711,955 or EPA 302 175 as examples of modifications) and may be interrupted by non-nucleotide components. If present, modifications to the nucleotide may be imparted before or after polymerization.

As used herein, the term "immunogenic composition" refers to a formulation which comprises 1, 2, 3, 4 or more component(s) described hereinafter (e.g. the polymerase moiety, the core moiety, the env moiety, the nucleic acid molecule encoding the polymerase moiety, the nucleic acid molecule encoding the core moiety and/or the nucleic acid molecule encoding the env moiety) and optionally other components (e.g. adjuvant, carrier, diluent, etc). The immunogenic composition of the present invention will typically be in a form that is capable of being administered to a host organism and induces a protective or therapeutic immune response sufficient to induce or stimulate anti-HBV immunity, resulting in a therapeutic benefit such as prevent an HBV infection, reduce and/or ameliorate at least one condition caused by or associated with an HBV infection (e.g. reduce the viral load, reduce or delay the risk of hepatic lesions such as cirrhosis or liver cancer, improve liver history, etc), and/or reduce serum HBeAg or HBsAg level or both, and/or induce HBe seroconversion, HBs seroconversion or both and/or enhance the efficacy of another anti-HBV therapy or prophylaxis. Upon introduction in a host organism, the immunogenic composition of the present invention is able to provoke an immune response including, but not limited to, the production of antibodies and/or cytokines and/or the activation of cytotoxic T cells, B, T-lymphocytes, antigen presenting cells, helper T cells, dendritic cells, NK cells, leading to the production of innate immune response and/or specific humoral and/or cellular immune responses against at least one HBV antigen/epitope.

An "immunogenic domain" refers to a structural portion of an HBV protein capable of being bound by an antibody or T cell receptor. Typically, such an immunogenic domain contains one or more B and/or T epitope(s), in particular. CTL or $T_H$ epitopes or both, and are involved in recognition by a particular antibody, or in the context of an MHC (Major Histocompatibility Complex), by T-cell receptors. An "epitope" corresponds to a minimal peptide motif (usually a set of 9-11 amino acid residues) that together form a site recognized by an antibody, T-cell receptor or HLA molecule. Those residues can be consecutive (linear epitope) or not (conformational epitope that includes residues that are not immediately adjacent to one another). Recognition of a T-cell epitope by a T-cell is generally believed to be via a mechanism wherein T-cells recognize peptide fragments of antigens which are bound to class I or class II MHC molecules expressed on antigen-presenting cells.

As used herein, "HBV" and "hepatitis B virus" are used interchangeably and refer to any member of the hepadnaviridae (see e.g. Ganem and Schneider in Hepadnaviridae (2001) "The viruses and their replication" (pp 2923-2969), Knipe D M et al., eds. Fields Virology, 4th ed. Philadelphia, Lippincott Williams & Wilkins or subsequent edition). Extensive phylogenetic analyses have led to the classification of hepatitis B viruses into 8 major genotypes (A to H), which show sequence divergence by at least 8%. The various HBV genotypes show distinct geographic distribution and can display heterogeneous disease symptoms and/or clinical outcome. The various HBV were classified in nine different subtypes (ayw1, ayw2, ayw3, ayw4, ayr, adw2, adw4, adrq+ and adqr−) in connection with HBsAg-associated serology (see review by Mamum-Al Mahtab et al., 2008, Hepatobiliary Pancrease Dis Int 5:457; Schaeffer, 2007, World Gastroenterol. 7:14; Norder et al., 1993, J. Gen Virol. 74:1341). Each genotype and serotype encompasses different HBV strains and isolates. An isolate corresponds to a specific virus isolated from a particular source of HBV (e.g. a patient sample or other biological HBV reservoir) whereas a strain encompasses various isolates which are very close each other in terms of genomic sequences A number of HBV suitable for use in the context of the present invention are described in the art, especially in Genbank. Exemplary HBV of genotype A include without limitation isolate HB-JI444AF and strain HB-JI444A (accession number AP007263). Exemplary HBV of genotype B include without limitation clone pJDW233 (accession number D00329), isolate HBV/14611 (accession number AF121243), HBV-B1 identified in 2001 by Hou, et al. (GenBank accession number AF282917.1), HBV strain Whutj-37 (GenBank accession number AY2933309.1) identified by Zhang et al. (2005, Arch. Virol. 150, 721-741), the Chinese HBV strain GDH1 identified by He et al. (GenBank accession number AY766463.1) and HBV isolate 57-1 subtype adw identified by Jiang et al. (GenBank accession number AY518556.1). Exemplary HBV of genotype C include without limitation isolate AH-1-ON980424 (accession number AB 113879), strain HCC-3-TT (accession number AB 113877), HBV isolate SWT3.3 identified by Fang et al. (GenBank accession number EU916241.1), HBV isolate H85 identified by Zhu et al. (GenBank accession number AY306136.1), HBV strain C1248 identified by Tu et al. (GenBank accession number DQ975272.1), HBV isolate CHN-H155 (GenBank accession number DQ478901.1) identified by Wang et al. (2007, J. Viral Hepat 14, 426-434) and HBV isolate GZ28-1 identified by Zhou et al. (GenBank accession number EF688062). Exemplary HBV of genotype D include without limitation isolates KAMCHATKA27 (accession number AB188243), ALTAY136 (accession number AB188245) and Y07587 described in Stoll-Becker et al. (1997, J. Virol. 71:5399) and available at Genbank under accession number Y07587 as well as the HBV isolate described under accession number AB267090. Exemplary HBV of genotype E include without limitation isolate HB-JI411F and strain HB-JI411 (accession number AP007262). Exemplary HBV of genotype F include without limitation isolates HBV-BL597 (accession number AB214516) and HBV-BL592 (accession number AB166850). Exemplary HBV of genotype G include without limitation isolate HB-JI444GF and strain HB-JI444G (accession number AP007264). Exemplary HBV of genotype H include without limitation isolate HBV ST0404 (accession number AB298362) and isolate HB-JI260F and strain HB-JI260 (accession number AP007261). However, the present invention is not limited to these exemplary HBV. Indeed the nucleotide and amino acid sequences can vary between different HBV isolates and genotypes and this natural genetic variation is included within the scope of the invention as well as non-natural modification(s) such as those described below.

As used herein, a "native HBV protein" refers to a protein, polypeptide or peptide (e.g. the polymerase protein, the core protein or the HBsAg, etc) that can be found, isolated, obtained from a source of HBV in nature as distinct from one being artificially modified or altered by man in the laboratory. Thus, this term would include naturally-occurring HBV proteins polypeptides or peptides unless otherwise specified. Such sources in nature include biological samples (e.g. blood, plasma, sera, semen, saliva, tissue sections, biopsy specimen etc.) collected from a subject infected or that has been exposed to HBV, cultured cells (such as HepG2.2.15, HuH6-C15 (Sureau et al., 1986, Cell 47:37; Sells et al., 1987, Proc. Natl. Acad. Sci. 84(4):1005); HuH7.TA61 or HuH7.TA62 (Sun et al., 2006, J Hepatol. 45(5):636), tissue cultures as well as recombinant materials. Recombinant materials include without limitation HBV isolate (e.g. available in depositary institutions), HBV genome, genomic RNA or cDNA libraries, plasmids containing HBV genome or fragment(s) thereof or any prior art vector known to include such elements.

Nucleotide sequences encoding the various HBV proteins can be found in specialized data banks (e.g. those mentioned above) and in the literature (see e.g. Valenzuela et al., 1980, The nucleotide sequence of the hepatitis B viral genome and the identification of the major viral genes (pp 57-70) in "Animal Virus Genetics"; eds B. Fields, et al.; Academic Press Inc., New York and Vaudin et al., 1988, J. Gen. Virol. 69:1383). Representative examples of native polymerase, core and HBsAg polypeptides are set forth in SEQ ID NO: 1-3, respectively (SEQ ID NO: 1 provides the amino acid sequence of the native polymerase protein of HBV isolate Y07587, SEQ ID NO: 2 provides the amino acid sequence of the native core protein of HBV isolate Y07587 and SEQ ID NO: 3 provides the amino acid sequence of the native env (HBsAg) of HBV isolate Y07587). Nucleotide sequences encoding the native polymerase, core and HBsAg of Y07587 HBV are shown for illustrative purposes in SEQ ID NO: 4, 5 and 6, respectively. However, as discussed above, the HBV proteins are not limited to these exemplary sequences and genetic variation is included in the scope of the invention.

As used herein, the term "moiety" (e.g. polymerase, core and/or env moieties) refers to a protein, polypeptide or peptide that originates from a native HBV protein, polypeptide or peptide after being artificially modified or altered by man in the laboratory as described herein. The term "modified" encompasses deletion, substitution or addition of one or more nucleotide/amino acid residue(s), any combination of these possibilities (e.g. degeneration of the native nucleotide sequence to reduce homology between the HBV sequences encoded by the composition of the invention, introduction of appropriate restriction sites) as well as non natural arrangements (e.g. fusion between two or more HBV proteins, polypeptides or peptides or moiety/ies). When several modifications are contemplated, they can concern consecutive residues and/or non consecutive residues. Modification(s) can be generated by a number of ways known to those skilled in the art, such as site-directed mutagenesis (e.g. using the Sculptor™ in vitro mutagenesis system of Amersham, Les Ullis, France), PCR mutagenesis, DNA shuffling and by chemical synthetic techniques (e.g. resulting in a synthetic nucleic acid molecule). The modification(s) contemplated by the present invention encompass silent modifications that do not change the amino acid sequence of the encoded HBV polypeptides, as well as modifications that are translated into the encoded polypeptide resulting in a modified amino acid sequence as compared to the corresponding native one.

The term "originate" (or originating) is used to identify the original source of a molecule but is not meant to limit the method by which the molecule is made which can be, for example, by chemical synthesis or recombinant means.

Preferably, each of the HBV moieties in use in the present invention retains a high degree of amino acid sequence identity with the corresponding native HBV protein, over either the full length protein or portion(s) thereof. The percent identity between two polypeptides is a function of the number of identical positions shared by the sequences, taking into account the number of gaps which need to be introduced for optimal alignment and the length of each gap. Various computer programs and mathematical algorithms are available in the art to determine the percentage of identity between amino acid sequences, such as for example the Blast program (e.g. Altschul et al., 1997, Nucleic Acid Res. 25:3389; Altschul et al., 2005, FEBS J. 272:5101) available at NCBI. The same can be applied for nucleotide sequences. Programs for determining nucleotide sequence homology are also available in specialized data base (Genbank or the Wisconsin Sequence Analysis Package), for example BESTFIT, FASTA and GAP programs.

For example, further to the modifications described hereinafter (e.g. reduced enzymatic activities, etc), any or all of the HBV moieties comprised or encoded by the composition of the invention can be modified so as to be representative of a specific genotype, and thus comprise an amino acid sequence corresponding to a consensus or near consensus sequence which is typically determined after sequence alignment of various HBV polypeptides of a particular genotype.

The term "combination" as used herein refers to any kind of combination between at least two of the components comprised or encoded by the immunogenic composition of the invention and any arrangement possible of the various components with a specific preference for 2 or 3 of the said components. This encompasses mixture of two or more polypeptides, mixture of two or more nucleic acid molecules/vectors, mixture of one or more polypeptide(s) and one or more nucleic acid molecules/vectors, as well as fusion of two or more nucleic acid molecules so as to provide a single polypeptide chain bearing two or more HBV moieties (e.g. non natural arrangement).

In a preferred embodiment, the immunogenic composition of the invention comprises a combination of at least two of said polymerase moiety, core moiety, env moiety or of at least two of said nucleic acid molecules encoding said polymerase moiety, said nucleic acid molecule encoding said core moiety and/or said nucleic acid molecule encoding said env moiety. A particularly preferred composition of the invention is selected from the group consisting of (i) a composition comprising a combination of a polymerase moiety and a core moiety as defined herein or a combination of nucleic acid molecules encoding said polymerase moiety and said core moiety; (ii) a composition comprising a combination of a core moiety and a env moiety as defined herein or a combination of nucleic acid molecules encoding said core moiety and said env moiety; and (iii) a composition comprising a combination of a polymerase moiety, a core moiety and a env moiety as defined herein or a combination of nucleic acid molecules encoding said polymerase moiety, said core moiety and said env moiety.

The term "fusion" or "fusion protein" as used herein refers to the combination with one another of at least two polypeptides (or fragment(s) thereof) in a single polypeptide chain. Preferably, the fusion between the various polypeptides is performed by genetic means, i.e. by fusing in frame the nucleotide sequences encoding each of said polypeptides. By "fused in frame", it is meant that the expression of the fused coding sequences results in a single protein without any translational terminator between each of the fused polypeptides. The fusion can be direct (i.e. without any additional amino acid residues in between) or through a linker. The presence of a linker may facilitate correct formation, folding and/or functioning of the fusion protein. The present invention is not limited by the form, size or number of linker sequences employed and multiple copies of a linker sequence may be inserted at the junction between the fused polypeptides. Suitable linkers in accordance with the invention are 3 to 30 amino acids long and composed of repeats of amino acid residues such as glycine, serine, threonine, asparagine, alanine and/or proline (see for example Wiederrecht et al., 1988, Cell 54, 841; Aumailly et al., 1990 FEBS Lett. 262, 82; and Dekker et al., 1993, Nature 362, 852), e.g. Ser-Gly-Ser or Gly-Ser-Gly-Ser-Gly linker.

As used herein, the term "heterologous hydrophobic sequence" refers to a peptide of hydrophobic nature (that contains a high number of hydrophobic amino acid residues such as Val, Leu, Ile, Met, Phe, Tyr and Trp residues). "Heterologous" refers to a sequence that is foreign to the native HBV protein, polypeptide or peptide from which originate the selected HBV moiety. It can be a peptide foreign to an HBV virus (e.g. a peptide from a measle or a rabies virus) or a peptide from an HBV virus but in a position in which it is not ordinarily found within the viral genome. The heterologous hydrophobic sequence can be fused in frame at the N-terminus, at the C-terminus or within an HBV moiety and may play a role in polypeptide trafficking, facilitate polypeptide production or purification, prolong half-life, among other things. Suitable heterologous hydrophobic sequences in accordance with the invention are 15 to 100 amino acids long and contain a highly hydrophobic domain.

The term "vector" as used herein refers to both expression and non-expression vectors and includes viral as well as non viral vectors, including extrachromosomal vectors (e.g. multicopy plasmids) and integrating vectors designed for being incorporated into the host chromosome(s). Particularly important in the context of the invention are vectors for transferring nucleic acid molecule(s) in a viral genome (so-called transfer vectors), vectors for use in immunotherapy (i.e. which are capable of delivering the nucleic acid molecules to a host organism) as well as expression vectors for use in various expression systems or in a host organism.

As used herein, the term "viral vector" encompasses vector DNA as well as viral particles generated thereof. Viral vectors can be replication-competent, or can be genetically disabled so as to be replication-defective or replication-impaired. The term "replication-competent" as used herein encompasses replication-selective and conditionally-replicative viral vectors which are engineered to replicate better or selectively in specific host cells (e.g. tumoral cells).

As used herein, the term "regulatory sequence" refers to any sequence that allows, contributes or modulates the expression of a nucleic acid molecule in a given host cell or organism, including replication, duplication, transcription, splicing, translation, stability and/or transport of the nucleic acid or one of its derivative (i.e. mRNA) into a host cell or organism.

As used herein, the term "host cell" should be understood broadly without any limitation concerning particular organization in tissue, organ, or isolated cells. Such cells may be of a unique type of cells or a group of different types of cells and encompass bacteria, lower and higher eukaryotic cells as well as cultured cell lines, primary cells and proliferative cells. This term includes cells which can be or has been the recipient of the composition(s), nucleic acid molecule(s), vector(s) or infectious viral particle(s) of the invention and progeny of such cells.

The term "host organism" refers to a vertebrate, particularly a member of the mammalian species and especially domestic animals, farm animals, sport animals, and primates including humans. Preferably, the host organism is a patient suffering from a chronic HBV infection. The infecting HBV can be from the same genotype or serotype as at least one of the first, second or third HBV in use in the present invention.

As used herein, the term "isolated" refers to a protein, polypeptide, peptide, nucleic acid molecule, host cell or virus that is removed from its natural environment (i.e. separated from at least one other component(s) with which it is naturally associated).

As used herein a "therapeutically effective amount" is a dose sufficient for the alleviation of one or more symptoms normally associated with an HBV infection or any disease or condition caused by or associated with an HBV infection. When prophylactic use is concerned, this term means a dose sufficient to prevent or to delay the establishment of an HBV infection. "Therapeutic" compositions are designed and administered to a host organism already infected by an HBV with the goal of reducing or ameliorate at least one disease or condition caused by or associated with said HBV infection, eventually in combination with one or more conventional therapeutic modalities as described herein (e.g. treatment with nucleoside or nucleotide analogs). For example, a therapeutically effective amount for inducing an immune response could be that amount necessary to cause activation of the immune system (e.g. resulting in the development of an anti-HBV response). The term "cancer" encompasses any cancerous conditions including diffuse or localized tumors, metastasis, cancerous polyps as well as preneoplastic lesions (e.g. cirrhosis).

As used herein, a "pharmaceutically acceptable vehicle" is intended to include any and all carriers, solvents, diluents, excipients, adjuvants, dispersion media, coatings, antibacterial and antifungal agents, and absorption delaying agents, and the like, compatible with pharmaceutical administration In accordance with the present invention, said polymerase, core and/or env moieties comprised or encoded by the composition of the invention may originate independently from any HBV genotype, strain or isolate identified at present time, such as those described above in connection with the term "HBV". Further, each of the polymerase, core and env moieties may originate from a native corresponding HBV protein or from a modified HBV polypeptide (e.g. modified so as to be representative of a specific genotype). Thus, the first, second and third HBV virus from which originate the polymerase, core and env moieties comprised or encoded by the composition of the present invention can be independently from the same or different genotypes, serotypes and/or isolates. For example, using HBV moieties originating from two or three different HBV genotypes permits to provide protection against a broader range of HBV genotypes.

In one embodiment, it could be interesting to adapt the immunogenic composition of the invention to a specific geographic region by using at least one HBV moiety from HBV genotype(s) that is/are endemic in this region. For illustrative purposes, genotypes A and C are the most prevalent in the United States whereas patients from Western European countries are infected mostly with genotypes A and D and those in the Mediterranean basin by genotype D. Limited data from India suggest that genotypes A and D are most common in India. On the other hand, genotypes B and C are the most prevalent in China. For example, a composition of the invention destined to European countries may comprise a polymerase moiety which originates from genotype A and core and env moieties which originate from genotype D or vice versa. Alternatively, the polymerase and core moieties can be from genotype A and env moiety from genotype D. As another example, a composition of the invention destined to European countries and the USA may comprise polymerase, core and env moieties which independently originate from genotype A, C and D. On the other hand, a composition of the invention destined to China may comprise or encode polymerase, core and env moieties which independently originate from genotype B and/or C.

One may also adapt the immunogenic composition of the invention to the population of patients to be treated. For example, genotype A is more common among American Whites and African Americans and those with sexually acquired HBV infections whereas genotypes B and C, on the other hand, are common among Asian Americans, patients born in Asia and those with maternal to infant transmission of HBV infection. HBV genotypes have also been associated with different clinical outcomes (Schaeffer et al., 2005, J. Viral. Hepatitis 12:111) with genotypes D and F being associated with more severe disease progression and a worse prognosis than genotype A (Sanchez-Tapias et al., 2002, Gastroenterology 123:1848). It is within the reach of the skilled person to adapt the composition of the invention according to the population and/or geographic region to be treated by choosing appropriate HBV genotypes, serotypes, strain and/or isolates.

According to an advantageous embodiment, at least two of the first, second and third HBV viruses, and preferably all, are from the same HBV genotype, and particularly from genotype D. Independently, they can originate from the same isolate, with a specific preference for the first, second and third HBV viruses being from HBV isolate Y07587. Preferably, the polymerase moiety in use in the present invention comprises an amino acid sequence which exhibits at least 80% of identity, advantageously at least 85% of identity, preferably at least 90% of identity, more preferably at least 95% of identity, and even more preferably 100% identity with the amino acid sequence shown in SEQ ID NO: 1 or part(s) thereof comprising at least 450 amino acid residues. Alternatively or in combination, the core moiety in use in the present invention comprises an amino acid sequence which exhibits at least 80% of identity, advantageously at least 85% of identity, preferably at least 90% of identity, more preferably at least 95% of identity, and even more preferably 100% identity with the amino acid sequence shown in SEQ ID NO: 2 or part(s) thereof comprising at least 100 amino acid residues. Alternatively or in combination, the one or more immunogenic domains of the env moiety in use in the present invention comprises an amino acid sequence which exhibits at least 80% of identity, advantageously at least 85% of identity, preferably at least 90% of identity, more preferably at least 95% of identity, and even more preferably 100% identity with part(s) of 15-100 amino acid residues within the amino acid sequence shown in SEQ ID NO: 3.

Polymerase Moiety

According to one embodiment, the polymerase moiety comprised or encoded by the composition of the invention is modified as compared to the corresponding native HBV polymerase.

An appropriate modification is the truncation of at least 20 amino acid residues and at most 335 amino acid residues normally present at the N-terminus of a native HBV polymerase. This modification is particularly relevant for compositions of the invention also comprising a second polypeptide so as to reduce or delete the overlapping portions between polymerase and core moieties. It is within the reach of the skilled person to adapt the truncation to the composition of the invention within the recited range at least 20 amino acid residues and at most 335 amino acid residues. With respect to a native HBV polymerase, the polymerase moiety used in the context of the present invention is advantageously truncated by at least 30 amino acid residues and at most 200 amino acid residues, desirably by at least 35 amino acid residues and at most 100 amino acid residues, preferably by at least 40 amino acid residues and at most 60 amino acid residues, and more preferably at least 45 and at most 50 amino acid residues, with a special preference for a truncation including the first 47 or the 46 amino acid residues following the initiator Met residue located at the N-terminus of a native HBV polymerase. Preferably, the truncation extends from position 1 (Met initiator) or 2 to position 47 of SEQ ID NO: 1.

A preferred embodiment is directed to a polymerase moiety comprising an amino acid sequence which exhibits at least 80% of identity, advantageously at least 85% of identity, preferably at least 90% of identity, more preferably at least 95% of identity, and even more preferably 100% identity with the portion of the amino acid sequence shown in SEQ ID NO: 1 extending from approximately position 48 to approximately position 832; and even more preferably to a polymerase moiety comprising an amino acid sequence which exhibits at least 80% of identity, advantageously at least 85% of identity, preferably at least 90% of identity, more preferably at least 95% of identity, and even more preferably 100% identity with the amino acid sequence shown in SEQ ID NO: 7.

Alternatively or in combination, the polymerase moiety in use in the invention is modified so as to exhibit a reduced reverse-transcriptase (RTase) enzymatic activity with respect to a native HBV polymerase. Advantageously, said reduction of RTase activity is provided by one or more mutation(s) in the domain responsible for RTase enzymatic activity.

Structural and functional organization of HBV polymerases was investigated almost 20 years ago (see for example Radziwill et al., 1990, J. Virol. 64:613). They are multifunctional proteins with three functional domains that catalyze the major steps in HBV replication (priming, DNA synthesis and removal of RNA templates) and a non essential spacer which are arranged in the following order:
- the first domain extending from position 1 to approximately position 177 is responsible for HBV terminal protein activity,
- the spacer is located from approximately position 178 to approximately position 335,
- the DNA polymerase domain extending from approximately position 336 to approximately position 679 is responsible for RTase activity, and
- the RNase H domain from approximately position 680 to the C-terminus (approximately position 832) is involved in RNase H activity.

Four residues have been involved in the RTase activity, forming a motif "YMDD" (for Tyr, Met, Asp and Asp residues) generally present from approximately position 538 to approximately position 541 of a native HBV polymerase (e.g. corresponding to positions 538, 539, 540 and 541 in SEQ ID NO: 1 and to positions 492, 493, 494 and 495 in SEQ ID NO: 7) and the present invention encompasses any mutation(s) in this motif or elsewhere in the RTase domain that correlate with a significant reduction (i.e. at least a 10 fold reduction) or ablation of the RTase activity while retaining immunogenic properties. Representative examples of suitable RTase-deficient polymerase mutants are described in the literature, e.g. in Radziwill et al. (1990, J. Virol. 64:613), in Bartenschlager et al. (1990, J. Virol. 64:5324) and in Jeong et al. (1996, Biochem Bioph Res Commun. 223(2):264). Preferably, the polymerase moiety in use in the present invention comprises the substitution of the first Asp residue of the YMDD motif (corresponding to position 540 in SEQ ID NO: 1 and to position 494 of SEQ ID NO: 7) or of the amino acid residue located in an equivalent position in a native HBV polymerase to any amino acid residue other than Asp, with a special preference for a substitution to a His residue (D540H mutation). Reduction or ablation of RTase activity can be performed using assays well known in the art (e.g. the endogenous polymerase assays described in Radziwill et al., 1990, J Virol. 64:613).

Alternatively or in combination, the polymerase moiety in use in the present invention is modified so as to exhibit a reduced RNase H enzymatic activity with respect to a native HBV polymerase. Advantageously, said reduction of RNase H activity is provided by one or more mutation(s) in the domain responsible for RNase H enzymatic activity. As discussed above, the functional domain involved in RNase H activity has been mapped within the C-terminal portion of HBV polymerase, more particularly from position 680 to the C-terminal position 832 and the present invention encompasses any mutation(s) in this domain that correlate with a significant reduction (i.e. at least a 10 fold reduction) or ablation of the RNase H activity and which is not deleterious to immunogenic properties. Representative examples of suitable RNase H-deficient polymerase mutants are described in the literature, e.g. in Radziwill et al. (1990, J. Virol. 64:613), in Bartenschlager at al. (1990, J. Virol. 64:5324). Preferably, the polymerase moiety in use in the present invention comprises the substitution of the Glu residue corresponding to position 718 in SEQ ID NO: 1 and to position 672 of SEQ ID NO: 7 or of the amino acid residue located in an equivalent position in a native HBV polymerase to any amino acid residue other than Glu, with a special preference for a substitution to a His residue (E718H mutation). Reduction or ablation of RNase H activity can be performed using assays well known in the art (e.g. in vitro RNaseH activity assays or DNA-RNA tandem molecule analysis described in Radziwill et al., 1990, J Virol. 64:613 or in Lee et al., 1997, Biochem. Bioph. Res. Commun. 233(2):401).

Preferably, the polymerase moiety in use in the present invention is mutated so as to reduce or ablate both the RTase and the RNase activities and comprises the modifications discussed above in connection with these enzymatic functions, with a special preference for mutations D540H and E718H.

A preferred embodiment of the present invention is directed to a polymerase moiety comprising, alternatively essentially consisting of or alternatively consisting of an amino acid sequence which exhibits at least 80% of identity, advantageously at least 85% of identity, preferably at least 90% of identity, more preferably at least 95% of identity, and even more preferably 100% identity with the amino acid sequence shown in SEQ ID NO: 8 or with the amino acid sequence shown in SEQ ID NO: 7 with the substitution of the Asp residue in position 494 to an His residue and the substitution of the Glu residue in position 672 to an His residue.

In another and preferred embodiment, the polymerase moiety in use in the present invention is fused in frame to heterologous hydrophobic sequence(s) so as to improve synthesis, and/or stability, and/or presentation at the surface of the expressing host cells and/or presentation to host's MHC class I and/or MHC class II antigens. Suitable heterologous hydrophobic sequences include sequences such as signal and/or trans-membrane peptides permitting to target the polymerase moiety in the secretion pathway. Such peptides are known in the art. Briefly, signal peptides are generally present at the N-terminus of membrane-presented or secreted polypeptides and initiate their passage into the endoplasmic reticulum (ER). They comprise 15 to 35 essentially hydrophobic amino acids which are then removed by a specific ER-located endopeptidase to give the mature polypeptide. Trans-membrane peptides are usually highly hydrophobic in nature and serve to anchor the polypeptides in the cell membrane (see for example Branden and Tooze, 1991, in Introduction to Protein Structure p. 202-214, NY Garland; WO99/03885). The choice of the trans-membrane and/or signal peptides which can be used in the context of the present invention is vast. They may be obtained from any membrane-anchored and/or secreted polypeptide (e.g. cellular or viral polypeptides) such as those of immunoglobulins, tissue plasminigen activator, insulin, rabies glycoprotein, the HIV virus envelope glycoprotein or the measles virus F protein or may be synthetic. The preferred site of insertion of the signal peptide is the N-terminus downstream of the codon for initiation of translation and that of the trans-membrane peptide is the C-terminus, for example immediately upstream of the stop codon. Moreover, a linker peptide can be used to connect the signal and/or trans-membrane peptides to the polymerase moiety.

Other hydrophobic sequence(s) can be employed in the context of the invention, such as those generally present in envelope or membrane bound proteins, including HBsAg. Of particular interest in the context of the present invention is the fusion of the polymerase moiety with one or more of the immunogenic domains described herein (env1, env2, env3 and/or env4) which are of hydrophobic nature. The one or more hydrophobic domain(s) can be fused in frame at the N-terminus, at the C-terminus or within the polymerase moiety.

Preferably, in the context of the invention, the polymerase moiety in use in the invention is fused in frame to the signal and trans-membrane peptides of the rabies glycoprotein. As illustrated in the appended example section, said rabies signal sequence is fused in frame at the N terminus and said rabies transmembrane sequence is fused in frame at the C-terminus of said polymerase moiety. A most preferred embodiment is directed to a polymerase moiety comprising, alternatively essentially consist of, or alternatively consists of an amino acid sequence which exhibits at least 80% of identity, advantageously at least 85% of identity, particularly at least 90% of identity, preferably at least 95% of identity and more preferably 100% identity with the amino acid sequence shown in SEQ ID NO: 9.

Core Moiety

Alternatively or in combination with the composition described above, the present invention also provides a composition comprising a core moiety originating from a second HBV. As described herein in connection with HBV virus, the core moiety in use in the invention originates from an HBV which is the same or different of the HBV virus from which originates the polymerase moiety. Preferably, the core and the polymerase moieties both originate from a genotype D HBV, with a special preference for the Y07587 HBV isolate or alternatively, from a HBV genotype prevalent in China (e.g. genotype B or C).

According to one embodiment, the core moiety in use in this invention can be a native HBV core (e.g. that shown in SEQ ID NO: 2) or a modified core as compared to the corresponding native HBV core that retains at least 100 amino acid residues of a core protein, with a specific preference for a core moiety comprising from 120 to 180 amino acid residues, desirably from 125 to 148 amino acid residues and preferably from 130 to 143 amino acid residues (e.g. approximately 140 amino acid residues).

An appropriate modification is a truncation. Desirably, the truncation encompasses at least 10 amino acid residues and at most 40 amino acid residues normally present at the C-terminus of a native HBV core or within the C-terminal part (i.e. the portion encompassing the last 40 amino acid residues). This modification is particularly relevant for compositions of the invention also comprising a polymerase moiety so as to reduce or delete the overlapping portions between polymerase and core moieties. It may also be relevant for deleting a NLS (nuclear localization signal) within this region of core and/or for inhibiting interaction with HBV polymerase. It is within the reach of the skilled person to adapt the truncation to the composition of the invention within the recited range at least 10 amino acid residues and at most 40 amino acid residues. Appropriate truncations include 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or40 consecutive amino acid residues normally present at the C-terminus of a native HBV core or within its C-terminal portion. With respect to a native HBV core, the core moiety used in the context of the present invention is advantageously truncated by at least 20 amino acid residues and at most 40 amino acid residues, preferably by at least 30 amino acid residues and at most 38 amino acid residues, and more preferably by at least 34 amino acid residues and at most 37 amino acid residues located at the C-terminus of a native HBV or within the C-terminal part with a special preference for a truncation including the last 35 amino acid residues of a native HBV core (in other terms, the truncation extends from approximately position 149 to the C-terminus of the core polypeptide).

Of particular interest is a core moiety comprising an amino acid sequence which exhibits at least 80% of identity, advantageously at least 85% of identity, preferably at least 90% of identity, more preferably at least 95% of identity, and even more preferably 100% identity with the portion of the amino acid sequence shown in SEQ ID NO: 2 extending from position 1 to approximately position 148 and even more preferably a core moiety comprising an amino acid sequence which exhibits at least 80% of identity, advantageously at least 85% of identity, preferably at least 90% of identity, more preferably at least 95% of identity, and even more preferably 100% identity with the amino acid sequence shown in SEQ ID NO: 10.

Alternatively or in combination, the core moiety is modified so as to exhibit a reduced recognition of and/or interaction with an HBV envelope protein with respect to a native HBV core. Advantageously, said reduction of recognition/interaction is provided by one or more mutation(s) in a region located internally in the vinicity of residue 80 that is predicted to form an outer loop exposed on the surface of core particles (Argos et al., 1988, EMBO J. 7:819). Reduction or ablation of recognition of or interaction with a env protein can be performed using assays well known in the art (such as electron microscopy, analysis of nucleocapsids formation in cells, secreted virions following transient transfection in HuH7, as described in Seitz et al., 2007, EMBO J., 26: 416 or in Ponsel et al., 2003, J. Virol. 77(1): 416).

A preferred modification comprises deletion of one or more amino acid residues in the region of the core extending from approximately position 75 to approximately position 85 (corresponding to residues 75-85 of SEQ ID NO: 2 and SEQ ID NO: 10), with a special preference for the deletion of the portion of the core moiety extending from approximately position 77 to approximately position 84 (corresponding to residues 77-84 of SEQ ID NO: 2 and SEQ ID NO: 10). A preferred core moiety comprises, alternatively essentially consists of or alternatively consists of an amino acid sequence which exhibits at least 80% of identity, advantageously at least 85% of identity, preferably at least 90% of identity, more preferably at least 95% of identity, and even more preferably 100% identity with the amino acid sequence shown in SEQ ID NO: 11 or with the amino acid sequence shown in SEQ ID NO: 2 lacking residues 77-84.

Env Moiety

Alternatively or in combination with the composition described above, the present invention also provides a composition comprising an env moiety. Said env moiety comprises one or more immunogenic domain(s) of at least 15 consecutive amino acid residues present in a HBs protein originating from a third HBV virus. Preferably, each of said immunogenic domains corresponds to a portion of at least 20 amino acids and at most 100 amino acids present in a HBsAg protein either a native one or a modified one (e.g. modified so as to be representative of a specific genotype). Each of the immunogenic domains can originate from the same or different HBV virus(es) which can be the same or different with respect to HBV viruses from which originate the core and polymerase moieties. Preferably, each of the env immunogenic domains originates from a genotype D HBV, and especially from the Y07587 HBV isolate or alternatively, from a HBV genotype prevalent in China (e.g. genotype B or C).

Advantageously, each of the one or more immunogenic domains comprises T cell epitopes specific for T helper ($T_H$) cells and/or for cytotoxic T (CTL) cells which can be restricted to various MHC class I and/or class II antigens (e.g. A2, A24, DR, DP, etc). Such epitopes have been described in the art (WO93/03764; WO94/19011; Desombere et al., 2000, Clin. Exp. Immunol 122:390; Loirat et al., 2000, J. Immunol. 165:4748; Schirmbeck et al., 2002, J. Immunol 168:6253; Depla et al., 2008, J. Virol. 82: 435) and it is within the reach of the skilled person to design suitable immunogenic domain(s) as described herein within the recited range of 15 to 100 amino acid residues which include(s) B, $T_H$ and/or CTL epitopes from a native env protein (e.g. that shown in SEQ ID NO: 3). Preferably, the env moiety comprised in or encoded by the composition of the invention does not include any immunogenic domain(s) originating from preS 1 and preS2 regions.

The present invention encompasses env moiety comprising one immunogenic domain as well as those comprising two, three or more.

Desirably, the one or more immunogenic domain(s) in use in the present invention is/are selected from the group consisting of:
The portion of an env protein (HBsAg) extending from position 14-51 (env 1 domain);
The portion of an env protein (HBsAg) extending from position 165-194 (env 2 domain);
The portion of an env protein (HBsAg) extending from position 81-106 (env 3 domain);
The portion of an env protein (HBsAg) extending from position 202-226 (env 4 domain); and
Any combination thereof.

Particularly suitable immunogenic domain(s) for use in the present invention comprises, alternatively essentially consists of or alternatively consists of an amino acid sequence which exhibits at least 80% of identity, advantageously at least 85% of identity, preferably at least 90% of identity, more preferably at least 95% of identity, and even more preferably 100% identity with any of the amino acid sequences shown in SEQ ID NO: 12-15.

In the context of the invention, the combination of immunogenic domains can be in the form of a mixture of individual immunogenic domains in the composition of the invention or in the form of a fusion in frame between two or more immunogenic domains in any arrangement possible (e.g. fusion or mixture of env1-env2, env2-env1, env1-env3, env3-env1, env1-env4, env4-env1, env2-env-3, env3-env2, env2-env4, env4-env2, env3-env4, env4-env3, env1-env2-env3, env2-env1-env3, env1-env2-env4, etc.). Moreover, the combination can comprise a single copy or several copies thereof (e.g. env1-env-2-env1, env1-env-4, env1, etc. The fusion between each immunogenic domain can be direct or through a linker.

Env moieties of particular interest in the context of the invention comprise the fusion of two or three immunogenic domains shown in SEQ ID NO: 12-15, with a special preference for an env1-env2 fusion comprising, alternatively essentially consisting of or alternatively consisting of an amino acid sequence which exhibits at least 80% of identity, advantageously at least 85% of identity, preferably at least 90% of identity, more preferably at least 95% of identity, and even more preferably 100% identity with the amino acid sequence shown in SEQ ID NO: 16 or an env1-env2-env4 fusion comprising, alternatively essentially consisting of or alternatively consisting of an amino acid sequence which exhibits at least 80% of identity, advantageously at least 85% of identity, preferably at least 90% of identity, more preferably at least 95% of identity, and even more preferably 100% identity with the amino acid sequence shown in SEQ ID NO: 17.

According to a specific embodiment, the polymerase, core and/or env moieties comprised in or encoded by the composition of the invention can be fused in frame by pairs or all together. For example, one may envisage the fusion of the polymerase and env moieties in a single polypeptide chain. Alternatively, the core and env moieties can be fused in frame in a single polypeptide chain. Here again, the encoding nucleic acid sequences can be fused either directly or through a linker. Advantageously, the env moiety is fused in frame to the C-terminus of the core or polymerase moiety.

Preferred examples of fusion polypeptides of the core moiety with the env moiety are selected from the group consisting of:
A polypeptide comprising, or alternatively consisting essentially of, or alternatively consisting of an amino acid sequence which exhibits at least 80% of identity, advantageously at least 85% of identity, preferably at least 90% of identity, more preferably at least 95% of identity, and even more preferably 100% identity with the amino acid sequence shown in SEQ ID NO: 18 (core*t-env1);

A polypeptide comprising, or alternatively consisting essentially of, or alternatively consisting of an amino acid sequence which exhibits at least 80% of identity, advantageously at least 85% of identity, preferably at least 90% of identity, more preferably at least 95% of identity, and even more preferably 100% identity with the amino acid sequence shown in SEQ ID NO: 19 (core*t-env1-env2); and A polypeptide comprising, or alternatively consisting essentially of, or alternatively consisting of an amino acid sequence which exhibits at least 80% of identity, advantageously at least 85% of identity, preferably at least 90% of identity, more preferably at least 95% of identity, and even more preferably 100% identity with the amino acid sequence shown in SEQ ID NO: 20 (core-env1-env2-env4) or with the portion of the amino acid sequence shown in SEQ ID NO: 20 starting at residue 1 and ending at residue 251 (core-env1-env2) or with the portion of the amino acid sequence shown in SEQ ID NO: 20 starting at residue 1 and ending at residue 221 (core-env1); or deleted versions thereof lacking residues 77-84 in the core moiety.

In the context of the invention, the polymerase moiety, the core moiety and/or the env moiety comprised or encoded by the composition of the invention may further comprise additional modifications. Suitable modifications are those which are beneficial to the synthesis, processing, stability and solubility of the resulting polypeptide (e.g. those aimed to modify potential cleavage sites, potential glycosylation sites and/or membrane anchorage as described herein) as well as those which are beneficial to the immunogenicity of the resulting composition (e.g. incorporation or fusion with one or more compounds capable of enhancing immunogenic properties). Such compounds capable of enhancing immunogenic properties have been described in the literature and include, without limitation, calreticulin (Cheng et al., 2001, J. Clin. Invest. 108:669), *Mycobacterium tuberculosis* heat shock protein 70 (HSP70) (Chen et al., 2000, Cancer Res. 60:1035), ubiquitin (Rodriguez et al., 1997, J. Virol. 71:8497), bacterial toxin such as the translocation domain of *Pseudomonas aeruginosa* exotoxin A (ETA(dIII)) (Hung et al., 2001 Cancer Res. 61:3698) as well as T helper epitope(s) such as Pan-Dr peptide (Sidney et al., 1994, Immunity 1:751), pstS 1 GCG epitope (Vordermeier et al., 1992, Eur. J. Immunol. 22:2631), tetanus toxoid peptides P2TT (Panina-Bordignon et al., 1989, Eur. J. Immunol. 19:2237) and P30TT (Demotz et al., 1993, Eur. J. Immunol. 23:425), influenza epitope (Lamb et al., 1982, Nature 300:66) and hemaglutinin epitope (Rothbard et al., 1989, Int. Immunol. 1:479).

Nucleic Acid Molecule

The present invention also provides isolated nucleic acid molecules encoding independently or in combination the polymerase, core and env moieties in use in the present invention as well as compositions comprising such nucleic acid molecule(s).

Of particular interest are:

Nucleic acid molecules which encode polymerase moieties as described herein, with a special preference for those comprising the amino acid sequence shown in any of SEQ ID NO: 7, 8, 9 or the amino acid sequence shown in SEQ ID NO: 7 with the substitution of the Asp residue in position 494 to an His residue and the substitution of the Glu residue in position 672 to an His residue;

Nucleic acid molecules which encode core moieties described herein, with a special preference for those comprising the amino acid sequence shown in SEQ ID NO: 10 or 11;

Nucleic acid molecules which encode env moieties described herein, with a special preference for those comprising the amino acid sequence shown in any of SEQ ID NO: 12-17; and Nucleic acid molecules which encode fused core and env moieties described herein, with a special preference for those comprising the amino acid sequence shown in any of SEQ ID NO: 18, 19 or 20 or the portion of the amino acid sequence shown in SEQ ID NO: 20 starting at residue 1 and ending at residue 251 (core-env1-env2) or the portion of the amino acid sequence shown in SEQ ID NO: 20 starting at residue 1 and ending at residue 221 (core-env1); or deleted versions thereof lacking core residues 77-84 of SEQ ID NO: 20.

Desirably, the nucleic acid molecules of the invention can be optimized for providing high level expression in a particular host cell or organism, e.g. mammalian, yeast (e.g. *Saccharomyces cerevisiae, Saccharomyces pombe* or *Pichia pastoris*) or bacteria (e.g. *E. coli, Bacillus subtilis* or *Listeria*). It has been indeed observed that, when more than one codon is available to code for a given amino acid, the codon usage patterns of organisms are highly non-random (see for example Wada et al., 1992, Nucleic Acids Res. 20:2111) and the utilisation of codons may be markedly different between different hosts (see for example Nakamura et al., 1996, Nucleic Acids Res. 24:214). As the nucleotide sequences used in the invention are mostly of viral origin (HBV), they may have an inappropriate codon usage pattern for efficient expression in host cells such as bacterial, lower or higher eukaryotic cells. Typically, codon optimisation is performed by replacing one or more "native" (e.g. HBV) codon corresponding to a codon infrequently used in the host cell of interest by one or more codon encoding the same amino acid which is more frequently used. It is not necessary to replace all native codons corresponding to infrequently used codons since increased expression can be achieved even with partial replacement. Moreover, some deviations from strict adherence to optimised codon usage may be made to accommodate the introduction of restriction site(s) into the resulting nucleic acid molecule.

Further to optimization of the codon usage, expression in the host cell or organism can further be improved through additional modifications of the nucleotide sequence. For example, the nucleic acid molecule of the invention can be modified so as to prevent clustering of rare, non-optimal codons being present in concentrated areas and/or to suppress or modify at least partially negative sequence elements which are expected to negatively influence expression levels. Such negative sequence elements include without limitation the regions having very high (>80%) or very low (<30%) GC content; AT-rich or GC-rich sequence stretches; unstable direct or inverted repeat sequences; RNA secondary structures; and/or internal cryptic regulatory elements such as internal TATA-boxes, chi-sites, ribosome entry sites, and/or splicing donor/acceptor sites. Another embodiment of the invention pertains to fragments of the nucleic acid molecule of the invention, e.g. restriction endonuclease and PCR-generated fragments. Such fragments can be used as probes, primers or fragments encoding an immunogenic portion of the first and/or second polypeptide.

A preferred nucleic acid molecule according to the invention is selected from the group consisting of:
- A nucleic acid molecule comprising a nucleotide sequence which exhibits at least 80% of identity with the nucleotide sequence shown in SEQ ID NO: 21 (encoding the truncated Pol of SEQ ID NO: 7);
- A nucleic acid molecule comprising a nucleotide sequence which exhibits at least 80% of identity with the nucleotide sequence shown in SEQ ID NO: 22 (encoding the mutated Pol of SEQ ID NO: 8);
- A nucleic acid molecule comprising a nucleotide sequence which exhibits at least 80% of identity with the nucleotide sequence shown in SEQ ID NO: 21 with the substitution of the G nucleotide in position 1480 to a C, of the G nucleotide in position 2014 to a C and of the A nucleotide in position 2016 to a T (encoding the truncated Pol of SEQ ID NO: 7 with the substitution of the D540H and E718H mutations);
- A nucleic acid molecule comprising a nucleotide sequence which exhibits at least 80% of identity with the nucleotide sequence shown in SEQ ID NO: 23 (encoding the truncated and mutated Pol-TMR of SEQ ID NO: 9);
- A nucleic acid molecule comprising a nucleotide sequence which exhibits at least 80% of identity with the nucleotide sequence shown in SEQ ID NO: 24 (encoding core*t-env1 of SEQ ID NO: 18);
- A nucleic acid molecule comprising a nucleotide sequence which exhibits at least 80% of identity with the nucleotide sequence shown in SEQ ID NO: 25 (encoding core*t-env1-env2 of SEQ ID NO: 19); and
- A nucleic acid molecule comprising a nucleotide sequence which exhibits at least 80% of identity with the nucleotide sequence shown in SEQ ID NO: 26 (encoding core-env1-env2-env4 of SEQ ID NO: 20) or with the portion of the nucleotide sequence shown in SEQ ID NO: 26 starting at nucleotide 1 and ending at nucleotide 753 (encoding core-env1-env2) or with the portion of the nucleotide sequence shown in SEQ ID NO: 26 starting at nucleotide 1 and ending at nucleotide 663 (encoding core-env1); or deleted versions thereof lacking the portion extending from the G in position 229 to the A in position 252 of SEQ ID NO: 26 (corresponding to deletion of residues 77-84 in the core moiety).

The nucleic acid molecules of the present invention can be generated using sequence data accessible in the art and the sequence information provided herein. The DNA sequence coding for each of the HBV polypeptides can be isolated directly from HBV-containing cells, cDNA and genomic libraries, viral genomes or any prior art vector known to include it, by conventional molecular biology or PCR techniques, and can be modified (e.g. as described herein). Alternatively, the nucleic acid molecule of the invention can also be generated by chemical synthesis in automatised process (e.g. assembled from overlapping synthetic oligonucleotides as described for example in Edge, 1981, Nature 292, 756; Nambair et al., 1984, Science 223:1299; Jay et al., 1984, J. Biol. Chem. 259:6311).

Also provided by the present invention are vectors comprising one or more nucleic acid molecule(s) of the present invention as well as compositions comprising such vector(s).

A variety of host-vector systems may be used in the context of the present invention, including bacteriophage, plasmid or cosmid vectors adapted to expression in prokaryotic host organisms such as bacteria (e.g. *E. coli, Bacillus subtilis* or *Listeria*); vectors adapted to expression in yeast (e.g. *Saccharomyces cerevisiae, Saccharomyces pombe, Pichia pastoris*); virus expression vectors (e.g. baculovirus) adapted to expression in insect cell systems (e.g. Sf 9 cells); virus or plasmid expression vectors (e.g. Ti plasmid, cauliflower mosaic virus CaMV; tobacco mosaic virus TMV) adapted to expression in plant cell systems; as well as plasmid and viral vectors adapted to expression in higher eukaryotes cells or organisms. Such vectors are largely described in the literature and commercially available (e.g. in Stratagene, Amersham Biosciences, Promega, etc.). Representative examples of suitable plasmid vectors include, without limitation, pREP4, pCEP4 (Invitrogene), pCI (Promega), pCDM8 (Seed, 1987, Nature 329, 840) and pMT2PC (Kaufman et al., 1987, EMBO J. 6:187), pVAX and pgWiz (Gene Therapy System Inc; Himoudi et al., 2002, J. Virol. 76:12735). A number of viral vectors can also be utilized in the context of the invention derived from a variety of different viruses (e.g. retrovirus, adenovirus, AAV, poxvirus, herpes virus, measle virus, foamy virus, alphavirus, vesicular *stomatis* virus and the like).

Of particular interest are adenoviral vectors which have a number of well-documented advantages for gene transfer or for recombinant production (for a review, see "Adenoviral vectors for gene therapy", 2002, Ed D. Curiel and J. Douglas, Academic Press). The adenoviral vectors for use in accordance with the present invention can be derived from a variety of human or animal sources (e.g. canine, ovine, simian adenovirus, etc). Any serotype can be employed with a special preference for human adenoviruses and a specific preference for subgenus C such as Ad2 (Ad2), 5 (Ad5), 6 (Ad6), subgenus B such as 11 (Ad11), 34 (Ad34) and 35 (Ad35) and subgenus D such as 19 (Ad19), 24 (Ad24), 48 (Ad48) and 49 (Ad49). It may also be advantageous to use animal Ad with a special preference for chimp Ad, such as chimp Ad3 (Peruzzi et al., 2009, Vaccine 27:1293) and chimp Ad63 (Dudareva et al., 2009, vaccine 27:3501) The cited adenovirus are available from the American Type Culture Collection (ATCC, Rockville, Md.) or have been the subject of numerous publications describing their sequence, organization and methods of producing, allowing the artisan to apply them (see for example U.S. Pat. Nos. 6,133,028; 6,110,735; WO 02/40665; WO 00/50573; EP 1016711; Vogels et al., 2003, J. Virol. 77:8263; WO00/70071; WO02/40665; WO2004/001032; WO2004/083418; WO2004/097016; WO2005/010149).

In one embodiment, the adenoviral vector of the present invention is replication-defective. Preferred replication-defective adenoviral vectors are E1-defective (see for example U.S. Pat. Nos. 6,136,594 and 6,013,638), with an E1 deletion extending from approximately positions 459 to 3328 or from approximately positions 459 to 3510 (by reference to the sequence of the human adenovirus type 5 disclosed in the GeneBank under the accession number M 73260 and in Chroboczek et al., 1992, Virol. 186:280). The cloning capacity can further be improved by deleting additional portion(s) of the adenoviral genome (all or part of the non essential E3 region or of other essential E2, E4 regions as described in WO94/28152; Lusky et al., 1998, J. Virol 72:2022).

The nucleic acid molecule(s) of the present invention can be inserted in any location of the adenoviral genome, with a specific preference for insertion in replacement of the E1 region. It/they may be positioned in sense or antisense orientation relative to the natural transcriptional direction of the region in question.

Other suitable viral vectors in the context of the invention are derived from poxviruses (see for example Cox et al. in "Viruses in Human Gene Therapy" Ed J. M. Hos, Carolina Academic Press). In the context of the present invention, a poxviral vector may be obtained from any member of the poxviridae, in particular canarypox, fowlpox and vaccinia virus, the latter being preferred. Suitable vaccinia viruses include without limitation the Copenhagen strain (Goebel et al., 1990, Virol. 179:247 and 517; Johnson et al., 1993, Virol. 196:381), the Wyeth strain and the modified Ankara (MVA) strain (Antoine et al., 1998, Virol. 244:365). The general conditions for constructing recombinant poxvirus are well known in the art (see for example EP 206 920; Mayr et al., 1975, Infection 3:6; Sutter and Moss, 1992, Proc. Natl. Acad. Sci. USA 89:10847; U.S. Pat. No. 6,440,422). The nucleic acid molecule of the present invention is preferably inserted within the poxviral genome in a non-essential locus. Thymidine kinase gene is particularly appropriate for insertion in Copenhagen vaccinia vectors (Hruby et al., 1983, Proc. Natl. Acad. Sci USA 80:3411; Weir et al., 1983, J. Virol. 46:530) and deletion II or III for insertion in MVA vector (Meyer et al., 1991, J. Gen. Virol. 72:1031; Sutter et al., 1994, Vaccine 12:1032).

The present invention also encompasses vectors (e.g. plasmid DNA) complexed to lipids or polymers to form particulate structures such as liposomes, lipoplexes or nanoparticles. Such technologies are available in the art (see for example Arangoa et al., 2003, Gene Ther. 10:5; Eliaz et al., 2002, Gene Ther. 9:1230 and Betageri et al., 1993, "Liposome drug delivery systems", Technomic Publishing Company, Inc).

According to a preferred embodiment, the vectors of the invention comprise the nucleic acid molecule(s) of the invention in a form suitable for expression in a host cell or organism, which means that the nucleic acid molecule(s) is/are placed under the control of one or more regulatory sequences, appropriate to the vector and/or the host cell. It will be appreciated by those skilled in the art that the choice of the regulatory sequences can depend on such factors as the host cell, the level of expression desired, etc.

The promoter is of special importance and suitable promoters useful in the context of the present invention include constitutive promoters which direct expression of the nucleic acid molecule(s) in many types of host cell and those which direct expression of the nucleic acid molecule(s) only in certain host cells (e.g. liver-specific regulatory sequences) or in response to specific events or exogenous factors (e.g. by temperature, nutrient additive, hormone or other ligand).

Promoters suitable for constitutive expression in mammalian cells include but are not limited to the cytomegalovirus (CMV) immediate early promoter (Boshart et al., 1985, Cell 41:521), the RSV promoter, the adenovirus major late promoter, the phosphoglycero kinase (PGK) promoter (Adra et al., 1987, Gene 60:65), and the thymidine kinase (TK) promoter of herpes simplex virus (HSV)-1. Vaccinia virus promoters are particularly adapted for expression in poxviral vectors. Representative example include without limitation the vaccinia 7.5K, H5R, 11K7.5 (Erbs et al., 2008, Cancer Gene Ther. 15:18), TK, p28, p11 and K1L promoter, as well as synthetic promoters such as those described in Chakrabarti et al. (1997, Biotechniques 23:1094, in connection with the pSE/L promoter), Hammond et al. (1997, J. Virological Methods 66:135) and Kumar and Boyle (1990, Virology 179:151) as well as early/late chimeric promoters. Liver-specific promoters include without limitation those of HMG-CoA reductase (Luskey, 1987, Mol. Cell. Biol. 7:1881); sterol regulatory element 1 (SRE-1; Smith et al., 1990, J. Biol. Chem. 265:2306); albumin (Pinkert et al., 1987, Genes Dev. 1:268); phosphoenol pyruvate carboxy kinase (PEPCK) (Eisenberger et al., 1992, Mol. Cell Biol. 12:1396); human C-reactive protein (CRP) (Li et al., 1990, J. Biol. Chem. 265:4136); human glucokinase (Tanizawa et al., 1992, Mol. Endocrinology 6:1070); cholesterol 7-alpha hydroylase (CYP-7) (Lee et al., 1994, J. Biol. Chem. 269: 14681); alpha-1 antitrypsin (Ciliberto et al., 1985, Cell 41:531); insulin-like growth factor binding protein (IGFBP-1) (Babajko et al., 1993, Biochem Biophys. Res. Comm. 196:480); human transferrin (Mendelzon et al., 1990, Nucleic Acids Res. 18:5717); collagen type I (Houglum et al., 1994, J. Clin. Invest. 94:808) and FIX (U.S. Pat. No. 5,814,716) genes.

Those skilled in the art will appreciate that the regulatory elements controlling the expression of the nucleic acid molecule(s) of the invention may further comprise additional elements for proper initiation, regulation and/or termination of transcription (e.g. polyA transcription termination sequences), mRNA transport (e.g. nuclear localization signal sequences), processing (e.g. splicing signals), and stability (e.g. introns and non-coding 5' and 3' sequences), translation (e.g. an initiator Met, tripartite leader sequences, ribosome binding sites, Shine-Dalgarno sequences, etc.) into the host cell or organism and purification steps (e.g. a tag).

In accordance with the present invention, the nucleic acid molecules of the present invention encoding said polymerase moiety, said core moiety and/or said env moiety can be carried by the same vector or at least two vectors (e.g. two or three independent vectors). Thus the present invention encompasses a vector that carries the nucleic acid molecules encoding said polymerase moiety, said core moiety and said env moiety as well as independent vectors, each carrying only one or two of the nucleic acid molecules encoding said polymerase moiety, said core moiety and said env moiety. Such vector(s) are also provided by the present invention as well as compositions comprising such vector(s). When using different vectors, they can be from different origin or from the same origin. For example, one may envisage expression of one HBV moiety from a defective poxvirus (e.g. MVA) and expression of the two other moieties from another poxvirus vector (e.g. a Copenhagen vector). As another example, one may envisage a composition comprising an adenoviral vector encoding the polymerase moiety and an adenoviral vector encoding the core and env moieties. Alternatively, expression from different viral vectors (e.g. expression of the polymerase moiety from an adenoviral vector and expression of core and/or env moieties from MVA or vice versa) is also suitable in the context of the invention as well as expression of the HBV moieties from plasmid and viral vector(s).

Preferred embodiments of the invention are directed to vectors selected from the group consisting of:
(i) A MVA vector comprising a nucleic acid molecule placed under the control of a vaccinia promoter such as the 7.5K promoter, and encoding a polymerase moiety comprising an amino acid sequence as shown in SEQ ID NO: 7, 8 or 9 or in SEQ ID NO: 7 with the substitution of the Asp residue in position 494 to an His residue and the substitution of the Glu residue in position 672 to an His residue. Preferably, said nucleic acid molecule is inserted in deletion III of the MVA genome.
(ii) A MVA vector comprising a nucleic acid molecule placed under the control of a vaccinia promoter such as the pH5r promoter and encoding a core moiety and an env moiety comprising an amino acid sequence as shown in SEQ ID NO: 18 or 19. Preferably, said nucleic acid molecule is inserted in deletion III of the MVA genome.

(iii) An E1-defective Ad vector comprising inserted in place of the E1 region a nucleic acid molecule placed under the control of the CMV promoter and encoding a polymerase moiety comprising an amino acid sequence as shown in SEQ ID NO: 7, 8 or 9 or in SEQ ID NO: 7 with the substitution of the Asp residue in position 494 to an His residue and the substitution of the Glu residue in position 672 to an His residue.

(iv) An E1-defective Ad vector comprising inserted in place of the E1 region a nucleic acid molecule placed under the control of the CMV promoter and encoding a core moiety and an env moiety comprising an amino acid sequence as shown in SEQ ID NO: 18, 19 or 20 or the portion of SEQ ID NO: 20 starting at residue 1 and ending at residue 251 (core-env1-env2) or the portion of SEQ ID NO: 20 starting at residue 1 and ending at residue 221 (core-env1).

As well as to a composition comprising vectors (i) and (ii) or (iii) and (iv).

If needed, the vector or composition of the invention can further comprise one or more transgene(s), e.g. a gene of interest to be expressed together with the nucleic acid molecule(s) of the invention in a host cell or organism. Desirably, the expression of the transgene has a therapeutic or protective activity to an HBV infection or any disease or condition caused by or associated with an HBV infection or is able to enhance immunogenicity of the composition of the invention. Suitable transgenes include without limitation one or more additional HBV polypeptide(s)/peptide(s) or encoding nucleic acid molecule(s) such as the X protein or fragment thereof, immunomodulators such as cytokine (e.g. IL-2, IL-7, IL-12, IL-15, IL-18, IL-21, IFNg), fusion of cytokines (such as those described in WO2005/14642) or their encoding nucleic acid molecules as well as suicide gene products or encoding nucleic acid molecules particularly useful in the context of treating liver carcinoma (such as cytosine deaminase (CDase), uracil phosphoribosyl transferase (UPRTase), the FCU-1 gene product (described in WO 99/54481) and derivatives thereof (described in WO2006/048768) which are to be used with the prodrug 5-fluorocytosine (5-FC). If a transgene is used, it can be expressed in the form of a fusion with any of the nucleic acid molecule of the invention or be expressed independently under the control of appropriate regulatory elements. Further, it can be inserted in any location of the vector of the invention or in an independent vector which is used in combination with the vector(s) or composition of the invention.

In another aspect, the present invention provides infectious viral particles comprising the nucleic acid molecules or vectors of the present invention as well as compositions comprising such infectious viral particles.

Typically, such viral particles are produced by a process comprising the steps of:

(a) introducing the viral vector of the invention into a suitable cell line,
(b) culturing said cell line under suitable conditions so as to allow the production of said infectious viral particle,
(c) recovering the produced infectious viral particle from the culture of said cell line, and
(d) optionally purifying said recovered infectious viral particle.

When the viral vector is defective, the infectious particles are usually produced in a complementation cell line or via the use of a helper virus, which supplies in trans the non functional viral genes. For example, suitable cell lines for complementing E1-deleted adenoviral vectors include the 293 cells (Graham et al., 1997, J. Gen. Virol. 36, 59-72) as well as the HER-96 and PER-C6 cells (e.g. Fallaux et al., 1998, Human Gene Ther. 9, 1909-1917; WO97/00326). Cells appropriate for propagating poxvirus vectors are avian cells, and most preferably primary chicken embryo fibroblasts (CEF) prepared from chicken embryos obtained from fertilized eggs.

The infectious viral particles may be recovered from the culture supernatant or from the cells after lysis. They can be further purified according to standard techniques (chromatography, ultracentrifugation in a cesium chloride gradient as described for example in WO96/27677, WO98/00524, WO98/22588, WO98/26048, WO00/40702, EP1016700 and WO00/50573).

The present invention also encompasses vectors or viral particles that have been modified to allow preferential targeting to a particular target cell (see for example Wickam et al., 1997, J. Virol. 71, 8221-8229; Arnberg et al., 1997, Virol. 227, 239-244; Michael et al., 1995, Gene Therapy 2, 660-668; WO94/10323; WO02/96939 and EP 1 146 125). A characteristic feature of targeted vectors and viral particles of the invention is the presence at their surface of a ligand capable of recognizing and binding to a cellular and surface-exposed component such as a cell-specific marker (e.g. an HBV-infected cell), a tissue-specific marker (e.g. a liver-specific marker), as well as a viral (e.g. HBV) antigen. Examples of suitable ligands include antibodies or fragments thereof directed to an HBV antigenic domain. Cell targeting can be carried out by genetically inserting the ligand into a polypeptide present on the surface of the virus (e.g. adenoviral fiber, penton, pIX or vaccinia p14 gene product).

The invention also relates to host cells which comprise the nucleic acid molecules, vectors or infectious viral particles of the invention as well as compositions comprising such host cells. In the context of the invention, host cells include prokaryotic cells, lower eukaryotic cells such as yeast, and other eukaryotic cells such as insect cells, plant and mammalian (e.g. human or non-human) cells as well as complementing cells capable of complementing at least one defective function of a replication-defective vector of the invention (e.g. adenoviral vector) such as 293 and PERC.6 cells.

According to a specific embodiment of the invention, the host cell can be further encapsulated. Cell encapsulation technology has been previously described (Tresco et al., 1992, ASAIO J. 38, 17-23; Aebischer et al., 1996, Human Gene Ther. 7, 851-860).

Still a further aspect of the present invention is a method for producing recombinant polymerase, core and/or env moieties, employing the vectors, infectious viral particles and/or host cells of the invention. The method of the present invention comprises (a) introducing a vector or an infectious viral particle of the invention into a suitable host cell to produce a transfected or infected host cell, (b) culturing in-vitro said transfected or infected host cell under conditions suitable for growth of the host cell, (c) recovering the polymerase, core and/or env moiety(ies) from the cell culture, and (d) optionally, purifying the recovered polypeptide(s).

It is expected that those skilled in the art are knowledgeable in the numerous expression systems available for producing the HBV moiety(ies) in appropriate host cells and of the methods for introducing a vector or an infectious viral particle into a host cell. Such methods include, but are not limited to, microinjection (Capechi et al., 1980, Cell 22:479), CaPO$_4$-mediated transfection (Chen and Okayama, 1987, Mol. Cell Biol. 7:2745), DEAE-dextran-mediated transfection, electroporation (Chu et al., 1987, Nucleic Acid Res. 15:1311), lipofection/liposome fusion (Felgner et al., 1987, Proc. Natl. Acad. Sci. USA 84:7413), particle bombardement (Yang et al., 1990, Proc. Natl. Acad. Sci. USA 87:9568), gene guns, transduction, viral infection as well as direct administration into a host organism via various means.

The vectors of the invention can be used in association with transfection reagents in order to facilitate introduction of the vector in the host cell, such as polycationic polymers (e.g. chitosan, polymethacrylate, PEI, etc) and cationic lipids (e.g.DC-Chol/DOPE, transfectam lipofectin now available from Promega). Moreover, as discussed above, recombinant DNA technologies can be used to improve expression of the nucleic acid molecule(s) in the host cell or organism, e.g. by using high-copy number vectors, substituting or modifying one or more transcriptional regulatory sequences (e.g. promoter, enhancer and the like), optimising the codon usage of the nucleic acid molecule(s) to the host cell, and suppressing negative sequences that may destabilize the transcript.

Host cells of the present invention can be cultured in conventional fermentation bioreactors, flasks, and petri plates. Culturing can be carried out at a temperature, pH and oxygen content appropriate for a given host cell. No attempts to describe in detail the various methods known for the production of proteins in prokaryote and eukaryote cells will be made here.

The HBV moiety(ies) can then be purified by well-known purification methods including ammonium sulfate precipitation, acid extraction, gel electrophoresis; filtration and chromatographic methods (e.g. reverse phase, size exclusion, ion exchange, affinity, phosphocellulose, hydrophobic-interaction, hydroxylapatite, or high performance liquid chromatography). The conditions and technology to be used depend on factors such as net charge, molecular weight, hydrophobicity, hydrophilicity and will be apparent to those having skill in the art. Moreover, the level of purification will depend on the intended use.

In another aspect, this invention provides a composition comprising at least one of the polymerase, core and/or env moiety(ies), the encoding nucleic acid molecules, the vector(s), the infectious viral particle(s), or the host cell of the invention (also referred herein to "active agent") or any combination thereof (e.g. combination of polypeptides or vectors/viral particles encoding various HBV moieties as described herein or combination of different genotypes). Preferably, the composition is a pharmaceutical composition which comprises a pharmaceutically acceptable vehicle further to a therapeutically effective amount of the active agent(s).

Suitably, the composition of the invention comprises a diluent appropriate for human or animal use. It is preferably isotonic, hypotonic or weakly hypertonic and has a relatively low ionic strength. Representative examples include sterile water, physiological saline (e.g. sodium chloride), Ringer's solution, glucose, trehalose or saccharose solutions, Hank's solution, and other aqueous physiologically balanced salt solutions (see for example the most current edition of Remington: The Science and Practice of Pharmacy, A. Gennaro, Lippincott, Williams & Wilkins). The composition of the invention is suitably buffered in order to be appropriate for human use at a physiological or slightly basic pH (e.g. from approximately pH 7 to approximately pH 9). Suitable buffers include without limitation phosphate buffer (e.g. PBS), bicarbonate buffer and/or Tris buffer.

The composition can also contain other pharmaceutically acceptable excipients for providing desirable pharmaceutical or pharmacodynamic properties, including for example modifying or maintaining the pH, osmolarity, viscosity, clarity, colour, sterility, stability, rate of dissolution of the formulation, modifying or maintaining release or absorption into an the human or animal organism, promoting transport across the blood barrier or penetration in a particular organ (e.g. liver). Suitable excipients include amino acids.

The pharmaceutically acceptable vehicles included in the composition of the invention must also permit to preserve its stability under the conditions of manufacture and long-term storage (i.e. at least one month) at freezing (e.g. −70° C., −20° C.), refrigerated (e.g. 4° C.) or ambient temperatures. In this respect, formulations which are particularly adapted to the composition of the invention include:

1M saccharose, 150 mM NaCl, 1 mM MgCl$_2$, 54 mg/l TWEEN 80 (Polysorbate 80), 10 mM Tris pH 8.5 (especially when the active agent is an adenoviral vector), and 10 mg/ml mannitol, 1 mg/ml HSA, 20 mM Tris, pH 7.2, and 150 mM NaCl physiological saline In addition, the composition of the invention may comprise one or more adjuvant(s) suitable for systemic or mucosal application in humans. Preferably, the adjuvant is capable of stimulating immunity to the composition of the invention, especially a T cell-mediated immunity e.g. through the toll-like receptors (TLR), such as TLR-7, TLR-8 and TLR-9. Representative examples of useful adjuvants include without limitation alum, mineral oil emulsion such as Freunds complete and incomplete (IFA), lipopolysaccharide or a derivative thereof (Ribi et al., 1986, Immunology and Immunopharmacology of Bacterial Endotoxins, Plenum Publ. Corp., NY, p407-419), saponins such as QS21 (Sumino et al., 1998, J. Virol. 72:4931; WO 98/56415), imidazo-quinoline compounds such as Imiquimod (Suader, 2000, J. Am Acad Dermatol. 43:S6), S-27609 (Smorlesi, 2005, Gene Ther. 12:1324) and related compounds such as those described in WO2007/147529, cytosine phosphate guanosine oligodeoxynucleotides such as CpG (Chu et al., 1997, J. Exp. Med. 186:1623; Tritel et al., 2003, J. Immunol. 171:2358) and cationic peptides such as IC-31 (Kritsch et al., 2005, J. Chromatogr Anal. Technol Biomed Life Sci 822:263).

The composition of the present invention is suitable for a variety of modes of administration, including systemic, topical and localized administration. Injection can be performed by any means, for example by subcutaneous, intradermal, intramuscular, intravenous, intraperitoneal, intratumoral, intravascular, intraarterial injection or by direct injection into an artery (e.g. by hepatic artery infusion) or a vein feeding liver (e.g. injection into the portal vein). Injections can be made with conventional syringes and needles, or any other appropriate devices available in the art. Alternatively the composition of the present invention may be administered via a mucosal route, such as the oral/alimentary, intranasal, intratracheal, intrapulmonary, intravaginal or intra-rectal route. Administration in the respiratory tract can be performed through nebulisation or aerosolization of droplet, spray, or dry powdered compositions using a pressured container (e.g. with a suitable propellant such as dichlorodifluoromethane, propane, nitrogen and the like), or in a non-pressurized dispenser. Topical administration can also be performed using transdermal means (e.g. patch and the like). In the context of the invention, a preferred composition is formulated for intramuscular and subcutaneous routes.

The composition of the invention can be in various forms, e.g. solid, liquid or frozen. Solid (e.g. dry powdered or lyophilized) compositions can be obtained by a process involving vacuum drying and freeze-drying. For mucosal administration, the compositions can be formulated as gastroresistant capsules and granules for oral administration, suppositories for rectal or vaginal administration, eventually in combination with absorption enhancers useful to increase the pore size of the mucosal membranes. Such absorption enhancers are typically substances having structural similarities to the phospholipid domains of the mucosal membranes such as sodium deoxycholate, sodium glycocholate, dimethyl-beta-cyclodextrin, lauryl-1-lysophosphatidylcholine).

The appropriate dosage can be adapted as a function of various parameters, in particular the mode of administration; the composition employed; the age, health, and weight of the host organism; the nature and extent of symptoms; kind of concurrent treatment; the frequency of treatment; and/or the need for prevention or therapy. Further refinement of the calculations necessary to determine the appropriate dosage for treatment is routinely made by a practitioner, in the light of the relevant circumstances. For general guidance, suitable dosage for a virus-comprising composition varies from about $10^5$ to about $10^{13}$ vp (viral particles), iu (infectious unit) or pfu (plaque-forming units) depending on the vector and the quantitative technique used. Techniques available to evaluate the quantity of vp, iu and pfu present in a sample are conventional in the art. For example, the number of adenoviral particles (vp) is usually determined by measuring the A260 absorbance, iu titers by quantitative DBP immunofuorescence and pfu by counting the number of plaques following infection of permissive cells. Preferably the vp/iu ratio is below 100 in accordance with FDA guidelines. Doses from about $5 \times 10^5$ to about $10^9$ pfu are preferred for MVA-based composition with a specific preference for doses of about $10^7$, about $5 \times 10^7$, about $10^8$ or about $5 \times 10^8$ pfu. Concerning Ad-based compositions, preferred doses contain from about $10^6$ to about $10^{12}$ vp, with a specific preference for doses of about $10^9$, about $5 \times 10^9$, about $10^{10}$, about $5 \times 10^{10}$ vp or about $10^{11}$ vp. A composition based on vector plasmids may be administered in doses of between 10 µg and 20 mg, advantageously between 100 µg and 2 mg. A protein composition may be administered in one or more doses of between 10 ng and 20 mg, with a special preference for a dosage from about 0.1 µg to about 2 mg of the therapeutic protein per kg body weight. The administration may take place in a single dose or a dose repeated one or several times after a certain time interval. When using two or more vectors (e.g. a polymerase-encoding vector and a core-env-encoding vector such as AdTG17909 and AdTG17910 illustrated in the appended examples), various modalities can be implemented. For example, the different vectors can be administered together (e.g. in the form of a vector mixture) or separately either at substantially the same time or with an appropriate period of time between each vector administration. Moreover, the different vectors can be adminsitered via the same route of administration or via different routes and at the same location of the body or at different locations.

The composition of the invention may be employed in methods for treating a variety of diseases and pathologic conditions, especially those caused by or associated with an HBV infection. As used herein, the term "treatment" or "treating" encompasses prophylaxis and/or therapy. It is especially useful for treating HBV chronic infection and/or liver lesions in HBV-infected patients including cirrhosis and liver cancer. Preferably, upon introduction into a host organism according to the modalities described herein, the composition of the invention provides a therapeutic benefit to the treated host as compared to before treatment. The therapeutic benefit can be evidenced by a number of ways, for instance a decrease of HBV viral load detected in blood, plasma, sera or liver of an infected subject, and/or by the detection of an anti-HBV immune response (e.g. production of anti-HBV antibodies and/or T cell-mediated immunity) or by the delay of the symptoms associated with an HBV infection (e.g. delay in the development of liver cirrhosis or cancer), or by a decrease of liver inflammation/steatosis/fibrosis conditions typically associated with HBV infection or by an improved response of the individual to conventional therapies.

Accordingly, the present invention also encompasses the use of at least one of the HBV moieties, nucleic acid molecules, vectors, infectious viral particles, host cells or compositions of the invention for the preparation of a drug intended for treating or preventing HBV infections, HBV-associated diseases and pathologic conditions, according to the modalities described herein.

The present invention also provides a method for the treatment or prevention of HBV infections, in particular chronic HBV infection, HBV-associated diseases and pathologic conditions, comprising administering to a human or animal organism in need thereof a therapeutically effective amount of at least one of the HBV moieties, nucleic acid molecules, vectors, infectious viral particles, host cells or compositions of the invention.

The method or use of the invention comprises one or more administrations (1, 2, 3, 4, 5, 6, 7, 8, 9, 10, etc) of a therapeutically effective amount of said active agent(s), said administrations being separated from each other by an appropriate period of time and being carried out by the same route of administration or by different routes of administrations (e.g. intramuscular and subcutaneous routes), at the same site or at different sites. Three administrations separated from each other by 3 to 10 days (e.g. 3 weekly administrations) are particularly suitable for MVA-based compositions and vector(s). This first series of administration can be followed by one or more subsequent administration(s) using the same active agent(s) which can take place one or several months so as to recall the anti-HBV immune response primed by the 3 sequential administrations. With respect to Ad-based compositions and vector(s), a preferred method or use includes one administration, eventually followed by one or two subsequent administration(s) one and 6 months later.

If desired, the method or use of the invention can be carried out in combination with one or more conventional therapeutic modalities (e.g. radiation, chemotherapy and/or surgery). The use of multiple therapeutic approaches provides the patient with a broader based intervention. In one embodiment, the method of the invention can be preceded or followed by a surgical intervention. In another embodiment, it can be preceded or followed by radiotherapy (e.g. gamma radiation). Those skilled in the art can readily formulate appropriate radiation therapy protocols and parameters which can be used (see for example Perez and Brady, 1992, Principles and Practice of Radiation Oncology, 2nd Ed. JB Lippincott Co; using appropriate adaptations and modifications as will be readily apparent to those skilled in the field).

In still another embodiment, the method or use of the invention is associated to chemotherapy with one or more HBV drugs which are conventionally used for treating or preventing HBV infections, HBV-associated diseases and pathologic conditions. Their administration may precede, be concomitant, or subsequent to the administration of the active agent in use in the invention. Representative examples of HBV drugs include without limitation polymerase inhibitors, RNase H inhibitors, nucleoside analogs, nucleotide analogs, TLR agonists, N-glycosylation inhibitors, siRNA, antisense oligonucleotides, anti-HBV antibodies, immune modulators, therapeutic vaccines and antitumor agents usually used in the treatment of HBV-associated liver cancers (e.g. adriamycin, adriamicin with lipiodol or sorasenib). Examples of suitable therapeutic vaccines include without limitation recombinant antigens, VLPs, vectors or synthetic peptides based on or encoding HBV proteins (Core, preS 1, PreS2, S and/or polymerase) which are particularly suited to trigger an anti-HBV humoral response. Such HBV drugs can be provided in a single dose or, alternatively, in multiple doses according to standard protocols, dosages and regimens over several hours, days and/or weeks. A particularly suitable method or use according to the invention is used in combination with standard of care which can be before, in parallel or subsequently to the method or use of the invention. Although such standard of care may vary from patient to patient, it generally comprises treatment with cytokines (e.g. IFNa, pegylated IFNa2) and/or with, nucleotide or nucleoside analogs such as lamivudine, entecavir, telbivudine, adefovir, dipivoxil or tenofovir.

In another embodiment, the method or use of the invention is carried out according to prime boost therapeutic modality which comprises sequential administrations of one or more priming composition(s) and one or more boosting composition(s). Typically, the priming and the boosting compositions use different vehicles which comprise or encode at least an antigenic domain in common. Moreover, the priming and boosting compositions can be administered at the same site or at alternative sites by the same route or by different routes of administration. For example, compositions based on polypeptide can be administered by a mucosal route whereas compositions based on vectors are preferably injected, e.g. subcutaneous injection for a MVA vector, intramuscular injection for a DNA plasmid and subcutaneous or intramuscular injection for an adenoviral vector.

The present invention also provides a method of inducing or stimulating an immune response against HBV in a host organism comprising administering to said organism at least one of the HBV moieties, nucleic acid molecules, vectors, infectious viral particles, host cells or compositions of the invention so as to induce or stimulate said immune response. The immune response can be a specific and/or a nonspecific, humoral and/or cellular and, in this context, it can be CD4+ or CD8+-mediated or both. The immune response is preferably a T cell response directed to an HBV antigen.

The ability of the method of the invention to induce or stimulate an anti-HBV immune response upon administration in an animal or human organism can be evaluated either in vitro or in vivo using a variety of assays which are standard in the art. For a general description of techniques available to evaluate the onset and activation of an immune response, see for example Coligan et al. (1992 and 1994, Current Protocols in Immunology; ed J Wiley & Sons Inc, National Institute of Health). Measurement of cellular immunity can be performed by measurement of cytokine profiles secreted by activated effector cells including those derived from CD4+ and CD8+ T-cells (e.g. quantification of IL-10 or IFNg-producing cells by ELIspot), by determination of the activation status of immune effector cells (e.g. T cell proliferation assays by a classical [$^3$H] thymidine uptake), by assaying for antigen-specific T lymphocytes in a sensitized subject (e.g. peptide-specific lysis in a cytotoxicity assay). The ability to stimulate a humoral response may be determined by antibody binding and/or competition in binding (see for example Harlow, 1989, Antibodies, Cold Spring Harbor Press). The method of the invention can also be further validated in animal models challenged with an appropriate infectious or tumor-inducing agent (e.g. a vaccinia virus or a *Listeria Monocytogenes* bacteria expressing HBV gene products) to determine neutralization of the infectious or tumor-inducing agent and eventually partial resistance to the associated symptoms, reflecting an induction or an enhancement of an anti-HBV immune response. Testing and validation of the compositions of the invention are also illustrated in the appended Example section.

In another aspect, the invention provides a kit of parts for use in the treatment or prevention of HBV infections, including chronic HBV infection, HBV-associated diseases and pathologic conditions according to the modalities described herein, and more particularly for inducing or generating an immune response in a subject infected with HBV, wherein said kit comprises a plurality of active agents selected from the group consisting of the HBV moieties, nucleic acid molecules, vectors, infectious viral particles, host cells and compositions described herein. Desirably, said plurality of active agents is provided in the form of separate polypeptides or separate vectors and administration of each of the active agents can take place simultaneously (at the same time) or separately (one following the other(s) after a certain time interval), by the same route or different routes of administration and at the same site (or close vicinity) or different sites and using the same dose or different doses.

Of particular interest in the present invention is a kit of parts which comprises a first vector comprising a nucleic acid molecule encoding the polymerase moiety as defined herein and a second vector comprising a nucleic acid molecule encoding the core moiety and/or the env moiety as defined herein.

According to a preferred embodiment, said first vector is a MVA vector comprising a nucleic acid molecule placed under the control of a vaccinia promoter such as the 7.5K promoter and encoding a polymerase moiety comprising an amino acid sequence as shown in SEQ ID NO: 7, 8 or 9 or in SEQ ID NO:7 with the substitution of the Asp residue in position 494 to an His residue and the substitution of the Glu residue in position 672 to an His residue; and said second vector is a MVA vector comprising a nucleic acid molecule placed under the control of a vaccinia promoter such as the pH5r promoter and encoding a core moiety and an env moiety comprising an amino acid sequence as shown in SEQ ID NO: 18 or 19. According to another preferred embodiment, said first vector is an adenovirus vector comprising a nucleic acid molecule placed under the control of a suitable promoter such as the CMV promoter and encoding a polymerase moiety comprising an amino acid sequence as shown in SEQ ID NO: 7 or SEQ ID NO: 8 or SEQ ID NO: 7 with the substitution of the Asp residue in position 494 to an His residue and the substitution of the Glu residue in position 672 to an His residue; and said second vector is an adenovirus vector comprising a nucleic acid molecule placed under the control of a suitable promoter such as the CMV promoter and encoding a core moiety and an env moiety comprising an amino acid sequence as shown in SEQ ID NO: 18, 19 or 20 or the portion of SEQ ID NO: 20 starting at residue 1 and ending at residue 251 (core-env1-env2) or the portion of SEQ ID NO: 20 starting at residue 1 and ending at residue 221 (core-env1).

The kit of parts of the present invention may further comprise a third vector expressing an immunomodulator as defined above. For illustrative purposes, preferred doses of each active ingredient comprised in the kit of parts is of the same order as that described above in connection with the composition of the invention, with a specific preference for a dose from $5 \times 10^5$ to $10^9$ pfu for each poxviral or MVA vector and from about $10^6$ to about $10^{12}$ vp for each adenoviral vector.

The invention also provides antibodies that selectively bind to the HBV moieties in use in the present invention or peptide fragments thereof. As used herein, an antibody selectively binds a target peptide when it binds the target peptide and does not significantly bind to unrelated proteins. In certain cases, it would be understood that antibody binding to the peptide is still selective despite some degree of cross-reactivity. It is nonetheless preferred that the antibody of the invention does not bind with high affinity or high selectivity to HBV native protein As used herein, an antibody is defined in terms consistent with that recognized within the art. The antibodies of the present invention include polyclonal antibodies and monoclonal antibodies, as well as fragments of such antibodies, including, but not limited to, Fab or F(ab').sub.2, and Fv fragments. Antibodies of the present invention can be produced using conventional techniques in the art, e.g. following administering to an animal an effective amount of any of the HBV moieties described herein and/or a peptide fragment thereof. Antibodies are preferably prepared from regions or discrete fragments of the HBV moieties comprising unique sequences, such as the ones directed to the modifications described herein introduced into the native HBV proteins.

Antibodies of the present invention have a variety of potential uses that are within the scope of the present invention. For example, such antibodies can be used (a) as reagents in assays to detect the first or second polypeptides of the present invention, (b) as reagents in assays to detect the presence of a HBV virus in a biological sample, and/or (c) as tools to recover the recombinantly-produced HBV moieties from a mixture of proteins and other contaminants (e.g. by permitting purification by affinity chromatography or immunoprecipitation from cultured host cells).

The present invention also relates to a method for the detection and/or quantification an HBV virus or an anti-HBV antibody in a biological sample (e.g. plasma, serum, tissue) taken from an individual susceptible to be infected by said HBV virus using at least one of the HBV moieties nucleic acid molecules, vectors, infectious viral particles, host cells, compositions or antibodies of the invention.

In one embodiment, the method is more particularly suited for the detection and/or quantification an HBV virus in a biological sample and comprises at least the steps of bringing said biological sample into contact with at least one of the antibodies of the invention under conditions allowing the formation of a complex between the virus and the antibody and detecting and/or quantifying the formation of said complex by any appropriate means.

In another embodiment, the method is more particularly suited for the detection and/or quantification an anti-HBV antibody in a biological sample and comprises at least the steps of bringing said biological sample into contact with at least one of the HBV moieties, nucleic acid molecules, vectors, infectious viral particles, host cells, compositions of the invention under conditions allowing the formation of a complex between the anti-HBV antibody and the HBV moiety, nucleic acid molecule, vector, infectious viral particle, host cell, composition of the invention and detecting and/or quantifying the formation of said complex by any appropriate means.

A person skilled in the art will easily determine the quantity of antibody, HBV moiety, nucleic acid molecule, vector, infectious viral particle, host cell, composition to be used in the methods of the invention. The means of detection and/or quantification of the virus are routine and well known to a person skilled in the art. By way of illustration, one may mention blots, ELISA, so-called sandwich techniques, competition techniques, and PCR techniques, in particular so called "real-time" techniques. The use of an antibody, HBV moiety, nucleic acid molecule, vector, infectious viral particle, host cell, or composition of the present invention as reagent can be facilitated by coupling (i.e., physically linking) to a detectable substance. Examples of detectable substances include various enzymes (e.g. horseradish peroxidase, alkaline phosphatase, beta-galactosidase or acetylcholinesterase), prosthetic groups (e.g. streptavidin/biotin, or avidin/biotin), fluorescent materials (e.g. umbelliferone, fluorescein, or fluorescein derivatives), luminescent materials, bioluminescent materials (e.g. luciferase, luciferin, or aequorin), and radioactive materials (e.g. $^{125}$I, $^{131}$I, $^{35}$S or $^3$H). Finally, the invention relates to the use of at least one of the HBV moieties, nucleic acid molecules, vectors, infectious viral particles, host cells, compositions, or antibodies of the invention for the in vitro diagnosis of an HBV infection in a biological sample.

The invention also relates to the immunogenic composition, the nucleic acid molecule, the vector, the infectious viral particle, the host cell or the composition as described herein for use in a subject infected with or suspected to be infected with an HBV for the treatment of an HBV infection, and especially a chronic HBV infection, wherein said subject is infected or suspected to be infected with an HBV from a genotype that is different from the HBV genotype administered to said subject.

The invention also concerns a method of treating an HBV infection or a disease or condition associated with an HBV infection, and especially a chronic HBV infection in a subject in need thereof comprising the step of a) identifying a subject infected or suspected to be infected with an HBV; b) administering to the subject a sufficient amount of the immunogenic composition, the nucleic acid molecule, the vector, the infectious viral particle, the host cell or the composition as described herein, wherein said subject is infected or suspected to be infected with an HBV from a genotype that is different from the HBV genotype administered to said subject Advantageously, the subject is infected or suspected to be infected with an HBV from a genotype B or C and the HBV genotype administered to said subject is of genotype D. Preferably, each moiety comprised or encoded in/by the therapeutic agent (immunogenic composition, vector, infectious particle, etc) is from genotype D and preferably from HBV isolate Y07587. More preferably, the amino acid sequences of the polymerase moiety, the core moiety and/or the env moiety comprised in the immunogenic composition are as defined herein. Even more preferably, the method or use according to the invention is in combination with standard of care as described herein.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practiced in a different way from what is specifically described herein.

All of the above cited disclosures of patents, publications and database entries are specifically incorporated herein by reference in their entirety to the same extent as if each such individual patent, publication or entry were specifically and individually indicated to be incorporated by reference.

LEGENDS OF FIGURES

FIGS. 1A and 1B illustrates HBV polypeptide expression from adenovirus and MVA infected cells. A549 cells or chicken embryo fibroblasts were infected at MOI 10 or 50 for adenovirus or MOI 0.2 or 1 for MVA and cells were lysed 48h after infection. Western blot were then performed with cell lysates obtained from cells infected with the various Ad (FIG. 1A) and MVA (FIG. 1B) constructs to detect specific HBV proteins. Core-containing polypeptides were detected using an anti-Core antibody (C1-5 or 13A9, dilution 1/200) and polymerase-containing polypeptides with an anti-Pol antibody (8D5, dilution 1/200) as primary antibodies and the secondary antibody was coupled to HRP. Expected sizes for the proteins expressed by Ad TG17909 and Ad TG17910 are respectively 31.6 kDa and 88.5 kDa. Expected sizes for proteins expressed by MVA TG17971, MVA TG17972, MVA TG17993 and MVA TG17994 are respectively 20.2 kDa, 15.8 kDa, 20 kDa and 23.5 kDa. Expected sizes for proteins expressed by MVA TG17842 and MVA TG17843 are 88.5 kDa and 98.2 kDa respectively.

FIGS. 2A-2C illustrates the immunogenicity of HBV polypeptides encoded by adenovirus in Elispots IFNγ assays. Five individual mice (HLA-A2 transgenic mice) were immunised once with either Ad TG17909 alone (black bars), Ad TG17910 alone (white bars) or in combination (Ad TG17909+Ad TG17910) (grey bars). FIG. 2A illustrates specific T cell responses targeting Polymerase protein using the HLA-A2 restricted peptide SLY (SEQ ID NO: 55) or an irrelevant one (not shown). FIG. 2B illustrates specific T cell responses targeting Core protein using the HLA-A2 restricted peptides FLP (SEQ ID NO: 56) or ILC (SEQ ID NO: 57). FIG. 2C illustrates specific T cell responses targeting Env domains using the HLA-A2 restricted peptides VLQ (SEQ ID NO: 58), FLG (SEQ ID NO: 59) or GLS (SEQ ID NO: 60). Each bar represents an individual vaccinated mouse and the hatched bars represent the median of each group. Results are shown as the mean value of the number of spots observed for $10^6$ spleen cells, obtained from triplicate wells. A response was considered positive if the number of spots was higher than 50 spots per $10^6$ cells (this cut-off is represented by a thick black line).

Figure 3:
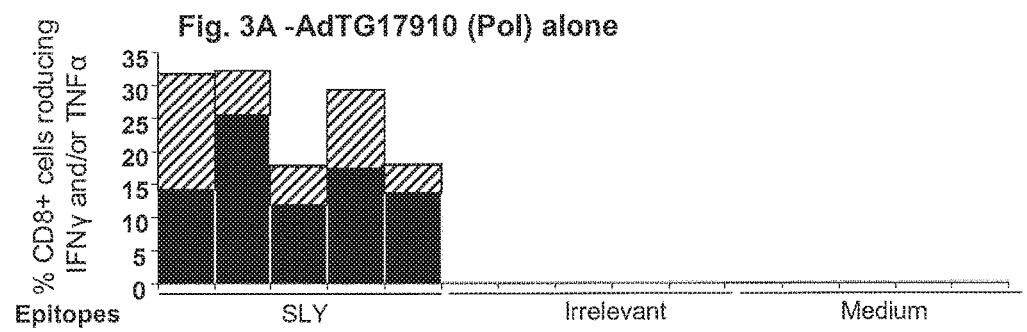
Figure 3:
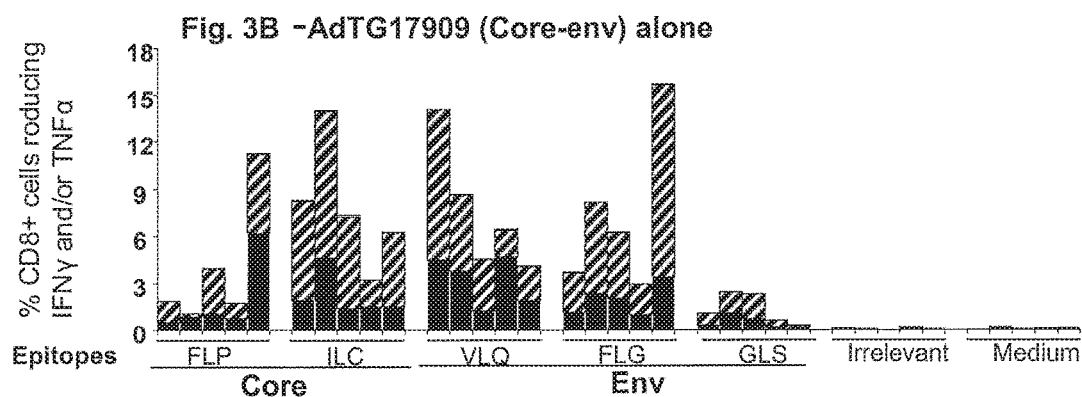
Figure 3:
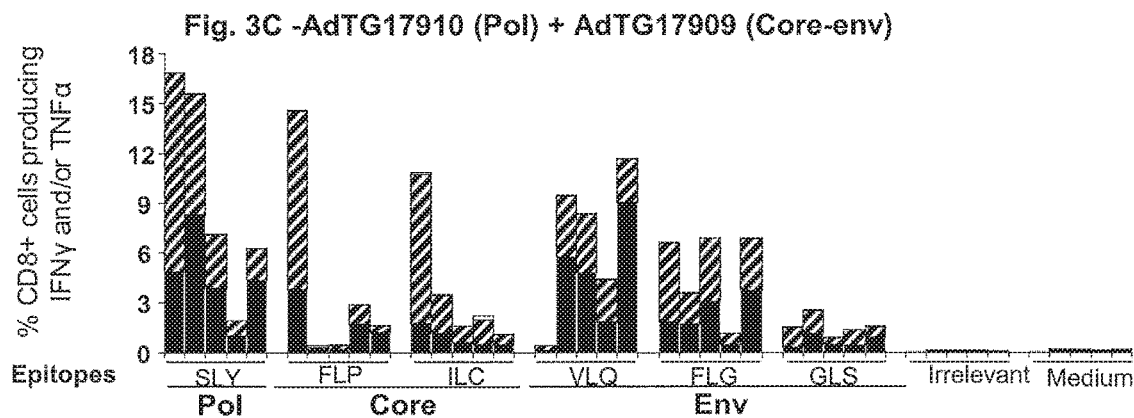

FIGS. 3A-3C illustrates the immunogenicity of HBV polypeptides encoded by adenovirus vector in intracellular cytokine staining assays. Five individual mice (HLA-A2 transgenic mice) were immunised once with either AdTG17909 (FIG. 3B), AdTG17910 (FIG. 3A) or a combination of AdTG17909 and AdTG17910 (FIG. 3C). Splenocytes were cultured for 5h with Golgi-Plug and in presence of each HLA-A2 restricted peptide (SLY for Pol, FLP, ILC for Core, VLQ, FLG and GLS for Env) or an irrelevant one. The percentage of CD8+ cells producing cytokines (IFNg and/or TNFa) specific of each HLA-A2 restricted epitopes, was assessed by ICS assays. Each bar represents an individual vaccinated mouse, with IFNg producing cells represented by a black bar, TNFa producing cells by a white bar and IFNg+TNFa producing cells by a hatched bar and all these cell populations are piled for each mouse.

FIGS. 4A-4C illustrates the ability of HBV polypeptides encoded by adenovirus vector to induce CD8 and CD4 T cell responses, detected by intracellular cytokine staining assays. Five individual mice (HLA-A2 transgenic mice) were immunised once with a mixture of AdTG17909 and AdTG17910. Splenocytes were cultured for 5h with Golgi-Plug and in presence of each HLA-A2 restricted peptide (SLY for Pol, FLP, ILC for Core, VLQ, FLG and GLS for Env) or pools of overlapping peptides (15aa overlapping by 1 lamino acids, 2 pools of peptides for Core and 2 pools of peptides for Env) covering the whole antigenic domains or an irrelevant peptide. Induced specific CD8 T cells producing IFNgamma and/or TNFalpha (FIG. 4A) and induced specific CD4 T cells producing IFNgamma and/or TNFalpha (FIG. 4B) or producing IFNgamma and/or IL2 (FIG. 4C) were monitored by ICS assays. Each bar represents an individual vaccinated mouse, with IFNg producing cells represented by a grey bar, TNFa or IL2 producing cells by a white bar and IFNg+TNFa or IFNg+IL2 producing cells by a hatched bar and all these cell populations are piled for each mouse. The median of each group is also showed.

FIGS. 5A and 5B illustrates the ability of adenovirus vector encoding HBV polypeptides to induce in vivo functional cytolysis against target cells loaded with HBV HLA-A2 restricted epitopes. Three individual mice (HLA-A2 transgenic mice) were immunised once with a combination of AdTG17909 and AdTG17910 (M1 to M3) and one mouse was immunized once with an empty adenovirus vector as negative control (M0). CFSE stained splenocytes from syngenic mice, loaded with HBV HLA-A2 epitopes or not (negative control) were injected intraveinously to vaccinated mice. The in vivo lysis of stained cells was assessed for each mouse 24h later by flow cytometry and calculated as indicated in Material and methods. The mean of specific lysis observed for each peptide for the 3 mice vaccinated with AdHBV was calculated and showed (Mean M1-M3).

FIGS. 6A and 6B illustrates the immunogenicity of HBV polypeptides encoded by MVA vector as determined by Elispots IFNgamma assays. Individual mice (HLA-A2 transgenic mice) were immunised three times at one week interval with either MVATG17842 or MVATG17843 (FIG. 6A) or MVATG17971 (FIG. 6B) or MVA TG17972 or the negative control MVA TGN33.1 (data not shown). FIG. 6A illustrates specific T cell responses targeting Polymerase protein following immunization with MVA TG17842 (dark grey bars) or MVATG17843 (light grey bars) using the HLA-A2 restricted peptide SLY (SEQ ID NO: 55), pool 8 of peptides covering the C-terminal part of the polymerase protein (25 peptides of 15 amino acids overlapping by 11 amino acids/pool), an irrelevant peptide or medium (negative controls). FIG. 6B illustrates specific T cell responses targeting Core protein following immunization with MVATG17971 using the HLA-A2 restricted peptides FLP (SEQ ID NO: 56), ILC (SEQ ID NO: 57), peptides pools "core 1 and core 2" (21 to 22 peptides of 15 amino acids overlapping by 11 amino acids/pool), an irrelevant peptide or medium (negative controls). Each bar represents an individual vaccinated mouse and the hatched bars represent the mean of each group. Results are shown as the mean value of the number of spots observed for $10^6$ spleen cells, obtained from triplicate wells. A response was considered positive if the number of spots was higher than 50 spots per $10^6$ cells (this cut-off is represented by a dotted black line).

FIGS. 7A-7C illustrates the immunogenicity of HBV polypeptides encoded by MVA vectors co-injected in mouse, as determined by Elispots IFNgamma assays. Individual mice (HLA-A2 transgenic mice) were immunised three times at one week interval with a mix of MVATG17843 and either MVATG17972 (FIG. 7A) or MVATG17993 (FIG. 7B) or MVATG17994 (FIG. 7C) or with MVA TG N33.1 alone as negative control (data not shown). Specific T cell responses targeting Polymerase protein were determined using the HLA-A2 restricted peptide SLY (SEQ ID NO: 55) and specific T cell responses targeting Env domains using the HLA-A2 restricted peptide GLS (SEQ ID NO: 60) or a pool of peptides covering the Env2 domain (pool of 15 amino acid-long peptides overlapping by 11 amino acids). An irrelevant peptide and medium were used as negative controls. Each bar represents an individual vaccinated mouse and the hatched bars represent the mean of each group. Results are shown as the mean value of the number of spots observed for $10^6$ spleen cells, obtained from triplicate wells. A response was considered positive if the number of spots was higher than 92 spots per $10^6$ cells (this cut-off is represented by a dotted black line).

FIGS. 8A and 8B illustrates the cross-reactive potential of T-cells induced by HBV polypeptides encoded by adenoviruses and specific of HBV Core antigen in HLA-A2 transgenic mouse model.

HLA-A2 mice were immunized by subcutaneous route with $10^8$ iu of AdTG17909 and $10^8$ iu of AdTG17910. Splenocytes were taken 2 weeks after immunisation and ELISpot IFNg (FIG. 8A) and ICS (FIG. 8B) were performed following stimulation with peptides which amino acid sequence is homologous to the HBV sequence encoded by the adenovirus (FLP and ILC) and the major and minor variants identified in Table 1. Open symbols and thin lines represent the values obtained for individual animals whereas filled symbols and bold lines correspond to group means. Horizontal lines represent the cut-off of positivity. Main variants of the different genotypes are framed by a pointed line. Responder frequency (percentage of animals above the cut-off) and normalised mean (group mean for a given epitope variant divided by the group mean for the homologous peptide) are indicated below the graphs. ILC variants are ranked in decreasing order of their Elispot normalised mean. Statistical difference in the level of observed T cell responses between the homologous peptide and its respective variants is indicated by a star. As a log-scale was used to represent the results, Elispot values equal to zero were represented as 1 on the graph and ICS values under 0.03% were represented as equal to 0.03% (but real values were used to calculate means).

FIGS. 9A and 9B illustrates the cross-reactive potential of T-cells specific of HBV Env domains in HLA-A2 transgenic mouse model.

HLA-A2 mice were immunized by subcutaneous route with $10^8$ iu of AdTG17909 and $10^8$ iu of AdTG17910. Splenocytes were taken 2 weeks after immunisation and ELISpot IFNg (FIG. 9A) and ICS (FIG. 9B) were performed following stimulation with peptides which amino acid sequence is homologous to the HBV sequence encoded by the adenovirus (VLQ, FLG and GLS) and the major and minor variants identified in Table 1. Open symbols and thin lines represent the values obtained for individual animals whereas filled symbols and bold lines correspond to group means. Horizontal lines represent the cut-off of positivity. Main variants of the different genotypes are framed by a pointed line. Responder frequency (percentage of animals above the cut-off) and normalised mean (group mean for a given epitope variant divided by the group mean for the homologous peptide) are indicated below the graphs. Epitope variants are ranked in decreasing order of their normalised mean. Statistical difference in the level of observed T cell responses between the homologous peptide and its respective variants is indicated by a star. As a log-scale was used to represent the results, Elispot values equal to zero were represented as 1 on the graph and ICS values under 0.03% were represented as equal to 0.03% (but real values were used to calculate means).

EXAMPLES

1. Material and Methods

The constructions described below are carried out according to the general genetic engineered and molecular cloning techniques detailed in Maniatis et al. (1989, Laboratory Manual, Cold Spring Harbor Laboratory Press, Cold Spring Harbor N.Y.) or according to the manufacturer's recommendations when a commercial kit is used. PCR amplification techniques are known to the person skilled in the art (see for example PCR protocols—A guide to methods and applications, 1990, published by Innis, Gelfand, Sninsky andWhite, Academic Press). The recombinant plasmids carrying the ampicillin resistance gene are replicated in the *E. coli* C600 (Stratagene) on agar or liquid medium supplemented with 100 µg/ml of antibiotic. The constructions of the recombinant vaccinia viruses are performed according to the conventional technology in the field in the documents above cited and in Mackett et al. (1982, Proc. Natl. Acad. Sci. USA 79, 7415-7419) and Mackett et al. (1984, J. Virol. 49, 857-864). The selection gene gpt (xanthine guanine phosphoribosyltransferase) of *E. coli* (Falkner and Moss, 1988, J. Virol. 62, 1849-1854) is used to facilitate the selection of the recombinant vaccinia viruses.

1.1. Vectors Constructions and Production
1.1.1. Selected Antigens and HBV Sequence Strain The vectors exemplified hereinafter have been engineered to express the polymerase, core polypeptides and immunogenic domains of the envelope protein. They all originate from HBV strain Y07587 which sequence is described in international databases (Genbank Y07587) and in different publications. It is a genotype D virus of serotype ayw.

The Core polypeptide is either wild-type (aa 1-183) or a Core polypeptide deleted of amino acids 77 to 84 (i.e. Core containing amino acid 1 to 76 and 85 to 183 designated core*) or a C-terminally truncated polypeptide (1-148) or a C-terminally truncated core (1-148) further deleted of amino acids 77 to 84 (i.e. Core containing amino acid 1 to 76 and 85 to 148 designated core*t).

The polymerase polypeptide is either wild type or a N-terminally truncated polypeptide lacking the first 47 amino acids (48-832) or a N-truncated polymerase (48-832) further mutated at postititon 540 (D in H) and 718 (E in H) (positions 450 and 718 being given with respect to the wild-type polymerase) or the truncated (48-832) and mutated polymerase (D540H and E718H) which is fused to the peptide signal and transmembrane domain of the rabies virus glycoprotein (Pol*TMR).

The selected Env domains are: domain from amino acids 14 to 51 of the S protein (Env 1) and domain from amino acids 165 to 194 of the HBs protein (Env 2) and domain from amino acid 202 to 226 of the HBs protein (Env 4).

1.1.2. Construction and Production of a MVATG17842 Expressing a Truncated and Mutated HBV Polymerase (Pol*)

The nucleotide sequences encoding a modified HBV polymerase polypeptide were synthesized by Geneart company using synthetic oligonucleotides and PCR products. The modified HBV polymerase corresponds to the polymerase protein of HBV Y07587 (SEQ ID NO:1) mutated at position 540 (D in H) and 718 (E in H) in order to eliminate Rnase H and RTase activities exhibited by the native HBV polymerase (resulting in amino acid sequence shown in SEQ ID NO: 8 and nucleotide sequence shown in SEQ ID NO: 22). The reassembled Pol sequence was then cloned in a plasmid vector resulting in PGA15-pol (SEQ ID NO: 27). A truncated version deleted of the first 47 amino acids present at the N-terminus of the native HBV polymerase was amplified by PCR from pGA15-Pol plasmid using the following primers OTG19037 (GAGCGATATCCACCATGAATGTTAGTATTCCTTGGAC) (SEQ ID NO: 28) and OTG19038 (GATCGCTAGCTCACGGTGGTCTCCATGCGAC) (SEQ ID NO: 29). The resulting fragment was inserted into the NheI and EcoRV restriction sites of a MVA transfer plasmid downstream the p7.5K promoter (Cochran et al, 1985, J. Virol. 54:30), resulting in pTG17842. The mutated and truncated polymerase is designated hereinafter pol*.

The MVA transfer plasmid is designed to permit insertion of the nucleotide sequence to be transferred by homologous recombination in deletion III of the MVA genome. It originates from plasmid pTG1E (described in Braun et al., 2000, Gene Ther. 7:1447) into which were cloned the flanking sequences (BRG3 and BRD3) surrounding the MVA deletion III (Sutter and Moss, 1992, Proc. Natl. Acad. Sci. USA 89:10847). The transfer plasmid also contains a fusion between the *Aequorea victoria* enhanced Green Fluorescent protein (eGFP gene, isolated from pEGP-C1, Clontech) and the *Escherichia coli* xanthine-guanine phosphoribosyltransferase gene (gpt gene) under the control of the early late vaccinia virus synthetic promoter p 11K7.5 (kindly provided by R. Wittek, University of Lausanne). Synthesis of xanthine-guanine phosphoribosyltransferase enables GPT+ recombinant MVA to form plaques in a selective medium containing mycophenolic acid, xanthine, and hypoxanthine (Falkner et al, 1988, J. Virol. 62, 1849-54) and eGFP enables the visualisation of recombinant MVA plaques. The selection marker eGFP-GPT is placed between two homologous sequences in the same orientation. When the clonal selection is achieved, the selection marker is easily eliminated by several passages without selection allowing the growth of eGFP-GPT− recombinant MVA.

Generation of MVATG17842 virus was performed by homologous recombination in primary chicken embryos fibroblasts (CEF) infected with MVA and transfected with pTG17842 (according to the standard calcium phosphate DNA precipitation). Viral selection was performed by three round of plaque purification in the presence of a selective medium containing mycophenolic acid, xanthine and hypoxanthine. As mentioned above, the selection marker was then eliminated by passage in a non-selective medium. Absence of contamination by parental MVA was verified by PCR.

Analysis of expression of HBV polymerase was performed by Western-blot. A549 cells (ATCC CCL-185) were infected at MOI of 1 with MVATG17842 (Pol*) in presence or in absence of proteasome inhibitor MG-132 (10 µM) added to growth medium. After 24 hours, cells were harvested. Western-blot analysis was performed using commercial monoclonal anti-Pol antibody Hep B Pol (8D5, Santa Cruz, #sc-81591).

1.1.3. Construction and Production of MVATG17843 Expressing a Truncated and Mutated HBV Polymerase Fused to the Membrane-Anchoring Domain of Rabies Envelop Glycoprotein (Pol*TMR)

The HBV Pol* sequence was then modified by fusion at its N-terminus to a peptide signal (SS) and at its C-terminus to a membrane-anchoring sequences (TMR) derived from the glycoprotein of the rabies virus (ERA isolate; described in Genbank No M38452). The SS and TMR sequences were amplified from plasmid pTG8042 (described in WO99/03885) by PCR using respectively primer pairs OTG19045 (SEQ ID NO: 30) (GAGTGATATCCACCATGGTTCCTCAGGCTCTCCTG)/OTG19047 (SEQ ID NO: 31) (GTCCAAGGAATACTAACATTAATAGGGAATTTCCCAAAACACAATG) and OTG19049 (SEQ ID NO: 32) (GTCGCATGGAGACCACCGTATGTATTACTGAGTGCAGGG/OTG19050 (SEQ ID NO: 33) (GAGTGCTAGCTCACAGTCTGGTCTCACCC). Pol* sequence was amplified from plasmid pGA15-Pol by PCR using primer pair OTG19046 (SEQ ID NO: 34) (GTTTTGGGAAATTCCCTATTAATGTTAGTATTCCTTGGACTC)/OTG19048 (SEQ ID NO: 35) (CTGCACTCAGTAATACATACGGTGGTCTCCATGCGACGTGC). Then, SS-Pol*-TMR sequence was reassembled by triple PCR using the following primers OTG19045 (SEQ ID NO: 30) and OTG19050 (SEQ ID NO: 33). The resulting fragment was inserted into the NheI and EcoRV restriction sites of a vaccinia transfer plasmid downstream the p7.5K promoter (Cochran et al, 1985, J. Virol. 54:30), resulting in pTG17843.

Generation of MVATG17843 virus was performed in CEF by homologous recombination as described above.

Analysis of Pol*-TMR expression was performed by Western-blot. A549 cells were infected at MOI 1 with MVATG17843 in presence or in absence of proteasome inhibitor MG-132 (10 µM) added to growth medium. After 24 hours, cells were harvested. Western-blot analysis was performed using commercial monoclonal anti-Pol antibody Hep B Pol (8D5, Santa Cruz, #sc-81591).

1.1.4 Construction and Production of MVATG17971 Expressing a Deleted Core Polypeptide (Core*)

Core* corresponds to the Core sequence of HBV Y07587 (SEQ ID NO: 2) deleted of amino acids 77 to 84.

The Core* encoding sequences were reconstituted by double PCR from pGA4-Core plasmid. This plasmid was made by Geneart company. It contains a full length coding sequence of modified HBV Core gene which was assembled from synthetic oligonucleotides and/or PCR products. The last two codons CAA TGT of the coding sequence were modified in CAG TGC to avoid sequence homology with Pol (SEQ ID NO: 36).

Core sequence from positions 1 to 76 was amplified by PCR using the following primers OTG19290 (SEQ ID NO: 37) (GACTGTTAACCACCATGGACATTGATCCTTATAAAGAATTTG) and OTG19292 (SEQ ID NO: 38) (GTTGACATAACTGACTA-CCAAATTACCACCCACCCAGGTAG). Core sequence from positions 85 to 183 was amplified by PCR with the following primers OTG19291 (SEQ ID NO: 39) (GTGGGTGGTAATTTGGTAGTCAGTTATGTCAACACTAATATG) and OTG19080 (SEQ ID NO: 61) (GACTCTCGAGTTAGCACTGAGATTCCCGAGATTG). A double PCR was performed using OTG19290 (SEQ ID NO: 37) and OTG19080 (SEQ ID NO: 61) and both latter generated amplicons. The resulting fragment was inserted into the XhoI and HpaI restriction sites of a vaccinia transfer plasmid downstream the pH5R promoter (Rosel et al, 1986, J Virol. 60:436), resulting in pTG17971.

Generation of MVATG17971 virus was performed in CEF by homologous recombination as described above.

Analysis of Core* expression was performed by Western-blot. Chicken embryo fibroblasts were infected at MOI 0.2 with MVATG17971. After 24 hours, cells were harvested. Western-blot analysis was performed using a commercial monoclonal anti-core antibody Hep B cAg (13A9) (Santa Cruz, #sc-23946).

1.1.5 Construction and Production of MVATG17972 Expressing a Deleted and Truncated Core Polypeptide (Core*t)

Core*t corresponds to the Core sequence of HBV Y07587 (SEQ ID NO: 2) truncated after amino acid 148 and deleted of amino acids 77 to 84.

The Core*t-encoding sequences were reconstituted by double PCR from pGA4-Core plasmid which contains the sequence encoding the full length HBV Core gene which was assembled from synthetic oligonucleotides and PCR products except that the last two codons CAA TGT of the coding sequence were modified in CAG TGC to avoid sequence homology with Pol (SEQ ID NO: 36).

Core sequence from positions 1 to 76 was amplified by PCR using the following primers OTG19290 (SEQ ID NO: 37) (GACTGTTAACCACCATGGACATTGATCCTTA-TAAAGAATTTG) and OTG19292 (SEQ ID NO: 38) (GT-TGACATAACTGACTA-CCAAATTACCACCCACCCA-GGTAG). Core sequence from positions 85 to 148 was amplified by PCR from pGA4-core with the following primers OTG19291 (SEQ ID NO: 39) (GTGGGTGG-TAATTTGGTAGTCAGTTATGTCAACACTAATATG) and OTG19299 (SEQ ID NO: 40) (GACTCTCGAGT-TAAACAGTAGTCTCCGGAAGTG). The double PCR was performed using OTG19290 (SEQ ID NO: 37) and OTG19299 (SEQ ID NO: 40). The resulting fragment was inserted into the XhoI and HpaI restriction sites of a vaccinia transfer plasmid downstream the pH5R promoter (Rosel et al, 1986, J Virol. 60:436), resulting in pTG17972.

Generation of MVATG17972 virus was performed in CEF by homologous recombination as described above.

Analysis of Core*t expression was performed by Western-blot. Chicken embryo fibroblasts were infected at MOI 0.2 with MVATG17972. After 24 hours, cells were harvested. Western-blot analysis was performed using a commercial monoclonal anti-core antibody Hep B cAg (13A9) (Santa Cruz, #sc-23946).

1.1.6 Construction and Production of MVATG17993 Expressing a Deleted and Truncated Core Polypeptide Fused to the Env1 Immunogenic Domain (Core*t-Env1)

The Core-t* moiety was fused to Env1 domain extending from amino acids 14 to 51 of the HBs protein.

The Core*t-Env1 sequence was reconstituted by double PCR. Core*t sequence was amplified by PCR from pTG17972 using the following primers OTG19317 (SEQ ID NO: 41) (GACG GGATCCACCATGGACATTGATCCTTATAAAGAATTTG) and OTG19319 (SEQ ID NO: 42) (GCCTGCTTGCAGGA-CAACAGTAGTCTCCGGAAGTGTTG). Env1 sequence was amplified by PCR from plasmid pMK-C/E (SEQ ID NO: 43) using the following primers OTG19318 (SEQ ID NO: 44) (CCGGAGACTACTGTTGTCC-TGCAAGCAG-GCTTCTTC) and OTG19320 (SEQ ID NO: 45) (GAGT-CATTCTCGAC-TT GCGGCCGCTTACTGACCCAGGCAAACCGTGG). The double PCR was performed using OTG19317 (SEQ ID NO: 41) and OTG19320 (SEQ ID NO: 45). The resulting fragment was inserted into the BamHI and NotI restriction sites of a vaccinia transfer plasmid downstream the pH5R promoter (Rosel et al, 1986, J Virol. 60:436), resulting in pTG17993.

For illustrative purposes, the plasmid pMK-C/E was made by Geneart and contains a chimeric sequence consisting of an insertion of three HBV env domain sequences into core sequence (SEQ ID NO: 43). The native core and env nucleotide sequences were degenerated to avoid sequence homology with HBV Pol sequence and also sequence instability due to polyT or polyGC stretches. In addition, the core sequence was deleted of amino acids 77 to 84 and truncated at aa148. The selected Env domains are: domain from amino acids 14 to 51 of the S protein (Env 1) and domain from amino acids 165 to 194 of the S protein (Env 2) and domain from amino acid 202 to 226 of the S protein (Env 4). The three domains were inserted respectively at positions nt 127, at nt 222 and at nt 416 of core sequence. It has to be noted that insertion of this sequence in a MVA vector results in cytotoxicity in the expressing cells, emphasizing the fact that the design of the env-core fusion is not straightforward.

Generation of MVATG17993 virus was performed in CEF by homologous recombination as described above.

Analysis of Core*t-env1 expression was performed by Western-blot. Chicken embryo fibroblasts were infected at MOI 0.2 with MVATG17993. After 24 hours, cells were harvested. Western-blot analysis was performed using a commercial monoclonal anti-core antibody Hep B cAg (13A9)(Santa Cruz, #sc-23946).

1.1.7. Construction and Production of MVATG17994 Expressing a Deleted and Truncated Core Polypeptide Fused to Env1 and Env2 Immunogenic Domains (Core*t-Env1-Env2)

The Core*t polypeptide described in 1.1.5 was then fused to two immunogenic domains extending from amino acids 14 to 51 (Env 1) and from amino acid 165 to 194 (Env2) of the HBs protein The nucleotide sequences encoding the Core*t-Env1-Env2 were reassembled by triple PCR. Core*t sequence was amplified by PCR from pTG17972 using the following primers OTG19317 (SEQ ID NO: 41) and OTG19319 (SEQ ID NO: 42). Env1 was amplified from pMK-C/E plasmid using the following primers OTG19318 (SEQ ID NO: 44) and OTG19322 (SEQ ID NO: 46 (GCGTGCGCTTGC-CCACTGACCCAGGCAAACCGTGG). Env2 was amplified from pMK-C/E plasmid using the following primers OTG19321 (SEQ ID NO: 47 (CGGTTTGCCTGGGTCA-GTGGGCAAGCGCACGCTTTAGC) and OTG19323 (SEQ ID NO: 48) (GAGTCATTCTCGACTT GCGGCCGCTTACACGCTCAGCCACACGGTTGG). The triple PCR was performed using OTG19317 (SEQ ID NO: 41) and OTG19323 (SEQ ID NO: 48). The resulting fragment was inserted into the BamHI and NotI restriction sites of a vaccinia transfer plasmid downstream the pH5R promoter (Rosel et al, 1986, J Virol. 60:436), resulting in pTG17994.

Generation of MVATG17994 virus was performed in CEF by homologous recombination as described above.

Analysis of Core*t-env1-env2 expression was performed by Western-blot. Chicken embryo fibroblasts were infected at MOI 0.2 with MVATG17994. After 24 hours, cells were harvested. Western-blot analysis was performed using a commercial monoclonal anti-core antibody Hep B cAg (13A9, Santa Cruz, #sc-23946).

1.1.8. Construction and Production of an Adenoviral Vector AdTG17909 Expressing CORE-Env1-Env2-Env4:

A synthetic gene (831 nucleotides) encoding a CORE-Env1-Env2-Env4 fusion was reconstituted by double PCR. CORE was amplified by PCR from pGA4-Core (described in 1.1.4.) using the following primers OTG19152 (SEQ ID NO: 49) (GGGGGGCTAGCAAGCTTCCACCATGGA-CATTGATCCTTATAAAGAATTTG) and OTG19154 (SEQ ID NO: 50) (GAAAGAATCCAGCTTGCAGGACGCACT-GAGATTCCCGAGATTGAG). Env1-Env2-Env4 were amplified by PCR from pGA4-Env using the following primers OTG19153 (SEQ ID NO: 51) (CT-CAATCTCGGGAATCT-CAGTGCGTCCTGCAAGCTG-GATTCTTTC) and OTG19159 (SEQ ID NO: 52) (GAGT-CATTCTCGACTTGCGGCCGCTTAGATATAAACCC ACAAGC). The double PCR was performed using OTG19152 (SEQ ID NO: 49) and OTG19159 (SEQ ID NO: 52). The resulting fragment was inserted into the NheI and NotI restriction sites of an adenoviral shuttle plasmid containing a CMV-driven expression cassette surrounded by adenoviral sequences (adenoviral nucleotides 1-454 and nucleotides 3513-5781 respectively) to allow generation of the vector genome by homologous recombination (Chartier et al., 1996, J. Virol. 70:4805). The resulting adenoviral vector pTG17909 is E3 (nucleotides 28593-30464) and E1 (nucleotides 455-3512) deleted, with the E1 region replaced by the expression cassette containing, from 5' to 3', the CMV immediate-early enhancer/promoter, a chimeric human β-globin/IgG intron (as found in pCI vector available in Promega), the sequence encoding the CORE-Env1-Env2-Env4 and the SV40 late polyadenylation signal. The recombinant adenovirus was generated by transfecting the Pac linearized viral genomes into an E1 complementation cell line. Virus propagation, purification and titration were made as described previously [Erbs, 2000] (Erbs et al., 2000, Cancer Res. 60:3813) Expression of the fusion protein was evaluated by Western-blot. $10^6$ A549 cells (ATCC CCL-185) were infected at MOI of 10 or 50 for 48 hours with AdTG17909 or with an empty adenovirus as negative control. The cell pellets were collected and probed with an anti CORE mouse monoclonal antibody (C1-5, sc-23945, Santa Cruz).

1.1.9. Construction and Production of Adenoviral Vector AdTG17910 Expressing Pol*:

The gene encoding Pol*, a polymerase protein truncated of the 47 first amino acids except the Met initiator (48 to 832) and mutated at posititon 540 (D in H) and 718 (E in H) (with respect to the wild type polymerase) was inserted in an adenovirus vector. The Pol gene (2364 nucleotides) was amplified by PCR from pGA15-Pol (described in 1.1.2) using primers OTG19155 (SEQ ID NO: 53) (GGGGGGCTAGCAAGCTTCCACCATGAA-TGTTAGT-ATTCCTTGGACTCATAAG) and OTG19156 (SEQ ID NO: 54) (GAGTCATTCTCGACTTGCGGCCGCTCACG-GTGGTCTCCATGCGACGTGC). The resulting fragment was inserted into the NheI and NotI restriction sites of an adenoviral shuttle plasmid containing a CMV-driven expression cassette surrounded by adenoviral sequences (adenoviral nucleotides 1-454 and nucleotides 3513-5781 respectively) to allow generation of the vector genome by homologous recombination (Chartier et al., 1996, J. Virol. 70:4805). The resulting adenoviral vector pTG17910 is E3 (nucleotides 28593-30464) and E1 (nucleotides 455-3512) deleted, with the E1 region replaced by the expression cassette containing, from 5' to 3', the CMV immediate-early enhancer/promoter, a chimeric human β-globin/IgG intron (as found in pCI vector available in Promega), the sequence encoding the truncated and mutated Pol and the SV40 late polyadenylation signal. The recombinant adenovirus was generated by transfecting the PacI linearized viral genomes into an E1 complementation cell line. Virus propagation, purification and titration were made as described previously (Erbs et al., 2000, Cancer Res. 60:3813).

Expression of the fusion protein was evaluated in adenovirus infected cells by Western-blot. A549 cells ($10^6$ cells) (ATCC CCL-185) were infected at MOI of 10 or 50 for 48 hours with the adenovirus AdTG17910, as well as an empty adenovirus as negative control. The cell pellets were collected and probed with an anti Pol mouse monoclonal antibody (8D5, sc-81591, Santa Cruz).

1.2. Evaluation of Antigen Immunogenicity

Antigen immunogenicity was evaluated in vivo by Elispot IFNγ and intracellular cytokine staining (ICS) assays following immunization of HLA transgenic mice.

1.2.1 Mouse Model

The HLA-A2.1 transgenic mice used in the study were described by Pascolo et al. (1997, J. Exp. Med. 185:2043). These mice have the H-2D$^b$ and murine β$_2$-microglobulin genes knocked-out and express a transgenic monochain histocompatibility class I molecule (HHD molecule) in which the C-terminus of the human β2m is covalently linked to the N-terminus of a chimeric heavy chain (HLA-A*0201 α1-α2, H-2D$^b$ α3 transmembrane and intracytoplasmic domains). Seven to 10 weeks-old mice (male and female) were immunized. Average weight of the mice was around 25-30 g.

1.2.2. Immunization Protocols

Mice were divided in 4 groups; group 1 immunized by AdTG17909 (encoding HBV Core fused to env1, env2 and env4 immunogenic domains), group 2 immunized AdTG17910 (encoding the truncated and mutated Pol*), group 3 immunized with both vectors and group 4 immunized with an empty adenovirus (AdTG15149) as negative control. All animals were immunized by subcutaneous injection at the base of the tail, groups 1 and 2 animals received one subcutaneous injection of $10^8$ IU of each Adenovirus (TG17909 or TG17910), group 3 one subcutaneous injection of a mix containing $10^8$ IU of each adenovirus (total of 2·$10^8$ IU: $10^8$ IU of AdTG17909+$10^8$ IU of AdTG17910) and negative controls received one subcutaneous injection of 2·$10^8$ IU of AdTG15149. Cellular immune responses were assessed by IFNg Elispot and intracellular cytokine staining (ICS) assays 2 weeks after the immunization.

1.2.3 Peptides

Peptides used for cells stimulation in vitro were either short peptides of 9 to 10 amino acids which are described or predicted as HLA-A2 restricted epitopes or long peptides of 15 amino acids included in peptide libraries covering all the antigens of interest.

Short peptides corresponding to described or predicted HLA-A2 restricted epitopes of Polymerase protein, Core protein or Env domains were synthesized by Eurogentec (Belgium) and were dissolved in 100% DMSO (sigma, D2650) at a concentration of 10 mM.

Peptides libraries covering the whole Polymerase, Core and Envelope proteins were synthesized by PROIMMUNE (Oxford, United Kingdom). The Pol, Core and Env libraries were composed of 15 mer peptides overlapping by 11 amino acids. Each crude peptide was dissolved in 100% DMSO (sigma, D2650) at a concentration of 50 mg/ml. For each library, peptides were pooled to a concentration of 2 mg/ml per peptide:

HBV Pol protein is covered by 8 pools of 24 to 25 peptides from Pol library (Pool 1: 24 peptides covering residues 45 to 151; Pool 2: 24 peptides covering residues 140 to 251; Pool 3: 24 peptides covering residues 241 to 347; Pool 4: 24 peptides covering residues 337 to 447; Pool 5: 24 peptides covering residues 437 to 543; Pool 6: 24 peptides covering residues 533 to 639; Pool 7: 24 peptides covering residues 629 to 735; Pool 8: 25 peptides covering residues 725 to 832);

HBV Core protein is covered by 2 pools of 21-22 peptides from Core library (Pool 1: 22 peptides covering residues 1 to 100; Pool 2: 21 peptides covering residues 89 to 183);

HBV Env protein is covered by 3 pools of 6 to 10 peptides from Env library (Pool 1: 10 peptides covering HBs residues 9 to 59; Pool 2: 9 peptides covering HBs residues 157 to 194; Pool 4: 6 peptides covering HBs residues 193 to 226).

1.2.4. IFNg Elispot Assays

Splenocytes from immunized mice were collected and red blood cells were lysed (Sigma, R7757). $2 \cdot 10^5$ cells per well were cultured in triplicate for 40 h in Multiscreen plates (Millipore, MSHA S4510) coated with an anti-mouse IFNg monoclonal antibody (BD Biosciences; 10 µg/ml, 551216) in (MEM culture medium (Gibco, 22571) supplemented with 10% FCS (Sigma, F7524 or JRH, 12003-100M), 80 U/mL penicillin/80 µg/mL streptomycin (PAN, P06-07-100), 2 mM L-glutamine (Gibco, 25030), 1× non-essential amino acids (Gibco, 11140), 10 mM Hepes (Gibco, 15630), 1 mM sodium pyruvate (Gibco, 31350) and 50 µM β-mercaptoethanol (Gibco, 31350) and in presence of 10 units/ml of recombinant murine IL2 (Peprotech, 212-12), alone as negative control, or with:

10 µM of one HLA-A2 restricted peptide present in HBV antigens encoded by Ad vectors (SLY in Pol, FLP, ILC for Core, VLQ, FLG and GLS for Env) or an irrelevant one;

a pool of peptides at a final concentration of 5 µg/ml per peptide

5 µg/ml of Concanavalin A (Sigma, C5275) for positive control.

IFNg-producing T cells were quantified by Elispot (cytokine-specific enzyme linked immunospot) assay as previously described (Himoudi et al., 2002, J. Virol. 76:12735). The number of spots (corresponding to the IFNg-producing T cells) in negative control wells was substracted from the number of spots detected in experimental wells containing HBV peptides. Results are shown as the mean value obtained for triplicate wells. An experimental threshold of positivity for observed responses (or cut-off) is determined by calculating a threshold value which corresponds to the mean value of spots observed with medium alone+2 standard deviations, reported to $10^6$ cells. A technical cut-off linked to the CTL Elispot reader was also defined as being 50 spots/$10^6$ cells (which is the value above which the CV of the reader was systematically less than 20%). The highest value between the technical cut-off and the experimental threshold calculated for each experiment is taken into account to define the cut-off value of each experiment. Statistical analyses of Elispot responses were conducted by using a Mann-Whitney test. P value equal or inferior to 0.05 was considered as significant.

1.2.5. Intracellular Cytokine Staining (ICS) Assays

ICS was performed on splenocytes from each animal of each group. Following red blood cells lysis with lysis buffer (Sigma, R7757), $2 \times 10^6$ cells per well in flat-bottom 96-well plate were incubated in complete alpha (MEM culture medium (Gibco BRL, 22571) in presence of 10 units/ml of murine recombinant IL-2 (Peprotech, 212-12) alone as negative control or with 1 µM of specific HBV peptide or with a pool of peptides at a final concentration of 5 g/ml per peptide or with 1 µM of an irrelevant peptide. The GolgiPlug (BD Biosciences, 555029) was immediately added at a 1 µl/ml final concentration for 5 h. Then, cells were harvested in V-bottom 96-well plates and washed with 1% FCS-PBS. Staining was performed using monoclonal antibodies against CD3 (hamster MAb anti-CD3e-PE, dilution 1/200), CD8 (rat MAb anti CD8a-APC, dilution 1/600) and CD4 (rat MAb anti-CD4-PerCP, dilution 1/600) (all from BD Biosciences, 553063, 553035 and 553052 respectively) in 50 µl of 1% FCS-PBS for 15 min at room temperature. After washing, cells were fixed and permeabilized with Cytofix/Cytoperm and washed with Perm/Wash solution (BD Biosciences, 554714). Then, the anti-mouse IFNg-PE antibodies (BD Biosciences, 554412557724) and anti-mouse TNFa-Alexa488 antibodies (BD Biosciences, 557719) or the anti-mouse IFNg-PE antibodies (BD Biosciences, 554412557724) and anti-mouse IL2-Alexa488 antibodies (BD Biosciences, 557719) were added for 15 min at room temperature and after washing with Perm/Wash, cells were resuspended in 1% FCS-PBS and analysed by flow cytometry using a FacsCalibur (Becton Dickinson). CD3e+, CD8a+ cells or CD3e+, CD4+ cells were gated to determine percentages of IFNg+CD8+ or IFNg+CD4+ T or TNFa+ CD8+ or TNFa+CD4+ T or IL2+CD8+ or IL2 CD4+ T or IFNg+ TNFa+CD8+ or IFNg+ TNFa+CD4+ or IFNg+ IL2+ CD8+ or IFNg+ IL2+CD4+ T cell population. The percentage obtained in medium only was considered as background.

1.2.6. In Vivo CTL Assays

In vivo CTL assays were performed as described (Fournillier et al., 2007). Splenocyte suspensions were obtained from syngenic mouse spleens and adjusted to $20 \times 10^6$ cells/ml after lysis of red blood cells. One third of the cells was incubated with one of the HBV specific peptide, the second third of the cells was incubated with another HBV peptide, all at 10 µM final concentration for 1 hour at 37° C., whereas the last fraction was left unpulsed. 5(6)-carboxyfluorescein diacetate succinimidyl ester (CFSE) (Molecular probes, C1157) was added at 16 µM (CFSE-high) to unpulsed cells, at 4 µM (CFSE-medium) to ILC or VLQ peptide pulsed cells and at 1 µM (CFSE-low) to SLY or FLP peptide pulsed cells, for 10 min. After washing with PBS, the three populations (unpulsed, ILC and SLY peptide pulsed cells or unpulsed, FLP and ILC peptide pulsed cells) were mixed and $30.10^6$ total cells were injected to anaesthetized mice via the retro-orbital vein (using ketamine-xylazine-PBS mix (Ketamine Virbac, Centravet KET204, final concentration 25 mg/ml; Xylazine hydrochloride Rompun Bayer, Centravet, final concentration 5 mg/ml)). Thus, CFSE-low and medium population represented specific targets supposed to be lysed by cytotoxic T cells and CFSE-high population was an internal reference allowing assay normalisation. Splenocytes from recipient mice were analyzed 24 h later by flow cytometry to detect the CFSE-labeled cells. Following gating on lymphocytes (SSC/FSC), a second gating was performed based on the number of events/CFSE fluorescence (FL1) which reveals 3 peaks, a 1rst one corresponding to CFSE-low cells, the 2nd one to CFSE-medium cells and the 3rd one to CFSE-high cells. For each animal, ratio between CFSE+ peptide-pulsed targets and CFSE+ unpulsed targets was calculated (R=Number CFSE-low cells/Number CFSE-high cells). Two naive mice were used to determine R reference. The percentage of specific lysis for each animal was determined by the following formula: % lysis=(1−

$R_{mouse}/R_{reference}) \times 100$. A response was considered positive if the percentage of specific lysis was higher than 10% (cut-off).

2. Results

2.1 Antigen Expression by Viral Vectors

2.1.1 Expression of Antigens from Adenovirus Constructs AdTG17909 and AdTG17910

Expression of the core-env1-env2-env4 fusion protein was evaluated by Western-blot. A549 cells ($10^6$ cells) were infected at MOI of 10 or 50 for 48 hours with AdTG17909 or an empty adenovirus as negative control. The cell pellets were collected and probed with an anti-Core mouse monoclonal antibody (C1-5, sc-23945, Santa Cruz). As illustrated in FIG. 1A, a major band having the expected molecular weight (31.6 kDa) was revealed in the sample collected from cells infected with AdTG17909.

Expression of the Pol* polypeptide was evaluated by Western-blot following AdTG17910 infection of A549 cells. The cell pellets were then collected and probed with an anti-Pol mouse monoclonal antibody (8D5, sc-81591, Santa Cruz). As illustrated in FIG. 1A, a band having the expected molecular weight (88.5 kDa) was revealed in the sample collected from cells infected with AdTG17910 together with some sub-products (partial polymerase proteins).

2.1.2 Expression of Antigens from MVA Constructs

Analysis of Pol*, Pol*TMR, Core*t, Core*tEnv1, Core*-Env1-Env2 expression was performed by Western-blot. A549 cells or CEF were infected at MOI of 1 or 0.2 respectively with MVATG17842, MVATG17843, MVATG17971, MVATG17972, MVATG17993, and MVATG17994 respectively in presence or in absence of proteasome inhibitor MG-132 (10 µM) added to growth medium for MVATG17842 and MVATG17843. After 24 hours, cells were harvested.

For MVATG17842, Western-blot analysis was performed using commercial monoclonal anti-Pol antibody Hep B Pol (8D5, Santa Cruz, #sc-81591). As shown in FIG. 1B, expression of a protein with an apparent molecular weight of 88.5 kDa was detected only in presence of MG-132. This band has the expected molecular weight for the Pol* protein.

For MVATG17843, Western-blot analysis was performed using commercial monoclonal anti-Pol antibody Hep B Pol (8D5, Santa Cruz, #sc-81591). As shown in FIG. 1B, expression of a protein with an apparent molecular weight of 98.2 kDa was detected in presence or in absence of MG-132. This band has the expected molecular weight for the Pol*-TMR protein. It should be noticed that in presence of MG132 more product and an additional product of high molecular weight, over 200 KDa, were detected.

For MVATG17971, Western-blot analysis was performed using a commercial monoclonal anti-core antibody Hep B cAg (13A9) (Santa Cruz, #sc-23946). As shown in FIG. 1B, expression of Core* was detected with an apparent molecular weight of 21 kDa which corresponds to the expected molecular weight.

For MVATG17972, Western-blot analysis was performed using a commercial monoclonal anti-core antibody Hep B cAg (13A9) (Santa Cruz, #sc-23946). As shown in FIG. 1B, expression of Core*t was detected with an apparent molecular weight of 15.8 kDa which corresponds to the expected molecular weight.

For MVATG17993 and MVATG17994, Western-blot analysis was performed using a commercial monoclonal anti-core antibody Hep B cAg (13A9, Santa Cruz, #sc-23946). As shown in FIG. 1B, expression of a protein with an apparent molecular weight of 19.9 and 23.4 kDa respectively was detected. This band has the expected molecular weight for the Core*t-Env1 protein and Core*t-Env1-Env2

2.2. Immunogenicity of Antigens Expressed from Adenovirus Vectors AdTG17909 and AdTG17910

The immunogenicity of the HBV polypeptides expressed by adenovirus vectors was assessed in HLA-A2 transgenic mice immunized with either AdTG17909 or AdTG17910 alone or with a mixture of the 2 adenoviruses. Specific T cell responses induced following one subcutaneous injection were evaluated by Elispot IFNg, ICS and in vivo cytolysis assays using known (described as being the target of specific T cell responses in patients) HLA-A2 epitopes present in Polymerase, Core or the envelope domains or/and pools of overlapping peptides covering the HBV antigens of interest.

2.2.1. HBV Specific IFNγ Producing Cell Evaluation by Elispot Assays

Elispot IFNg assays showed that AdTG17910 is able to induce IFNg producing cells specific of an HLA-A2 restricted epitope (SLYADSPSV) (SEQ ID NO: 55) located within the HBV polymerase at positions 816-824) (FIG. 2A). Immunization with AdTG17909 also resulted in high frequency induction of IFNg producing cells specific for 2 Core HLA-A2 restricted epitopes (FLPSDFFPSV at position 18-27 (SEQ ID NO: 56) and ILCWGELMTL at position 99-108 (SEQ ID NO: 57) as well as for 3 envelope HLA-A2 restricted epitopes (VLQAGFFLL (SEQ ID NO: 58) at positions 14-22 and FLGGTTVCL (SEQ ID NO: 59) at positions 41-49 both present in Env1, and GLSPTVWLSV (SEQ ID NO: 60) at positions 185-194 present in Env2) (FIGS. 2B and C). Immunization with the mixture of AdTG17909 and AdTG17910 also induced a comparable level of specific IFNg producing cells targeting the same epitopes in the 3 antigens, i.e. the SLY epitope present in Pol, the FLP and ILC epitopes in the Core protein, and the 3 epitopes of the envelope domains (VLQ, FLG and GLS) (FIGS. 2A, B and C). Frequency of T cell responses detected following immunization with a single Ad or the mixture of the two was comparable, showing that there is no major immunodominance between the 3 antigens expressed from the described vectors.

2.2.2. HBV Specific IFNg/TNFa Producing Cell Evaluation by Intracellular Staining Assays The number of CD8 T cells able to produce either IFNg alone or IFNg+ TNFa targeting HLA-A2 restricted epitopes present in polymerase (SLY) in Core (FLP and ILC) and in envelope domains (VLQ, FLG and GLS) were evaluated by ICS assay. All these epitopes were the target of double and simple secreting cells. The results are shown in FIGS. 3A-3C. Animals immunized with AdTG17909 alone or in combination with AdTG17910 mounted roughly equivalent Core- and Env-specific CD8 T cell responses (same percentages of specific CD8 T cells producing IFNg or IFNg+TNFa following restimulation with FLP, ILC, VLQ, FLG and GLS peptides as shown in FIGS. 3B and 3C). On the other hand, concerning the polymerase specific CD8 T cell response (SLY epitope), a very high percentage of CD8+ cells producing IFNg or IFNg+TNFa was detected in mice treated with AdTG1710 expressing Pol* (FIG. 3A) as well as in those immunized with the mixture of AdTG17910 and AdTG17909 although at a lower level (FIG. 3C).

2.2.3. HBV Specific IFNg/TNFa Producing CD8 and CD4 T Cell Evaluation Following Immunization with a Mix of Adenovirus Vectors, by Intracellular Staining Assays The percentages of CD8 and CD4 T cells able to produce either IFNg alone or IFNg+TNFa or IFNg+IL2 targeting HLA-A2 restricted epitopes present in polymerase (SLY) in Core (FLP and ILC) and in envelope domains (VLQ, FLG and GLS) or pools of overlapping peptides covering Core protein and Env domains were evaluated by ICS assay. All the tested HLA-A2 restricted epitopes were the target of single and double secreting cells (IFNg and IFNg+TNFa) and some pools of overlapping peptides were the target of single and double producing cells too (IFNg and IFNg+TNF and IFNg+IL2). The results are shown in FIGS. 4A-4C. Five HLA-A2 transgenic mice were immunized with a mix of AdTG17909 and AdTG17910 and 3 HLA-A2 transgenic mice were immunized with AdTG15149 (negative control). Animals immunized with AdTG15149 displayed no HBV-specific T cell responses (data not shown). Animals immunized with AdTG17909 combined with AdTG17910 displayed a strong CD8 T cell response specific of HBV targeted antigens (FIG. 4A), with high percentage of single (IFNg) and double (IFNg+TNFa) producing cells specific of the HLA-A2 epitopes present in Polymerase, Core and Env domains and specific of the "core 1" pool of peptides and the pools of peptides covering Env1 and Env2 domains. As illustrated in FIGS. 4B and 4C, these vaccinated mice also displayed CD4 T cell responses specific of HBV antigens, in particular single (IFNg) and double (IFNg+TNFa and IFNg+IL2) producing cells specific of the "core 2" pool of peptides and the Env2-covering pool of peptides.

2.2.4. Induction of In Vivo Cytolysis Measured by In Vivo CTL Assays

The ability of adenovirus vectors AdTG17909 and AdTG17910 to induce in vivo cytolysis against cells presenting HBV HLA-A2 epitopes was assessed by in vivo CTL assays. Four HLA-A2 epitopes were tested, respectively SLY (Pol), FLP and ILC (Core) and VLQ (Env 1 domain). Six animals were immunized with a mix of AdTG17909+AdTG17910 and 2 animals were immunized with AdTG15149 (negative control). The half of each group (three AdTG17909+AdTG17910 immunized mice and one AdTG15149 immunized mouse) was tested for its ability to lyse in vivo cells pulsed with SLY peptide and cells pulsed with ILC peptide. The other half was tested for the ability of the vaccinated animals to lyse in vivo cells pulsed with FLP peptide and cells pulsed with VLQ peptide. The results are shown in FIGS. 5A and 5B. As expected, no HBV-specific in vivo cytolysis could be detected with AdTG15149 immunized mice (data not shown). In vivo cytolysis against the 2 core epitopes FLP and ILC was weak in AdTG17909+AdTG17910 immunized mice. However, in contrast, animals immunized with the mixture of AdTG17909 and AdTG17910 displayed a strong in vivo cytolysis against the polymerase epitope SLY (FIG. 5A) and Env1 epitope VLQ (FIG. 5B), reaching more than 50% of specific lysis in both cases.

Interestingly, the combination of Ad vectors expressing pol, core and env moieties allows the induction of specific T cell responses targeting the 3 HBV antigens when co-injected. Induced T cells are able to produce one or 2 cytokines and to lyse in vivo cells loaded with some HBV peptides. All together these data demonstrate the immunogenic activity of the compositions described and their ability to induce CD8 and CD4 T cell responses when vectorised by Ad.

2.3. Immunogenicity of antigens expressed from MVA vectors MVATG17842, MVATG17843, MVATG7971, MVATG179 72, MVATG17993 and MVATG17994 The immunogenicity activity of the MVA-based compositions was assessed in HLA-A2 transgenic mice immunized with one of the MVA vectors described in Examples 1.1.2 to 1.1.7 (MVATG17842, MVATG17843, MVATG17971 or MVATG17972 alone) or with a mixture of 2 MVA (MVATG17843+MVATG17972, MVATG17843+MVATG17993 or MVATG17843+MVATG17994). Mice were immunized with three subcutaneous injections at one week interval and specific T cell responses were evaluated by Elispot IFNg and ICS using the above-described HLA-A2 epitopes present in Polymerase, Core or the envelope domains or/and pools of overlapping peptides covering the HBV antigens of interest.

2.3.1. HBV Specific IFNγ Producing Cell Evaluation by Elispot Assays Following Immunization with Polymerase Expressing MVA.

Three mice were immunized with either MVATG17842 expressing a truncated and mutated polymerase antigen or MVATG17843 expressing a membrane-targeted version of the same truncated and mutated polymerase or MVA N33.1 (negative control). Polymerase-specific T cell responses were evaluated by IFNg Elispot assays using the SLY HLA-A2 restricted epitope and pools of peptides covering the polymerase. No HBV-specific T cell response was detected for mice immunized with MVA N33.1 and with MVATG17842 (data not shown). However, as shown in FIG. 6A, IFNg producing cells were induced following immunization with MVATG17843 which are specific of the HLA-A2 restricted epitope SLY and of the peptide pool 8 covering the C-terminal portion of the polymerase (No specific response could be detected against the other peptide pools 1-7 under the tested experimental conditions). These data highlight the benefit of expressing polymerase as a membrane-anchored antigen at least in MVA-based compositions.

2.3.2. HBV Specific IFNγ Producing Cell Evaluation by Elispot Assays Following Immunization with Core Expressing MVA.

Eighth mice were immunized with either MVATG17971 expressing a core moiety deleted of residues 77-84 or MVATG17972 expressing a truncated version thereof (C-terminal truncation from residue 149) or MVA N33.1 (negative control). Core specific T cell responses were determined by IFNg Elispot assays using HLA-A2 restricted epitopes (FLP and ILC peptides) and the above-described core 1 and core 2 pools of peptides. As illustrated in FIG. 6B, immunization with MVA TG17971 is able to induce sporadic T cell responses specific against HLA-A2-restricted FLP and ILC peptides and the two peptide pool covering core antigen (FIG. 6B). No core specific T cell responses could be detected in mice immunized with MVATG17972 using the tested peptides and under the tested experimental conditions (data not shown).

2.3.3. HBV Specific IFNγ Producing Cell Evaluation by Elispot Assays Following Immunization with Combination of MVA Vectors.

Three mice were immunized with a mixture of MVA TG17843 and either MVA TG17972, MVA TG17993 and MVA TG17994 and HBV specific T cell responses were evaluated by Elispot IFNg assay using the above-described peptides.

Polymerase specific T cell responses were detected in the vast majority of animals vaccinated with the combination MVATG17843+MVATG17972 (positive responses in ⅔ animals as shown in FIG. 7A), MVATG17843+MVATG17993 (positive responses in 3/3 animals as shown in FIG. 7B) and MVATG17843+MVATG17994 (positive responses in ⅔ animals as shown in FIG. 7C). Frequency of IFNg producing cells seems to be comparable with the one observed when MVA TG17843 was injected alone (FIG. 6A) which demonstrates that vector combination is not detrimental to the induced immune response.

no core-specific response could be detected under the experimental conditions tested in any of the vaccinated animals using HLA-A2 or pools of peptides (data not shown).

no env-specific response could be detected under the experimental conditions tested in any of the animals vaccinated with the MVATG17993-comprising combination using Env1 HLA-A2 or pools of peptides (data not shown).

Env 2-specific T cell responses were detected in 2 out of 3 animals immunized with the MVATG17994-comprising combination as illustrated in FIG. 7C which were directed against both the HLA-A2-restricted GLS epitope and the Env2-covering pool of peptides (no detection of T cell response against Env1 domain could be observed under these experimental conditions; data not shown).

ICS assays performed in the same conditions confirmed the results observed in Elispot assays (data not shown).

Interestingly, the combination of MVA vectors expressing pol, core and env moieties allows the induction of specific T cell responses targeting the pol and env2 antigens when co-injected.

All together, these data demonstrate the immunogenic activity of the compositions described and their ability to induce T cell responses against the major HBVantigens.

3. Cross Reactivity of T Cells Induced by HBV AdTG17909 and AdTG17910 Vaccine Candidates At present time, 10 genotypes and many subtypes have been defined for HBV based on the natural variability existing within HBV proteins. As discussed in the above description, the divergence in the complete viral genomic sequence is more than 8% between genotypes and from 4% to 8% between subtypes. The geographic distribution of these HBV genotypes is different depending on the regions of the world (Lin et al, 2011, J. Gastro Hepatol. 26, 123-130). The genotype A is mainly prevalent in Africa and in northern Europe. Genotypes B and C are highly prevalent in Asia, in particular in China and the genotype D is mostly represented in Europe and mediterranean countries. The genotype F is found in South America as well as Central America where the genotype H is also represented. The genotype G is found in France and Germany for Europe and in the United States. Although the distribution of the newly identified genotypes I and J remains to be sharpened, they have been mainly found in Vietnam, Laos and Japan.

As described above (e.g. in example 2.2) AdTG17909 and AdTG17910 induced potent IFNg T cell responses against six HLA-A2 restricted epitopes. It is interesting to document the cross-reactive potential of T cell responses induced by such genotype D-based vaccine candidates against B and C genotypes HBV viruses. Only few publications addressed the question of the T cell cross-reactivity in the HBV context (Liu et al., 2007, Clin. Immunol. 125, 337-345; Riedl et al., 2006, J. Immunol. 176, 4003-4011).

The cross-reactivity study described hereinafter was conducted in 2 steps:

The 1$^{rst}$ step was an in silico analysis of sequences from genotypes B, C and D in order to determine the theoretical variability both intra- and inter-genotype at the global antigen level and at the T cell epitope level by identifying major, minor and rare variants of known T cell epitopes within HBV antigens of interest.

A 2$^{nd}$ step was an in vivo analysis in a preclinical mouse model in order to determine whether T cells induced by the genotype D based HBV vaccine candidates are able to recognize epitope variants from genotype B, C and D.

3.1 Materials and Methods 3.1.1 in Silico Study of HBV Sequences

The natural variation of sequences of HBV antigens and T cell epitopes within one viral genotype and among different viral genotypes, was evaluated by conducting various queries in "GeneBank" Nucleotide database. For illustrative purposes, a preliminary query based on "Hepatitis B virus" and "whole genome" and "Genotype B, C or D", and "not fulminant" key words resulted in 455, 827 and 369 entries for genotypes B, C and D respectively; Entries with indication "non-functional protein" for either of proteins of interest were skipped. Generator of random numbers were then used for selection of a given entry, for which accession number and amino acid sequences of each protein of interest (Polymerase, Core and Envelope) were downloaded in Excel spreadsheet program as text variables. Selection process was renewed until the limit of 100 acceptable sequences for each of B, C and D genotypes that fit with the defined criteria was reached.

3.1.2 Sequences Alignment and Definition of a Consensus Sequence Per Genotype

For each protein of interest, alignments of the 100 selected sequences/genotypes were performed using ClustalW2 program on EMBL site (www.ebi.ac.uk/Tools/msa/clustalw2/) using default options. Results were downloaded in MS Word file. The obtained consensus sequences for genotypes B, C and D were then aligned with the genotype D prototype sequence (Y07587) encoded by AdTG17909 and AdTG17910 HBV vaccine candidates.

3.1.3 Study of Epitope Variant Distribution

The study of epitope variant distribution was focused on class I epitopes restricted by HLA haplotypes that are mainly represented in Caucasian (HLA-A2, HLA-B7) and Asian (HLA-A24 and -A11) populations and 49 different epitopes were selected on this basis.

Their natural variants were searched through protein sequences selected as previously described. The total number of sequences per genotype that include every given variant was obtained. Since exactly 100 sequences per genotype were studied, these numbers are equivalent to variant frequencies (expressed in %). Epitope variants existing in more than 50% of sequences of one genotype were called "major" variants. Epitope variants existing in 5% to 50% of sequences of one genotype were called "minors" variants. Epitope variants existing in less than 5% of sequences of one genotype were referred as "rare" variants. Major variant were identified for each epitope and each genotype and then aligned and compared.

3.1.4. Epitope Variants Selected for Ex Vivo Testing

As illustrated in the following Table 1, major and minor variants of the 6 HLA-A2-restricted epitopes against which AdTG17909 and AdTG17910 induced potent IFNg T cell response were selected and synthesized as peptides to be tested in ex-vivo experiments. Rare variants (representing <5% of sequences) were not considered in the study.

TABLE 1

The six HLA-A2 restricted epitopes selected for ex-vivo testing, major and minor variants and frequencies.

| HBV protein | epitope | Name | sequence | Percentage Genotype D | Genotype C | Genotype B |
|---|---|---|---|---|---|---|
| Core | FLP | FLP | FLPSDFFPSV (SEQ ID NO: 56) | 85 | 12 | 7 |
| | | FLP4 | FLPSDFFPSI (SEQ ID NO: 62) | 1 | 84 | 79 |
| | ILC | ILC | ILCWGELMTL (SEQ ID NO: 57) | 69 | 3 | 4 |
| | | ILC2 | ILCWGELMNL (SEQ ID NO: 63) | 4 | 68 | 71 |
| | | ILC3 | IVCWGELMNL (SEQ ID NO: 64) | 0 | 6 | 15 |
| | | ILC4 | ILCWGDLMTL (SEQ ID NO: 65) | 11 | 0 | 0 |
| | | ILC5 | IVCWGELMTL (SEQ ID NO: 66) | 0 | 6 | 0 |
| | | ILC6 | ILCWVELMNL (SEQ ID NO: 67) | 0 | 5 | 1 |
| | | ILC7 | VLCWGELMTL (SEQ ID NO: 68) | 1 | 5 | 0 |
| Env | VLQ | VLQ | VLQAGFFLL (SEQ ID NO: 58) | 97 | 93 | 78 |
| | | VLQ2 | VLQAGFFSL (SEQ ID NO: 69) | 0 | 2 | 11 |
| | FLG | FLG | FLGGTTVCL (SEQ ID NO: 59) | 84 | 4 | 0 |
| | | FLG2 | FLGGTPVCL (SEQ ID NO: 70) | 3 | 2 | 72 |
| | | FLG3 | FLGGAPTCP (SEQ ID NO: 71) | 1 | 68 | 5 |
| | | FLG4 | FLGETPVCL (SEQ ID NO: 72) | 0 | 0 | 10 |
| | GLSP | GLSP | GLSPTVWLSV (SEQ ID NO: 60) | 78 | 94 | 96 |
| | | GLSP2 | GLSPTVWLLV (SEQ ID NO: 73) | 9 | 0 | 1 |
| | | GLSP3 | GLSPIVWLSV (SEQ ID NO: 74) | 6 | 0 | 1 |
| Pol | SLY | SLY | SLYADSPSV (SEQ ID NO: 55) | 89 | 5 | 87 |
| | | SLY2 | SLYAVSPSV (SEQ ID NO: 75) | 4 | 81 | 6 |

3.1.5 Immunization and Read Out

The HLA-A2.1 mice were immunized by subcutaneous route with a mixture of AdTG17909 and AdTG17910 containing $10^8$ iu of each Ad preparation or with $2 \times 10^8$ iu of the empty AdTG15149 as a negative control. Thirteen to 15 days after immunization, animals were euthanized and spleens were aseptically removed for further ex-vivo Elispot IFN-gamma assay and Intracellular Cytokine Staining (ICS) analysis.

IFNg Elispot assays were performed as described in Example 1.2.4 except the peptides used for stimulation:
Irrelevant peptide (10 μM, DLMGYIPLV HLA-A2 peptide from HCV Core, synthesized by Eurogentec; SEQ ID NO: 76) or,
Concanavalin A (5 μg/ml Sigma, C5275) as a positive control or,
HBV Pol, Core and Env selected peptides described in Table 1 (10 μM, synthesized by Eurogentec).

Results are shown as the mean value obtained for triplicate wells, related to $10^6$ cells. The technical cut-off linked to variability of the CTL ELISpot reader is 10 counted spots/well as it has been determined that 10 counted spots is the threshold above which the variation coefficient is never more than 20%. According to this technical cut-off, in this study, a response was then considered positive if the number of spots was higher than 50 spots per $10^6$ cells. The experimental cut-off defined as the mean number of spots observed with medium alone+2 Standard Deviations (SD) was also calculated. Only specific responses displaying a number of spots higher than the 2 cut-offs are considered as positive.

Double Intracellular Cytokine Staining Assays (IFNg/TNFa were performed as described in Example 1.2.5. CD8+ CD4− cells were gated and presented on IFNg/TNFa dot-plot. Four quadrants were defined to gate positive cells for either one cytokine (IFNg-SP or TNFa-SP) or both cytokines simultaneously (IFNg/TNFa-DP) or cells negative for both cytokines. Numbers of events found in these quadrants were divided by total number of events in CD8+ CD4− parental population thus giving percentages of responding CD8+ T cells. For each mouse, the percentage obtained in medium alone was considered as background and subtracted from the percentage obtained with peptide stimulations. Response was considered positive if the percentage of stained cells was higher than 3 times the SD of background values (obtained with medium alone) found for all animals in the particular protocol and higher than 0.244% of CD8+ T cells (technical cut-off defined for HLA-A2 mice and based on ability of FacsCalibur to detect rare events).

Given that the percentage of TNFa-SP CD8$^+$ cells were never found above cut-off, analyses were done for total IFNg-positive CD8$^+$ cells accounting for both IFNg-SP and IFNg/TNFa-DP cells.

Statistical analysis of the resultswere performed using Statistica 9.0 (2009; StatSoft).

3.2 Results 3.2.1. In Silico Analysis ofHBV Sequence Variability

Analysis of the Whole Antigen Sequences

Consensus sequences of HBV polymerase, core and env antigens were obtained from multiple alignments of HBV sequences of genotypes B, C and D (100 sequences/genotype). These consensus sequences were aligned as described in Materials and Methods with the HBV genotype D near-consensus prototype sequence (Y07587) encoded by AdTG17909 and AdTG17910. The Y07587 sequence differs from the genotype D consensus sequence, by only 6 amino acids in the polymerase and one in Core. No amino acid difference was identified for the Envelope antigen. The sequence homologies and variations between the Y07587 sequence was also studied with respect to the consensus sequences of genotypes B and C. The results are presented in Table 2.

due to the insertion of 11 amino acids in the polymerase sequence of genotypes B and C compared with the sequence of genotype D. 39 amino acid positions are identical between genotypes C and D but different in genotype B (notation C=D≠B), etc and 21 positions are different in all genotypes (notation B≠C≠D). (see Table 2). For the Core protein, all amino acids are identical between genotypes B and C sequences (meaning that the consensus sequences from genotype B and genotype C are identical for the Core protein) and only 9 amino acids differ from the genotype D sequence. For the envelope protein, as for the polymerase protein, although most of amino acid positions are identical among the 3 genotypes (199 out of 226), differences are seen for 27 amino acids positions (B=C≠D; B=D≠C; C=D≠B). The most frequent case of difference was found when amino acids were identical between genotype C and D but different for genotype B (notation C=D≠B). Concerning the specific domains Env1, Env2 and Env4, the Env2 domain is mainly conserved with only one different amino acid among the 3 genotypes, which is conserved between genotypes B and C but differs from genotype D. The Env1 domain is slightly more variable (5 amino acids that differ among the 3 genotypes) with amino acids that are identical in 2 genotypes and differ in the 3rd one (B=C≠D; B=D≠C; C=D≠B). The Env4 domain is in an intermediary situation with 2

TABLE 2 sequence conservation between HBV consensus sequences from genotypes B and C and Y07587 genotype D sequence present in AdTG17909 and AdTG17910 vaccine candidates

| | | Antigens or domains ⇒ | | | | | |
|---|---|---|---|---|---|---|---|
| | | Pol | Core | Env | Env1 | Env2 | Env4 |
| | | Total number of amino acids ⇒ | | | | | |
| | | 843* | 183 | 226 | 38 | 30 | 25 |
| Number (and %) of amino acid positions within the antigen or domain for which conservation and differences are: | B = C = D | 700 (83%) | 174 (95%) | 199 (88%) | 33 (87%) | 29 (97%) | 23 (92%) |
| | B = C ≠ D | 57 (7%) | 9 (5%) | 7 (3%) | 1 (2.5%) | 1 (3%) | 1 (4%) |
| | C = D ≠ B | 39 (5%) | 0 | 12 (5%) | 1 (2.5%) | 0 | 1 (4%) |
| | B = D ≠ C | 26 (3%) | 0 | 8 (4%) | 3 (8%) | 0 | 0 |
| | B ≠ C ≠ D | 21 (2%) | 0 | 0 | 0 | 0 | 0 |

*accounting for 11 AA insertion observed in B and C genotypes.

In this alignment, when the amino acid is identical for the 3 sequences, it was referred as "B=C=D". When differences were observed among the 3 genotypes for an amino acid position, they were classified as follow: "B=C≠D" means that the amino acid is identical between genotype B and C but different for the genotype D, "B=D≠C" means that the amino acid is identical between genotype B and D but different for the genotype C, "C=D≠B" means that the amino acid is identical between genotype C and D but different for the genotype B, B≠C≠D means that the amino acid is different in all 3 genotypes. Number and percentage of conserved amino acid position as well as number and percentage of positions where differences were detected within each antigen and domain were also indicated. Of note, as shown in Table 2, the HBV proteins appeared highly conserved between genotypes B, C and D with very high percentages of homology, ranging from 83% for the polymerase protein to 95% for the Core protein. For the polymerase protein, although most of amino acid positions are identical among the 3 genotypes (700 out of 843), distinct differences were observed among the 3 genotypes for the 143 other amino acid positions. For example, 57 amino acid positions are identical between genotypes B and C but different for genotype D (notation B=C≠D). This is mainly different amino acids among the 3 genotypes, which are conserved in 2 genotypes but differ from the 3rd one (B=C≠D; C=D≠B).

Considering the full length sequences for each antigen, alignments confirm a very high conservation of HBV sequences among genotypes B, C and D. Various examples of differences and conservation among the 3 genotypes were observed for polymerase and HBsAg showing that genotypes B, C and D are similarly different for these antigens. The case of the core protein is quite different as consensus sequences of genotype B and C are strictly identical, suggesting a high identity of core protein sequences between these 2 genotypes. In addition, these Core consensus sequences are also very close to the Core genotype D sequence present in AdTG17909 as there is 95% of identity at the amino acid level. Overall, these results confirmed the very high conservation of the Core protein.

Analysis of the T Cell Epitope Sequences

The study of T cell epitope sequences was focused on class I epitopes restricted by HLA haplotypes that are mainly represented in Caucasian population (HLA-A2, HLA-B7) and in Asian population (HLA-A24, -A3, -A11). Forty-nine epitopes were studied for their variants in the different genotype sequences (summarized in Table 1). Epitope variants existing in more than 50% of sequences of one genotype were called "major" variants. Epitope variants existing in 5% to 50% of sequences of one genotype were called "minors" variants. Epitope variants existing in less than 5% of sequences of one genotype were referred as "rare" variants. The major variant of each epitope for each genotype was defined and major variants of the 3 genotypes were then compared (Table 3).

3.2.2. Cross Reactivity Studies Following AdTG17909 and AdTG17910 Immunization of HLA-A2 Transgenic Mice The ability of the AdTG17909 and AdTG17910 to induce IFNg producing cross-reactive T cells against the HBV Core, Envelope and Polymerase antigens was assessed in HLA-A2 transgenic mice immunized with a mix of $10^8$ iu of each Ad vector ($2 \times 10^8$ iu in total) by subcutaneous route.

TABLE 3 sequence conservation between HBV major epitope variants of genotypes B, C and D.

| | | Antigens and domains ⇒ | | | | | |
|---|---|---|---|---|---|---|---|
| | | Pol | Core | Env | Env1 | Env2 | Env4 |
| | | Total number of analysed class 1 epitopes ⇒ | | | | | |
| | | 18 | 17 | 14 | 4 | 4 | 5 |
| Number (and %) of epitopes for which major variants are classified as: | B = C = D | 16 (89%) | 9 (53%) | 8 (57%) | 2 (50%) | 4 (100%) | 1 (20%) |
| | B = C ≠ D | 0 | 8 (47%) | 0 | 0 | 0 | 0 |
| | C = D ≠ B | 0 | 0 | 4 (29%) | 1 (25%) | 0 | 3 (60%) |
| | B = D ≠ C | 2 (11%) | 0 | 0 | 0 | 0 | 0 |
| | B ≠ C ≠ D | 0 | 0 | 2 (14%) | 1 (25%) | 0 | 1 (20%) |

Major variants of studied epitopes (see Table 1) were obtained as described in Materials and Methods for each HBV genotypes (C, B and D). When the amino acid sequence was the same for major variants of all 3 genotypes, major variants of the epitope were referred as "B=C=D". When the amino acid sequence was the same for major variants of genotypes B and C but different from the one of genotype D, major variants of the epitope were referred as B=C≠D. When the amino acid sequence was the same for major variants of genotypes B and D but different from the one of genotype C, major variants of the epitope were referred as B=D≠C. When the amino acid sequence was the same for major variants of genotypes C and D but different from the one of genotype B, major variants of the epitope were referred as C=D≠B. When the amino acid sequence was different for major variants of the 3 genotypes, major variants of the epitope were referred as B≠C≠D. Number and percentage of epitopes with the same major variants among the 3 genotypes as well as number and percentage of epitopes with different major variants among genotypes are presented in Table 3 for the each antigen and domains.

As shown in Table 3, 18 class I epitopes of the polymerase protein were analysed: the major variants of 16 epitopes are identical between the 3 genotypes and the major variants of the 2 other epitopes are identical for genotypes B and D but differ from the major variant of genotype C. For the Core protein, 17 class I epitopes were analysed: the major variants of 9 epitopes are identical for the 3 genotypes and the major variants of 8 epitopes are identical for genotype B and C but differ from genotype D. For the envelope protein, 14 class I epitopes were analysed: major variants of 8 of them are identical among the 3 genotypes, 2 are different in the 3 genotypes and 4 are identical for genotypes C and D but different for the genotype B.

In conclusion the class I epitopes are mostly conserved among the 3 genotypes B, C and D. For 33 out of the 49 analysed epitopes, the main variant is identical for the 3 genotypes, for 14 epitopes the main variant is identical for 2 genotypes out of the 3 and for 2 epitopes only, the main variant is different for the 3 genotypes. These in silico results confirmed the high conservation of the amino acid sequences of HBV proteins at the T cell epitope level.

Splenocytes of vaccinated mice were collected 2 weeks after immunization and in vitro stimulated with peptides that are homologous to the sequence encoded by the AdTG17909 (Core and Env domains) or the AdTG17910 (Polymerase) or with the major and minor variants of genotype D, B and C (see Table 1). IFNg Elispot and ICS assays were performed as described in Materials and Methods Cross-Reactivity of T Cell Responses Targeting the HBV Core Antigen Two core epitopes were tested including the homologous genotype D FLP and ILC and their variants listed in Table 1 representative of genotypes B and C.

FLP epitope and variants: 13 mice were immunized by the AdMix and splenocytes of the immunized mice were stimulated with either the homologous (genotype D) FLP epitope (FLPSDFFPSV; SEQ ID NO: 56) or the major variant FLP4 representative of genotypes B and C (FLPSDFFPSI; SEQ ID NO: 62).

As illustrated in FIG. 8A, Elispots IFNg showed a similar frequency of responders against FLP and FLP4 (54% versus 46% respectively) and a similar frequency of specific IFNg producing cells recognizing FLP or FLP4. No statistical difference was observed between FLP and FLP4

As illustrated in FIG. 8B, IFNg ICS assay displayed a similar profile with the same responder frequency (92% in both cases) and the same level of responses comparing the FLP peptide and its FLP4 variant.

Elispots and ICS results lead to the conclusion that T cells induced by the Ad mix are mainly cross-reactive and able to recognize the major variants of FLP for genotype D (homologous sequence) and for genotype B and C (FLP4 sequence).

ILC Epitope and Variants:

The ILC peptide (ILCWGELMTL; SEQ ID NO: 57), homologous to the genotype D core sequence encoded by AdTG17909 was tested as well as six ILC variants (ILC2 to ILC7 identified in Table 1 and corresponding to SEQ ID NO: 63 to 68, respectively). ILC2 is the major variant of both genotypes B and C whereas ILC3 to 7, are minor variants of the 3 genotypes.

As shown in FIG. 8A, ELISpots IFNg assays showed a high frequency of responding mice against ILC as well as ILC2 and ILC5 variants. Lower frequency was observed for variants ILC3, 4 and 7 and no responding mouse for ILC6 variant. The level of responses observed against ILC2 and ILC5 reaches 62 and 43% respectively of the response against the ILC peptide. The level of responses against ILC3, 4, 6 and 7 is even lower, being less than 20% for ILC3, 4 and 7 and 2% for ILC6.

In ICS assay (FIG. 8B), a high frequency of responding mice (from 85% to 100%) was found for ILC and all variants, except the ILC6 (only one mouse out of 13 responding to ILC6). When comparing with the response observed against the homologous ILC peptide (100%), high level of responses was obtained after ILC2 and ILC5 stimulation (78% and 87% of the ILC-induced response). Level of responses targeting ILC3 (51%), ILC4 (28%) and ILC6 (1%) was statistically lower than the one targeting the ILC peptide. However, ILC7-induced response detected by ICS was much higher than the one measured in ELISpot.

The combined results of ELISpot and ICS assays lead to the conclusion that T cell responses induced by the AdTG17909 are mainly cross-reactive, recognizing the major ILC2 variant of genotype B and C as well as most of the minor variants of the 3 genotypes B, C and D. Number of responding mice is similar for all the variants (except ILC6), even if the level of responses displayed by these mice is statistically lower than the one targeting the homologous peptide ILC.

In conclusion for the Core protein, AdTG17909-induced T cell responses are mostly cross reactive against the major variants of the 3 genotypes and even some minor variants.

Cross-Reactivity of T Cell Responses Targeting the HBV Envelope

Three epitopes of the Envelope antigen (VLQ and FLG contained in Env1 domain and GLS contained in Env2 domain) and their variants were tested.

VLQ Epitope and Variants:

The VLQ peptide (VLQAGFFLL; SEQ ID NO: 58) is the major variant of the 3 genotypes B, C and D whereas VLQ2 (VLQAGFFSL; SEQ ID NO: 69) is a minor variant of genotype B (and rare variant of genotype C).

As shown in FIGS. 9A and 9B, Elispots IFNg assays (FIG. 9A) showed a high frequency of responding mice (100%) against VLQ itself whereas a significantly lower number of responding mice was detected against the VLQ2 (38%). ICS assays (FIG. 9B) confirmed this trend with lower frequency of responding mice against VLQ2 (77%) than against VLQ (100%) and a level of induced T cells which is significantly lower against VLQ2 than against VLQ (p=0.0028).

These results indicate that T cell response is cross-reactive against the minor VLQ2 variant of genotype B but less potent than the one against the VLQ peptide.

FLG Epitope and Variants:

ELISpot and ISC assays were performed using the FLG peptide (FLGGTTVCL; SEQ ID NO: 59), the major variant of genotype D and three other variants. FLG2 (SEQ ID NO: 70) is the major variant of genotype B, FLG3 (SEQ ID NO: 71) is the major variant of genotype C and FLG4 (SEQ ID NO: 72) is a minor variant of genotype B.

ELISpots IFNg assays (FIG. 9A) showed a high frequency of responding mice (85%) and a high level of T cell responses against the homologous peptide FLG. The frequency of responding mice for FLG2, 3 and 4 variants is drastically lower (respectively 15%, 54% and 8%) and the level of detected T cell responses is also lower than for the FLG peptide (respectively 4%, 21% and 3% of the level of T cell responses detected for FLG). Statistical analyses confirmed that these differences between FLG and the 3 variants are significant.

ICS assays (FIG. 9B) confirmed the same trend. A high frequency of responding mice (100%) and a high level of IFNg producing cells were detected for the FLG peptide and frequency of responding mice and level of T cell responses are significantly lower for FLG2 (8% of responding mice and 3% of the FLG-response), FLG3 (62% of responding mice and 29% of the FLG-response) and FLG4 (no responding mouse). Statistical analyses on these assays also confirmed that T cell responses observed against the 3 variants FLG2, 3 and 4 are significantly lower than the one against the FLG epitope.

Thus, Elispots IFNγ and ICS assays demonstrated that AdTG17909-induced T cell responses are poorly cross-reactive against the major variants of genotype B and C of the FLG epitope.

GLSP Epitope and Variants:

GLSP (GLSPYVWLSV; SEQ ID NO: 60) is the major variant of the 3 genotypes B, C and D and GLSP2 (SEQ ID NO: 73) and 3 (SEQ ID NO: 74) are minor variants of genotype D.

Elispots IFNg assays (FIG. 9A) showed a high frequency of responding mice (100%) as well as high frequency of specific T cells producing IFNg against the homologous peptide GLSP. Frequency of responding mice and of specific IFNg producing cells targeting the variants GLSP2 and GLSP3 are lower than those targeting GLSP. This difference is statistically significant comparing GLSP with GLSP2 or GLSP3.

ICS assays (FIG. 9B) showed the same trend with high frequencies of both responding mice and IFNg-producing T cells against the homologous GLSP peptide. A high frequency of responding mice was also observed against GLSP2 and GLSP3 (respectively 100% and 85%) but the frequency of IFNg-producing cells was lower than the one observed for GLSP (78% and 36% of the GLSP-specific response for GLSP2 and GLSP3). Statistical analyses showed that the difference between GLSP and GLSP3 is statistically significant but not between GLSP and GLSP2.

The T cell response specific of the GLSP peptide was strong, whatever the genotype, as the major variants of the GLSP epitope have the same amino acid sequences for the 3 genotypes. T cell responses targeting the GLSP2 and GLSP3 minor variants are cross reactive but to a poor extend for GLSP3

In conclusion, 2 out of the 3 HLA-A2 tested epitopes in the HBsAg domains encoded by AdTG17909 are highly conserved among the 3 genotypes. Thus, T cell responses targeting these epitopes are strong in all cases. For the FLG epitope which is not conserved between the 3 genotypes, the induced T cells targeting the major variants of genotype B and C are cross-reactive to some extent with a high frequency of responding mice but the level of T cell responses is significantly lower than levels observed against the homologous peptide.

Cross-Reactivity of T Cell Responses Targeting the HBV Polymerase

SLY Epitope and Variants:

The SLY peptide (SLYADSPSV; SEQ ID NO: 55) is the major variant of genotypes B and D. SLY2 (SLYAVSPSV; SEQ ID NO: 75) is the major variant of genotype C (other identified variants being only rare variants thus not analysed in the in vivo study).

As expected, ELISpot assays showed a high percentage of responding mice (100%) and a high frequency of induced IFNg producing T cells targeting the homologous SLY peptide. However, the ability of inducing SLY2-recognizing T cells was dramatically low with only 1 responding mouse out of the 10 tested mice. The same trend was observed in ICS with 100% of responding mice against the SLY peptide and 0% against the SLY2 peptide (significant difference).

Overall, our data show that induced SLY-specific T cell responses recognized the major variant of genotype B and D as this major variant is the same but are not able to recognize the major variant of genotype C. A global conclusion regarding cross-reactive responses targeting the polymerase cannot be fully derived as analysis was limited to a single epitope for this antigen.

3.3 Conclusion

The in silico study showed at the global antigen level that the amino acid sequence of Polymerase, Core and Envelope proteins is highly conserved within the same genotype but also among genotypes B, C and D. This study also highlights that the sequence is also highly conserved at the T cell epitope level within these 3 proteins between European (genotype D) and Asian haplotypes (genotypes B and C). It was assumed that the overlapping open-reading frames of the HBV genome provide a high constraint that may limit sequence variability and, thus, appearance of escape mutations in T cell epitopes. This is in contrast to what has been described for other viruses such as HCV for which effective T cell responses are thought to be responsible for the selection of escape mutants (Petrovic et al., 2011, Eur. J. Immunol. 42, 1-10).

The in vivo study focused on 6 HLA-A2 epitopes targeting T cells and identified in core (FLP and ILC) and polymerase (SLY) antigens and env domains (VLQ, FLG and GLSP). The ELISpot and ICS results showed that the T cell responses induced following AdTG17909 and AdTG17910 immunization are generally cross reactive and able to recognize the major variants of genotype B, C and D as well as some minor variants. This good level of cross-reactivity of induced T cells is due in some cases to the high conservation of sequences (major variants such as GLSP and VLQ epitopes are identical between the 3 tested genotypes and identical to the Y07587 sequence included in AdTG17909 or AdTG17910) but also to the capacity of induced T cells to recognize heterologous sequences (FLP and ILC epitopes). For 2 out of the 6 tested epitopes, SLY and FLG epitopes, the cross reactivity of T cell responses appeared to be weaker. The induced T cell responses are not able to recognize respectively the SLY major variant of genotype C (SLY2) and the FLG major variant of genotype B (FLG2) as no responding mice were detected. For the FLG major variant of genotype C, responding mice were detected, suggesting that cross reactivity exists but the level of T cell response is significantly lower than the one observed with the FLG epitope. It was also shown that the induced T cells are able to recognize some minor variants of these epitopes since mice are responding to these variants although the level of induced T cells is generally lower than against the homologous peptide. Overall, vaccination with a genotype D sequence in this mouse model allows inducing T cell responses recognizing 5 out of 6 genotype B major variants of the tested HLA-A2 epitopes as well as 5 out of 6 genotype *C major* variants of tested HLA-A2 epitopes. Even if this study is limited to HLA-A2 epitopes, these results are the proof of concept that a HBV genotype D prototype sequence encoded by a vectorized vaccine candidate is able to induce T cell responses that are mostly cross-reactive with HBV sequences of genotype B, C and D. The cross reactivity potential provided by genotype D-based AdTG17909 and AdTG17910 is in favour of a large use of such vaccine candidates not only restricted to genotype D-infected patients but also broadened to genotype B or C-infected patients.

---

The invention claimed is:

1. An infectious adenoviral particle comprising a nucleic acid molecule encoding (i), (ii), and (iii) polypeptides
wherein
(i) is a polymerase moiety comprising at least 450 amino acid residues of a polymerase protein originating from a genotype D HBV virus;
(ii) is a core moiety comprising at least 100 amino acid residues of a core protein originating from a genotype D HBV virus; and
(iii) is an env moiety comprising a first amino acid sequence set forth in SEQ ID NO: 12 and a second amino acid sequence set forth in SEQ ID NO: 13, and wherein said env moiety does not include any immunogenic domain(s) originating from preS1 and preS2 regions;
wherein either:
(a) at least 45 and at most 50 amino acid residue truncation of (i) at the N-terminus of a native HBV polymerase protein or
(b) at least 34 and at most 37 amino acid residue truncation of (ii) at the C-terminus of a native HBV core protein;
wherein said infectious adenoviral particle is capable of inducing a T cell response against at least one of said HBV moieties and said infectious adenoviral particle is E1-defective.

2. The infectious adenoviral particle of claim 1, wherein said infectious adenoviral particle is for use in a subject infected or suspected to be infected with an HBV from a genotype D.

3. A host cell comprising the infectious adenoviral particle according to claim 1.

4. A composition comprising the infectious adenoviral particle according to claim 1 and a pharmaceutically acceptable vehicle.

5. The composition according to claim 4 which further comprises one or more adjuvant(s) suitable for systemic or mucosal application in humans.

6. The composition according to claim 4 which is formulated for intramuscular or subcutaneous administration.

7. The composition according to claim 4, which comprises from about $10^5$ to about $10^{13}$ infection units of an adenoviral vector or of an infectious adenoviral particle.

8. The infectious adenoviral particle according to claim 2, a host cell comprising the infectious adenoviral particle according to claim 2, or the composition comprising the infectious adenoviral particle according to claim 2, wherein said use is used in combination with standard of care.

9. The infectious adenoviral particle according to claim 1, a host cell comprising the infectious adenoviral particle according to claim 1, or a composition comprising the infectious adenoviral particle according to claim 1, wherein said genotype D HBV viruses are from HBV isolate Y07587.

10. An adenoviral vector comprising nucleic acid molecules encoding (i), (ii), and (iii) polypeptides,
wherein
(i) is a polymerase moiety comprising at least 450 amino acid residues of a polymerase protein originating from a genotype D HBV virus;
(ii) is a core moiety comprising at least 100 amino acid residues of a core protein originating from a genotype D HBV virus; and
(iii) is an env moiety comprising a first amino acid sequence set forth in SEQ ID NO: 12 and a second amino acid sequence set forth in SEQ ID NO: 13 and wherein said env moiety does not include any immunogenic domain(s) originating from preS1 and preS2 regions;
wherein either:
(a) at least 45 and at most 50 amino acid residue truncation of (i) at the N-terminus of a native HBV polymerase protein or
(b) at least 34 and at most 37 amino acid residue truncation of (ii) at the C-terminus of a native HBV core protein;
wherein said adenoviral vector is capable of inducing a T cell response against at least one of said HBV moieties and said adenoviral vector is E1-defective.

11. The adenoviral vector of claim 10, wherein said wherein said adenoviral vector is for use in a subject infected or suspected to be infected with an HBV from a genotype D.

12. A host cell comprising the adenoviral vector according to claim 10.

13. A composition comprising the adenoviral vector according to claim 10 and a pharmaceutically acceptable vehicle.

14. The composition according to claim 13 which further comprises one or more adjuvant(s) suitable for systemic or mucosal application in humans.

15. The composition according to claim 13 which is formulated for intramuscular or subcutaneous administration.

16. The composition according to claim 13, which comprises from about $10^5$ to about $10^{13}$ infection units of an adenoviral vector or of an infectious adenoviral particle.

17. The adenoviral vector according to claim 11, a host cell comprising the adenoviral vector according to claim 11, or the composition comprising the adenoviral vector according to claim 11, wherein said use is used in combination with standard of care.

18. The adenoviral vector according to claim 10, a host cell comprising the adenoviral vector according to claim 10, or a composition comprising the adenoviral vector according to claim 10, wherein said genotype D HBV viruses are from HBV isolate Y07587.

19. A method of inducing an immune response in a subject infected with or suspected to be infected with an HBV, comprising administering the composition of claim 4 to said subject.

20. The method of claim 19, wherein the HBV infection is a chronic HBV infection.

21. A method of inducing an immune response in a subject infected with or suspected to be infected with an HBV, comprising administering the composition of claim 13 to said subject.

22. The method of claim 21, wherein the HBV infection is a chronic HBV infection.

* * * * *